(12) United States Patent
Nelson et al.

(10) Patent No.: US 7,326,696 B2
(45) Date of Patent: Feb. 5, 2008

(54) AMINO-METHYL SUBSTITUTED TETRACYCLINE COMPOUNDS

(75) Inventors: Mark L. Nelson, Norfolk, MA (US); Kwasi Ohemeng, Norwood, MA (US); Roger Frechette, Reading, MA (US); Paul Abato, Providence, RI (US); Victor Amoo, Daphne, AL (US); Haregewein Assefa, Braintree, MA (US); Joel Berniac, Stoneham, MA (US); Beena Bhatia, Mansfield, MA (US); Todd Bowser, Charlton, MA (US); Jackson Chen, Brookline, MA (US); Laura Honeyman, Roslindale, MA (US); Mohamed Y. Ismail, Bedford, MA (US); Oak Kim, Cambridge, MA (US); Rachid Mechiche, South Boston, MA (US); N. Laxma Reddy, Solon, OH (US); Atul K. Verma, Mansfield, MA (US); Peter Viski, Asharoken, NY (US); Tadeusz Warchol, Northborough, MA (US); Ivan Yanachkov, Newton, MA (US)

(73) Assignee: Paratek Pharmaceuticals, Inc., Boston, MA (US)

( * ) Notice: Subject to any disclaimer, the term of this patent is extended or adjusted under 35 U.S.C. 154(b) by 198 days.

(21) Appl. No.: 10/737,361

(22) Filed: Dec. 15, 2003

(65) Prior Publication Data
US 2005/0026875 A1 Feb. 3, 2005

Related U.S. Application Data

(63) Continuation of application No. 10/384,855, filed on Mar. 10, 2003, now abandoned.

(60) Provisional application No. 60/395,495, filed on Jul. 12, 2002, provisional application No. 60/362,654, filed on Mar. 8, 2002.

(51) Int. Cl.
*A61K 31/65* (2006.01)
*C07D 50/22* (2006.01)

(52) U.S. Cl. .............. 514/152; 514/325; 514/357; 514/365; 514/374; 514/385; 514/424; 514/427; 544/154; 544/238; 544/380; 546/61; 546/195; 546/285; 548/146; 548/215; 548/300.1; 548/528; 548/541; 548/560; 549/25; 549/384

(58) Field of Classification Search .............. 514/152, 514/325, 357, 365, 374, 385, 424, 427; 544/154, 544/238, 380; 546/61, 195, 285; 548/146, 548/215, 300.1, 528, 541, 560; 549/25, 384
See application file for complete search history.

(56) References Cited

U.S. PATENT DOCUMENTS 3,226,436 A 12/1965 Petisi et al.
RE26,253 E 8/1967 Petisi et al.
3,338,963 A 8/1967 Petisi et al.
3,341,585 A 9/1967 Bitha et al.
3,345,410 A 10/1967 Winterbottom et al.
3,373,196 A 3/1968 Bitha et al.
3,518,306 A 6/1970 Martell, Jr. et al.
3,579,579 A 5/1971 Hlavka et al.
3,901,942 A 8/1975 Luigi et al.
3,993,694 A 11/1976 Martin et al.
4,024,272 A 5/1977 Rogalski et al.
5,248,797 A 9/1993 Sum
5,281,628 A 1/1994 Hlavka et al.
5,284,963 A 2/1994 Sum et al.
5,326,759 A 7/1994 Hlavka et al.
5,328,902 A 7/1994 Sum et al.
5,371,076 A 12/1994 Lee et al.
5,380,888 A 1/1995 Sum et al.
5,386,041 A 1/1995 Sum et al.
5,401,729 A 3/1995 Sum et al.
5,401,863 A 3/1995 Hlavka et al.
5,420,272 A 5/1995 Sum et al.
5,430,162 A 7/1995 Sum et al.
5,442,059 A 8/1995 Sum et al.
5,457,096 A 10/1995 Sum et al.
5,466,684 A 11/1995 Sum et al.
5,494,903 A 2/1996 Hlavka et al.
5,495,018 A 2/1996 Sum et al.
5,495,030 A 2/1996 Sum et al.
5,495,031 A 2/1996 Sum et al.
5,512,553 A 4/1996 Sum et al.
5,529,990 A 6/1996 Hlavka et al.

(Continued)

FOREIGN PATENT DOCUMENTS

| GB | 921252 | 3/1963 |
| GB | 1469384 | 4/1977 |
| WO | WO-95/22529 A1 | 8/1995 |
| WO | WO-01/74761 A1 | 10/2001 |
| WO | WO-02/04406 A2 | 1/2002 |
| WO | WO-02/04407 A2 | 1/2002 |
| WO | WO-02/072031 A2 | 9/2002 |
| WO | WO-02/072532 A1 | 9/2002 |
| WO | WO-03/005971 A2 | 1/2003 |
| WO | WO-03/057169 | 7/2003 |

OTHER PUBLICATIONS

Nelson et al. "Prepparation of 9-substituted . . . " CA 136:102231 (2002).*
Draper et al. "Substituted tetracyclin . . . " CA 137:244598 (2002).*
Barden, Timothy C. et al, "'Glycylcyclines'. 3. 9-Aminodoxycyclinecarboxamides," *J. Med. Chem.*, vol. 37:3205-3211 (1994).

(Continued)

*Primary Examiner*—Celia Chang
(74) *Attorney, Agent, or Firm*—Lahive & Cockfield LLP; Elizabeth A. Hanley, Esq.; Cynthia M. Soroos, Esq.

(57) ABSTRACT

Aminomethyl substituted tetracycline compounds, pharmaceutical compositions, and methods of use thereof are discussed.

128 Claims, No Drawings

U.S. PATENT DOCUMENTS

| | | | |
|---|---|---|---|
| 5,530,117 A | 6/1996 | Hlavka et al. | |
| 5,567,692 A | 10/1996 | Sum et al. | |
| 5,639,742 A | 6/1997 | Lee et al. | |
| 5,675,030 A | 10/1997 | Krishnam et al. | |
| 5,834,450 A | 11/1998 | Su | |
| 5,886,175 A | 3/1999 | Sum et al. | |
| 6,500,812 B2 | 12/2002 | Nelson et al. | |
| 6,617,318 B1 | 9/2003 | Nelson et al. | |
| 6,624,168 B2 | 9/2003 | Nelson et al. | |
| 6,642,270 B2 | 11/2003 | Nelson et al. | |
| 6,683,068 B2 | 1/2004 | Nelson et al. | |
| 6,818,634 B2 | 11/2004 | Nelson et al. | |
| 6,818,635 B2 | 11/2004 | Nelson et al. | |
| 6,833,365 B2 | 12/2004 | Levy et al. | |
| 6,841,546 B2 | 1/2005 | Draper et al. | |
| 6,846,939 B2 * | 1/2005 | Nelson et al. | 552/205 |
| 6,849,615 B2 | 2/2005 | Nelson et al. | |
| 7,001,918 B2 | 2/2006 | Huss et al. | |
| 7,045,507 B2 * | 5/2006 | Draper et al. | 514/31 |
| 7,056,902 B2 | 6/2006 | Nelson et al. | |
| 7,067,681 B2 | 6/2006 | Nelson et al. | |
| 7,094,806 B2 | 8/2006 | Nelson | |
| 2002/0128237 A1 | 9/2002 | Nelson et al. | |
| 2004/0063674 A1 | 4/2004 | Levy et al. | |
| 2004/0092490 A1 | 5/2004 | Draper et al. | |
| 2004/0138183 A1 | 7/2004 | Nelson et al. | |
| 2004/0176334 A1 | 9/2004 | Nelson et al. | |
| 2004/0214800 A1 | 10/2004 | Levy et al. | |
| 2004/0214801 A1 | 10/2004 | Nelson et al. | |
| 2004/0242548 A1 | 12/2004 | Draper et al. | |
| 2004/0266740 A1 | 12/2004 | Huss et al. | |
| 2005/0020545 A1 | 1/2005 | Draper et al. | |
| 2005/0026876 A1 | 2/2005 | Nelson et al. | |
| 2005/0038002 A1 | 2/2005 | Nelson et al. | |
| 2005/0070510 A1 | 3/2005 | Draper et al. | |
| 2005/0119235 A1 | 6/2005 | Nelson et al. | |
| 2005/0137174 A1 | 6/2005 | Ohemeng et al. | |
| 2005/0143352 A1 | 6/2005 | Nelson et al. | |
| 2005/0143353 A1 | 6/2005 | Nelson et al. | |
| 2005/0187198 A1 | 8/2005 | Nelson et al. | |
| 2005/0215532 A1 | 9/2005 | Levy et al. | |
| 2005/0250744 A1 | 11/2005 | Levy et al. | |
| 2005/0282787 A1 | 12/2005 | Myers et al. | |
| 2005/0288262 A1 | 12/2005 | Bandarage et al. | |
| 2006/0003971 A1 | 1/2006 | Nelson | |
| 2006/0084634 A1 | 4/2006 | Huss et al. | |
| 2006/0089336 A1 | 4/2006 | Nelson et al. | |
| 2006/0148765 A1 | 7/2006 | Nelson | |
| 2006/0166945 A1 | 7/2006 | Abato | |
| 2006/0166946 A1 | 7/2006 | Nelson et al. | |
| 2006/0194773 A1 | 8/2006 | Levy | |
| 2006/0205698 A1 | 9/2006 | Nelson et al. | |
| 2006/0229282 A1 | 10/2006 | Nelson et al. | |

OTHER PUBLICATIONS

Berge, S.M. et al, "Pharmaceutical Salts," *J. Pharm. Sci.*, vol. 66:1-19 (1977).

Koza, Darrell J. et al, "Synthesis and Biological Evaluation of 9-Substituted Tetracycline Derivatives," *Bioorganic & Medicinal Chemistry Letters*, vol. 12:2163-2165 (2002).

Petersen, P.J. et al, "In Vivo Antibacterial Activities of a Novel Glycylcycline, the 9-t-Butylglycylamido Derivative of Minocycline (GAR-936)," *Antimicrobial Agents and Chemotherapy*, vol. 43(4):738-744 (1999).

Spencer, John L. et al, "6-Deoxytetracyclines. V.[1a] 7,9-Disubstituted Products," *J. Med. Chem.*, vol. 6:405-407 (1963).

Sum, Phaik-Eng et al, "Glycylcyclines. 1. A New Generation of Potent Antibacterial Agents through Modification of 9-Aminotetracyclines," *J. Med. Chem.*, vol. 37:184-188 (1994).

Sum, Phaik-Eng et al, "Synthesis and Structure-Activity Relationship of Novel Glycylcycline Derivatives Leading to the Discovery of GAR-936," *Bioorganic & Medicinal Chemistry Letters*, vol. 9:1459-1462 (1999).

Tally, F.T. et al, "Glycylcyclines: a new generation of tetracyclines," *Journal of Antimicrobial Chemotherapy*, vol. 35:449-452 (1995).

International Search Report for Application No. PCT/US3/07229, dated Oct. 8, 2003.

Supplemental European Search Report for Application No. 0371641637—2123, dated Feb. 23, 2006.

\* cited by examiner

AMINO-METHYL SUBSTITUTED TETRACYCLINE COMPOUNDS

RELATED APPLICATIONS

This application is a continuation application of U.S. Ser. No. 10/384,855, entitled "Amino-Methyl Substituted Tetracycline Compounds," filed Mar. 10, 2003, now abandoned and claims priority to U.S. Provisional Patent Application Ser. No. 60/395,495, entitled "Amino-Methyl Substituted Tetracycline Compounds," filed on Jul. 12, 2002; and U.S. Provisional Patent Application Ser. No. 60/362,654, entitled "9-Amino-Methyl Substituted Minocycline Compounds," filed Mar. 8, 2002. Each of the aforementioned applications are hereby incorporated herein by reference in their entirety.

BACKGROUND OF THE INVENTION

The development of the tetracycline antibiotics was the direct result of a systematic screening of soil specimens collected from many parts of the world for evidence of microorganisms capable of producing bacteriocidal and/or bacteriostatic compositions. The first of these novel compounds was introduced in 1948 under the name chlortetracycline. Two years later, oxytetracycline became available. The elucidation of the chemical structure of these compounds confirmed their similarity and furnished the analytical basis for the production of a third member of this group in 1952, tetracycline. A new family of tetracycline compounds, without the ring-attached methyl group present in earlier tetracyclines, was prepared in 1957 and became publicly available in 1967.

Recently, research efforts have focused on developing new tetracycline antibiotic compositions effective under varying therapeutic conditions and routes of administration. New tetracycline analogues have also been investigated which may prove to be equal to or more effective than the originally introduced tetracycline compounds. Examples include U.S. Pat. Nos. 3,957,980; 3,674,859; 2,980,584; 2,990,331; 3,062,717; 3,557,280; 4,018,889; 4,024,272; 4,126,680; 3,454,697; and 3,165,531. These patents are representative of the range of pharmaceutically active tetracycline and tetracycline analogue compositions.

Historically, soon after their initial development and introduction, the tetracyclines were found to be highly effective pharmacologically against rickettsiae; a number of gram-positive and gram-negative bacteria; and the agents responsible for lymphogranuloma venereum, inclusion conjunctivitis, and psittacosis. Hence, tetracyclines became known as "broad spectrum" antibiotics. With the subsequent establishment of their in vitro antimicrobial activity, effectiveness in experimental infections, and pharmacological properties, the tetracyclines as a class rapidly became widely used for therapeutic purposes. However, this widespread use of tetracyclines for both major and minor illnesses and diseases led directly to the emergence of resistance to these antibiotics even among highly susceptible bacterial species both commensal and pathogenic (e.g., *pneumococci* and *Salmonella*). The rise of tetracycline-resistant organisms has resulted in a general decline in use of tetracyclines and tetracycline analogue compositions as antibiotics of choice.

SUMMARY OF THE INVENTION

In one embodiment, the invention pertains to tetracycline compounds of the formula (I):

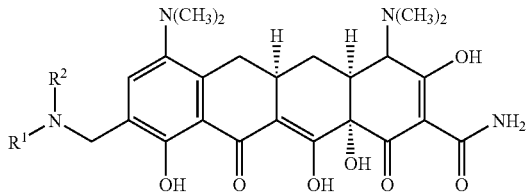

wherein $R^1$ and $R^2$ are linked to form a ring, or pharmaceutically acceptable salts, prodrugs and esters thereof.

The invention also pertains, at least in part, tetracycline compounds of the formula:

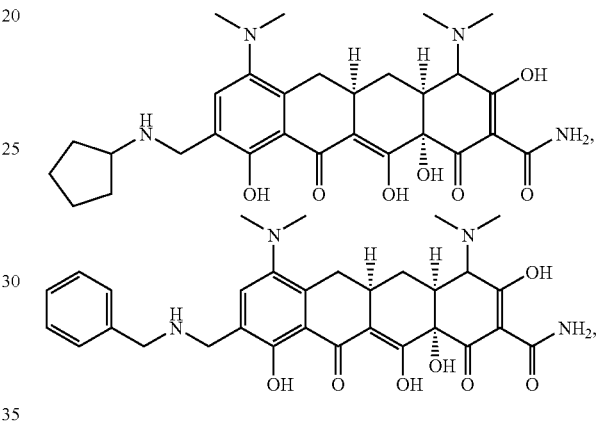

or pharmaceutically accepable salts, esters or prodrugs thereof.

The invention also pertains, at least in part, to tetracycline compounds of the formula (II):

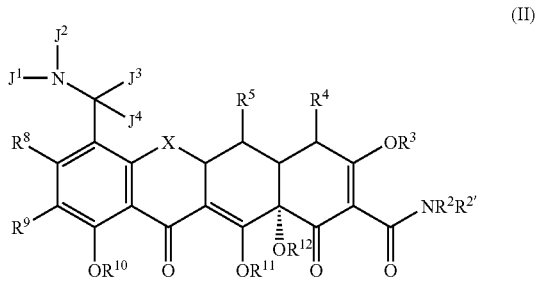

wherein:

$J^1$ and $J^2$ are each independently hydrogen, aryl, sulfonyl, acyl, or linked to form a ring, provided that at least one of $J^1$ or $J^2$ is not hydrogen;

$J^3$ and $J^4$ are each alkyl, halogen, or hydrogen;

X is $CHC(R^{13}Y'Y)$, $CR^6R^6$, $C=CR^6R^6$, S, $NR^6$, or O;

$R^2$, $R^{2'}$, $R^{4'}$, and $R^{4''}$ are each independently hydrogen, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

$R^4$ is $NR^{4'}R^{4''}$, alkyl, alkenyl, alkynyl, aryl, hydroxyl, halogen, or hydrogen;

$R^{2'}$, $R^3$, $R^{10}$, $R^{11}$ and $R^{12}$ are each hydrogen or a pro-drug moiety;

$R^5$ is hydroxyl, hydrogen, thiol, alkanoyl, aroyl, alkaroyl, aryl, heteroaromatic, alkyl, alkenyl, alkynyl, alkoxy, alkylthio, alkylsulfinyl, alkylsulfonyl, alkylamino, arylalkyl, alkyl carbonyloxy, or aryl carbonyloxy;

$R^6$ and $R^{6'}$ are each independently hydrogen, methylene, absent, hydroxyl, halogen, thiol, alkyl, alkenyl, alkynyl, aryl, alkoxy, alkylthio, alkylsulfinyl, alkylsulfonyl, alkylamino, or an arylalkyl;

$R^9$ is hydrogen, nitro, alkyl, alkenyl, alkynyl, aryl, alkoxy, alkylthio, alkylsulfinyl, alkylsulfonyl, arylalkyl, amino, arylalkenyl, arylalkynyl, thionitroso, or $-(CH_2)_{0-3}NR^{9c}C(=Z')ZR^{9a}$;

Z is $CR^{9d}R^{9e}$, S, $NR^{9b}$ or O;

Z' is O, S, or $NR^{9f}$;

$R^{9a}$, $R^{9b}$, $R^{9c}$, $R^{9d}$, and $R^{9e}$ are each independently hydrogen, acyl, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

$R^8$ is hydrogen, hydroxyl, halogen, thiol, alkyl, alkenyl, alkynyl, aryl, alkoxy, alkylthio, alkylsulfinyl, alkylsulfonyl, alkylamino, or an arylalkyl;

$R^{13}$ is hydrogen, hydroxy, alkyl, alkenyl, alkynyl, alkoxy, alkylthio, alkylsulfinyl, alkylsulfonyl, alkylamino, or an arylalkyl; and Y' and Y are each independently hydrogen, halogen, hydroxyl, cyano, sulfhydryl, amino, alkyl, alkenyl, alkynyl, alkoxy, alkylthio, alkylsulfinyl, alkylsulfonyl, alkylamino, or an arylalkyl, and pharmaceutically acceptable salts, esters, and prodrugs thereof.

The invention also pertains, at least in part, to tetracycline compounds of formula (III):

(III)

wherein:

$J^5$ and $J^6$ are each independently hydrogen, alkyl, alkenyl, alkynyl, aryl, sulfonyl, acyl, alkoxycarbonyl, alkaminocarbonyl, alkaminothiocarbonyl, substituted thiocarbonyl, substituted carbonyl, alkoxythiocarbonyl, or linked to form a ring;

$J^7$ and $J^8$ are each alkyl, halogen, or hydrogen;

X is $CHC(R_{13}Y'Y)$, $CR^{6'}R^6$, $C=CR^{6'}R^6$, S, $NP^6$, or O;

$R^2$, $R^{2'}$, $R^{4'}$, and $R^{4''}$ are each independently hydrogen, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

$R^4$ is $NR^{4'}R^{4''}$, alkyl, alkenyl, alkynyl, aryl, hydroxyl, halogen, or hydrogen;

$R^{2'}$, $R^3$, $R^{10}$, $R^{11}$ and $R^{12}$ are each hydrogen or a pro-drug moiety;

$R^5$ is hydroxyl, hydrogen, thiol, alkanoyl, aroyl, alkaroyl, aryl, heteroaromatic, alkyl, alkenyl, alkynyl, alkoxy, alkylthio, alkylsulfinyl, alkylsulfonyl, alkylamino, arylalkyl, alkyl carbonyloxy, or aryl carbonyloxy;

$R^6$ and $R^{6'}$ are each independently hydrogen, methylene, absent, hydroxyl, halogen, thiol, alkyl, alkenyl, alkynyl, aryl, alkoxy, alkylthio, alkylsulfinyl, alkylsulfonyl, alkylamino, or an arylalkyl;

$R^7$ is hydrogen, nitro, alkyl, alkenyl, alkynyl, aryl, alkoxy, alkylthio, alkylsulfinyl, alkylsulfonyl, arylalkyl, amino, arylalkenyl, arylalkynyl, thionitroso, or $-(CH_2)_{0-3}NR^{7c}C(=W')WR^{7a}$;

W is $CR^{7d}R^{7e}$, S, $NR^{7b}$ or O;

W' is O, S, or $NR^{7f}$;

$R^{7a}$, $R^{7b}$, $R^{7c}$, $R^{7d}$ and $R^{7e}$ are each independently hydrogen, acyl, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

$R^8$ is hydrogen, hydroxyl, halogen, thiol, alkyl, alkenyl, alkynyl, aryl, alkoxy, alkylthio, alkylsulfinyl, alkylsulfonyl, alkylamino, or an arylalkyl;

$R^{13}$ is hydrogen, hydroxy, alkyl, alkenyl, alkynyl, alkoxy, alkylthio, alkylsulfinyl, alkylsulfonyl, alkylamino, or an arylalkyl; and Y' and Y are each independently hydrogen, halogen, hydroxyl, cyano, sulihydryl, amino, alkyl, alkenyl, alkynyl, alkoxy, alkylthio, alkylsulfinyl, alkylsulfonyl, alkylamino, or an arylalkyl, and pharmaceutically acceptable salts thereof.

The invention also pertains to compounds of the formulae shown in Table 1 and pharmaceutically acceptable esters, salts, and prodrugs thereof.

The invention also pertains, at least in part, to pharmaceutical compositions comprising aminomethyl tetracycline compounds of formulae (I), (II), (III), Table 1, or otherwise described herein. The pharmaceutical compositions preferably comprise an effective amount of a minocycline compound and a pharmaceutically acceptable carrier.

In another embodiment, the invention also pertains, at least in part, to methods of using the aminomethyl tetracycline compounds of the invention (e.g., of formula (I), (III), (III), Table 1, or otherwise described herein), to treat tetracycline associated states in subjects.

In an embodiment, the invention pertains, at least in part, to a method for the synthesis of an aminoalkyl tetracycline compound. The method includes contacting a tetracycline compound with an aminoalkylating reagent under appropriate conditions, such that an aminoalkyl tetracycline compound is formed.

In another embodiment, the invention pertains to pharmaceutical compositions containing the aminoalkyltetracycline compounds of the invention and aminoalkyltetracycline compounds synthesized by the methods of the invention.

DETAILED DESCRIPTION OF THE INVENTION

In an embodiment, the invention pertains to tetracycline compounds of the formula (I):

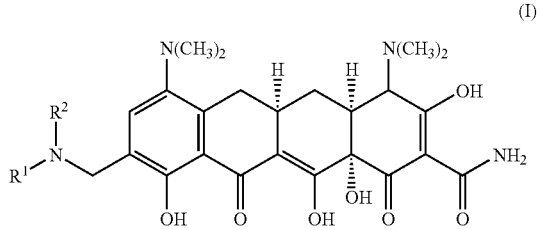

(I)

wherein $R^1$ and $R^2$ are linked to form a ring, or pharmaceutically acceptable salts, prodrugs and esters thereof.

In one embodiment, $R^1$ and $R^2$ are linked to form a five or six membered ring. In another, $R^1$ and $R^2$ are linked to form a six membered ring. $R^1$ and $R^2$ may be linked by a chain of atoms such as, for example, —$(CH_2)_{5-6}$—, —$(CH_2)_{1-5}$—CH=CH—$(CH_2)_{1-5}$—, —$(CH_2)_{1-5}$—O—$(CH_2)_{1-5}$—, —$(CH_2)_{1-5}$—NR—$(CH_2)_{1-5}$, etc. The ring formed may be saturated or unsaturated. For example, $R^1$ and $R^2$ may be linked to form a piperdine ring, morpholine ring, pyridine ring, or a pyrazinyl ring.

In a further embodiment, the tetracycline compound is:

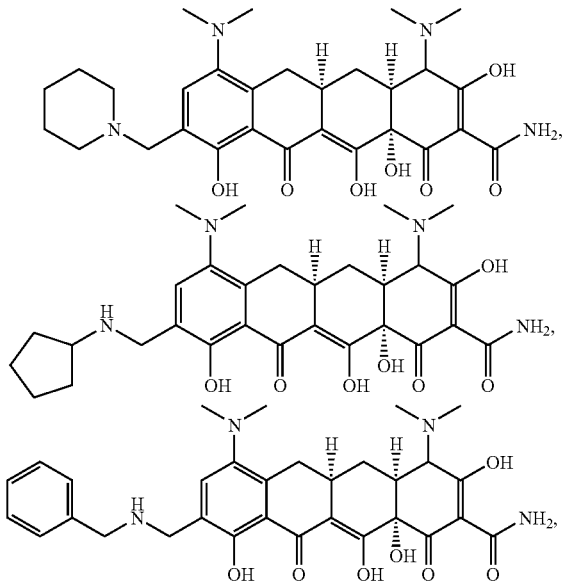

or pharmaceutically accepable salts, esters or prodrugs thereof.

In one embodiment, the invention pertains to aminomethyl tetracycline compounds of the formula (II):

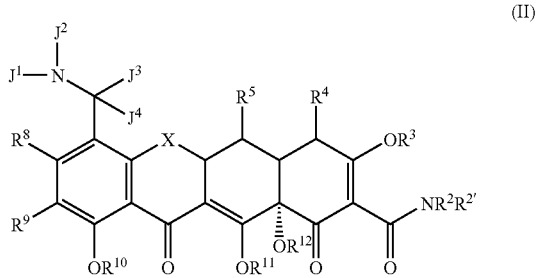

wherein:
$J^1$ and $J^2$ are each independently hydrogen, aryl, sulfonyl, acyl, or linked to form a ring, provided that at least one of $J^1$ or $J^2$ is not hydrogen;

$J^3$ and $J^4$ are each alkyl, halogen, or hydrogen;

X is $CHC(R^{13}Y'Y)$, $CR^{6'}R^6$, $C=CR^{6'}R^6$, S, $NR^6$, or O;

$R^2$, $R^{2'}$, $R^{4'}$, and $R^{4''}$ are each independently hydrogen, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

$R^4$ is $NR^{4'}R^{4''}$, alkyl, alkenyl, alkynyl, aryl, hydroxyl, halogen, or hydrogen;

$R^{2'}$, $R^3$, $R^{10}$, $R^{11}$ and $R^{12}$ are each hydrogen or a pro-drug moiety;

$R^5$ is hydroxyl, hydrogen, thiol, alkanoyl, aroyl, alkaroyl, aryl, heteroaromatic, alkyl, alkenyl, alkynyl, alkoxy, alkylthio, alkylsulfinyl, alkylsulfonyl, alkylamino, arylalkyl, alkyl carbonyloxy, or aryl carbonyloxy;

$R^6$ and $R^{6'}$ are each independently hydrogen, methylene, absent, hydroxyl, halogen, thiol, alkyl, alkenyl, alkynyl, aryl, alkoxy, alkylthio, alkylsulfinyl, alkylsulfonyl, alkylamino, or an arylalkyl;

$R^9$ is hydrogen, nitro, alkyl, alkenyl, alkynyl, aryl, alkoxy, alkylthio, alkylsulfinyl, alkylsulfonyl, arylalkyl, amino, arylalkenyl, arylalkynyl, thionitroso, or —$(CH_2)_{0-3}NR^{9c}C(=Z')ZR^{9a}$;

Z is $CR^{9d}R^{9e}$, S, $NR^{9b}$ or O;

Z' is O, S, or $NR^{9f}$;

$R^{9a}$, $R^{9b}$, $R^{9c}$, $R^{9d}$, and $R^{9e}$ are each independently hydrogen, acyl, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

$R^8$ is hydrogen, hydroxyl, halogen, thiol, alkyl, alkenyl, alkynyl, aryl, alkoxy, alkylthio, alkylsulfinyl, alkylsulfonyl, alkylamino, or an arylalkyl;

$R^{13}$ is hydrogen, hydroxy, alkyl, alkenyl, alkynyl, alkoxy, alkylthio, alkylsulfinyl, alkylsulfonyl, alkylamino, or an arylalkyl; and Y' and Y are each independently hydrogen, halogen, hydroxyl, cyano, sulfhydryl, amino, alkyl, alkenyl, alkynyl, alkoxy, alkylthio, alkylsulfinyl, alkylsulfonyl, alkylamino, or an arylalkyl, and pharmaceutically acceptable salts, esters, and prodrugs thereof.

In an embodiment, the tetracycline compound is a oxytetracycline compound (e.g., wherein $R^4$ is $NR^{4'}R^{4''}$, $R^{4'}$ and $R^{4''}$ are each methyl, $R^5$ is OH, X is $CR^6R^{6'}$, $R^6$ is OH, and $R^{6'}$ is $CH_3$). In another embodiment, the aminoalkyl tetracycline compound is a demeclocycline compound (e.g., wherein $R^4$ is $NR^{4'}R^{4''}$, $R^{4'}$ and $R^{4''}$ are each methyl, $R^5$ is hydrogen, X is $CR^6R^{6'}$, $R^6$ is OH, $R^{6'}$ is hydrogen, and $R^7$ is chlorine). In another embodiment, the aminoalkyl tetracycline compound is a methacycline compound (e.g., wherein $R^4$ is $NR^{4'}R^{4''}$, $R^{4'}$ and $R^{4''}$ are each methyl, $R^5$ is OH, X is $CR^6R^{6'}$, $R^6$ and $R^{6'}$ are, taken together, $CH_2$). In another embodiment, the aminoalkyl tetracycline compound is a doxycycline compound (e.g., wherein $R^4$ is $NR^{4'}R^{4''}$, $R^{4'}$ and $R^{4''}$ are each methyl, $R^5$ is OH, X is $CR^6R^{6'}$, $R^6$ is OH, and $R^{6'}$ is $CH_3$). In another embodiment, the aminoalkyl tetracycline compound is a chlorotetracycline compound (e.g., wherein $R^4$ is $NR^{4'}R^{4''}$, $R^{4'}$ and $R^{4''}$ are each methyl, $R^5$ is hydrogen, X is $CR^6R^{6'}$, $R^6$ is OH, $R^{6'}$ is $CH_3$, and $R^7$ is chlorine). In another embodiment, the aminoalkyl tetracycline compound is a tetracycline compound (e.g., wherein $R^4$ is $NR^{4'}R^{4''}$, $R^{4'}$ and $R^{4''}$ are each methyl, $R^5$ is hydrogen, X is $CR^6R^{6'}$, $R^6$ and $R^{6'}$ are each hydrogen and $R^7$ is $N(CH_3)_2$). In a further embodiment, $R^5$ of formula I is a protected hydroxyl group, e.g. a prodrug moiety. Examples of prodrug moieties include, for example, acyl esters and esters. In certain embodiments, the prodrug moiety is aroyl, alkanoyl, or alkaroyl and may or may not be cleaved in vivo to the hydroxyl group. In certain embodiments, $R^4$ is hydrogen.

In an embodiment, $J^3$ and $J^4$ are hydrogen. In another embodiment, $J^1$ may be substituted or unsubstituted alkyl. $J^1$ also may be sulfonyl or $J^1$ and $J^2$ may be linked to form a ring. In a further embodiment, $J^1$ maybe heteroaryl or substituted carbonyl.

Examples of aminoalkyltetracycline compounds synthesized by methods of the invention include, but are not limited to, compounds of the following formulae:
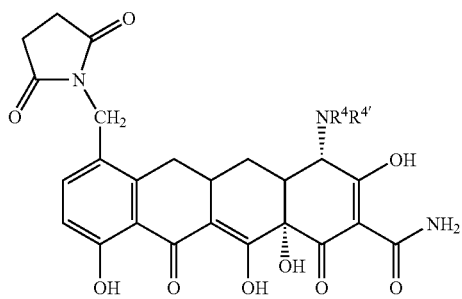
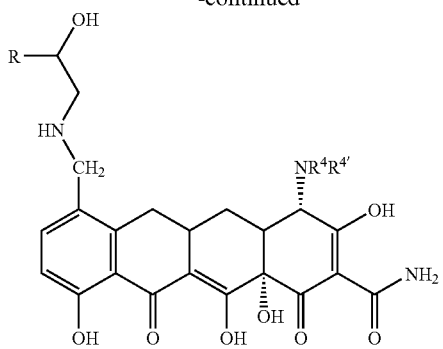
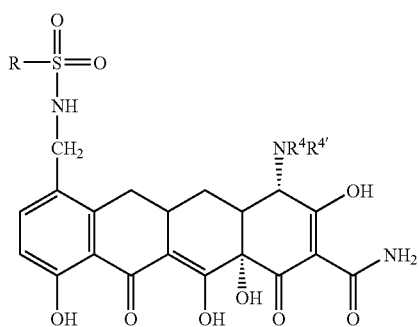
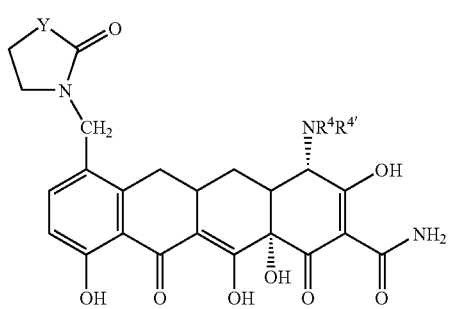
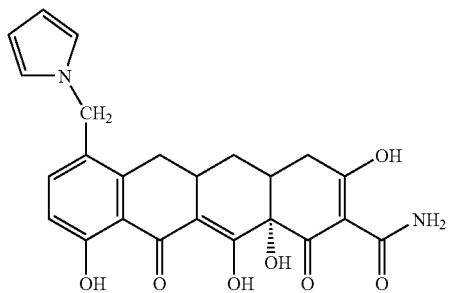
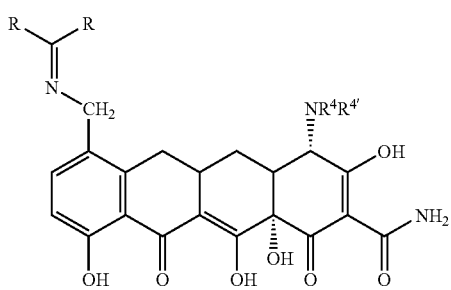
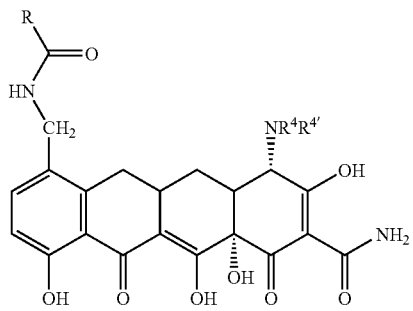
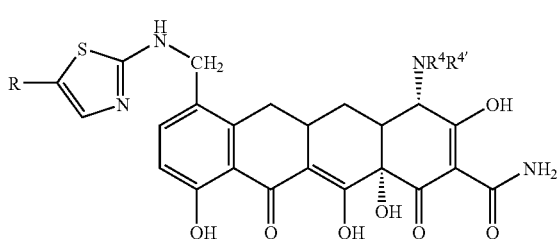
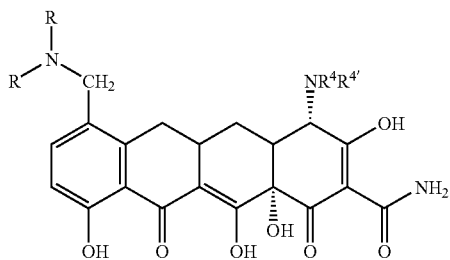
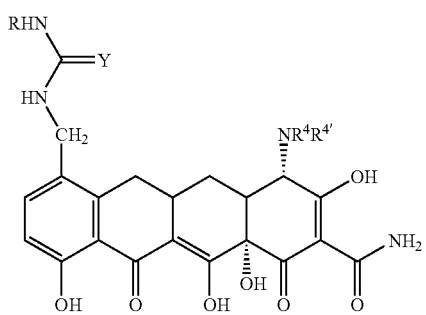

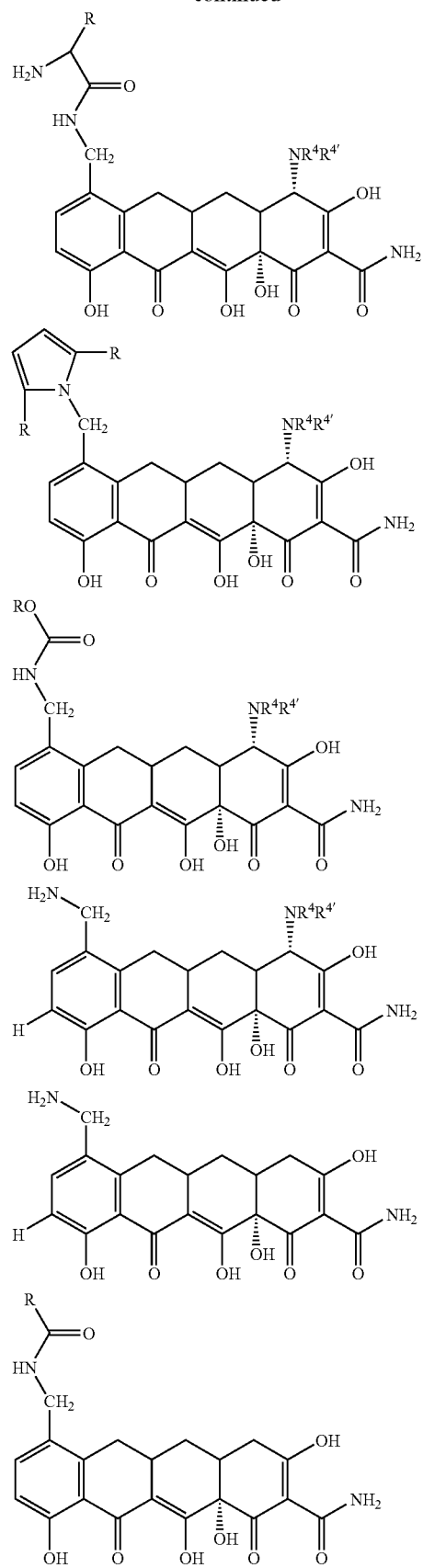
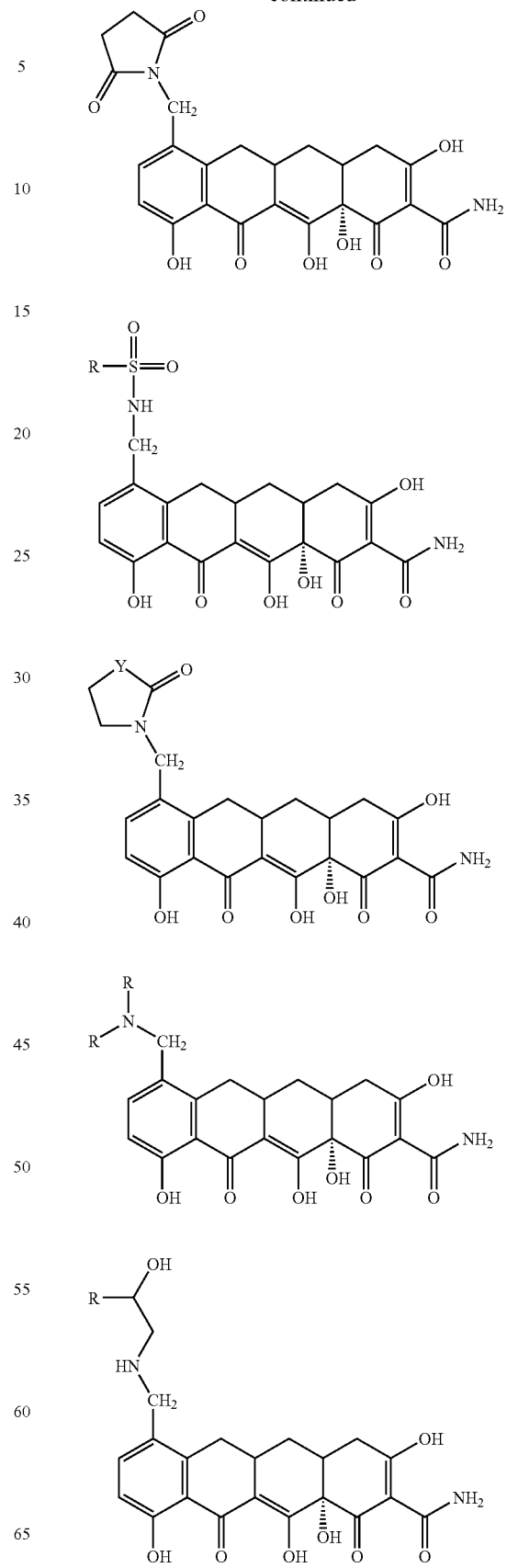

-continued

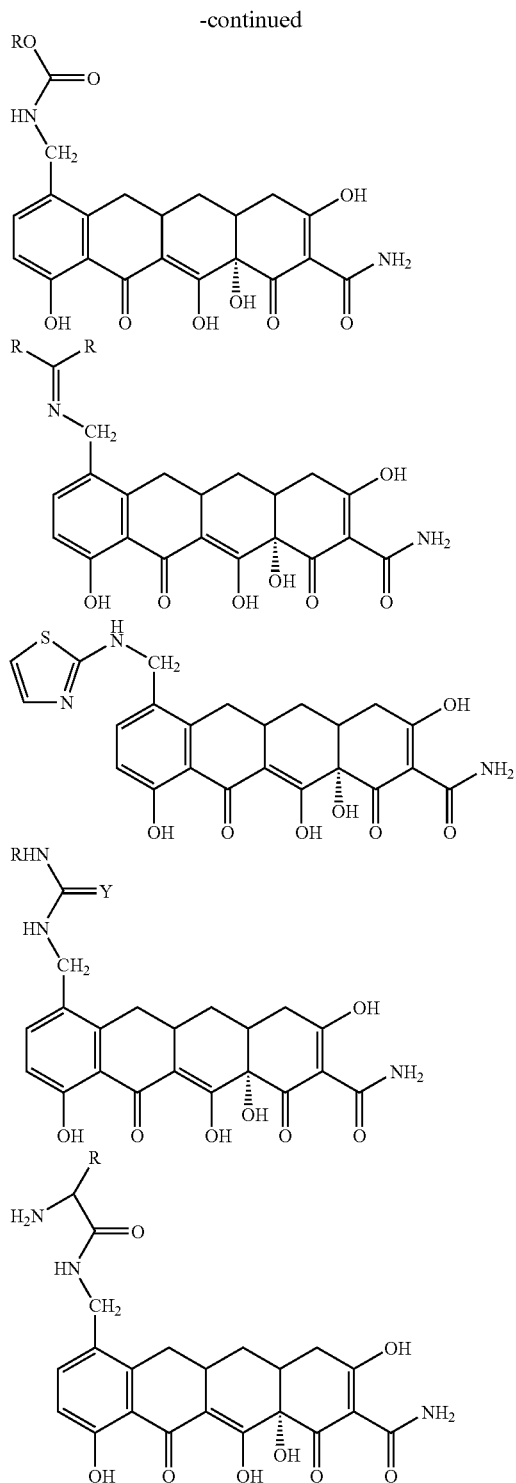

wherein
R is substituted or unsubstituted alkyl, alkenyl, alkyyl, halogen, alkoxy; and
Y is N, O, or S, or pharmaceutically acceptable salts or prodrugs thereof.

In another embodiment, the aminoalkyl tetracycline compound of the invention may be a compound of the formula (II):

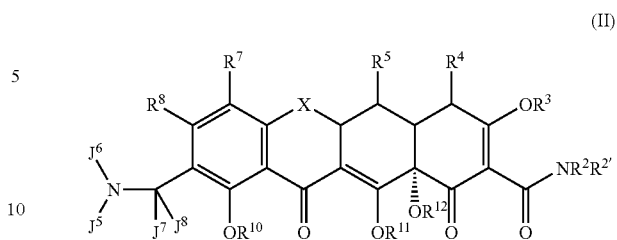

wherein:
$J^5$ and $J^6$ are each independently hydrogen, alkyl, alkenyl, alkynyl, aryl, sulfonyl, acyl, alkoxycarbonyl, alkaminocarbonyl, alkaminothiocarbonyl, substituted thiocarbonyl, substituted carbonyl, alkoxythiocarbonyl, or linked to form a ring;
$J^7$ and $J^8$ are each alkyl, halogen, or hydrogen;
X is $CHC(R^{13}Y'Y)$, $CR^6R^6$, $C=CR^{6'}R^6$, S, $NR^6$, or O;
$R^2$, $R^{2'}$, $R^{4'}$, and $R^{4''}$ are each independently hydrogen, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;
$R^4$ is $NR^{4'}R^{4''}$, alkyl, alkenyl, alkynyl, aryl, hydroxyl, halogen, or hydrogen;
$R^{2'}$, $R^3$, $R^{10}$, $R^{11}$ and $R^{12}$ are each hydrogen or a pro-drug moiety;
$R^5$ is hydroxyl, hydrogen, thiol, alkanoyl, aroyl, alkaroyl, aryl, heteroaromatic, alkyl, alkenyl, alkynyl, alkoxy, alkylthio, alkylsulfinyl, alkylsulfonyl, alkylamino, arylalkyl, alkyl carbonyloxy, or aryl carbonyloxy;
$R^6$ and $R^{6'}$ are each independently hydrogen, methylene, absent, hydroxyl, halogen, thiol, alkyl, alkenyl, alkynyl, aryl, alkoxy, alkylthio, alkylsulfinyl, alkylsulfonyl, alkylamino, or an arylalkyl;
$R^7$ is hydrogen, nitro, alkyl, alkenyl, alkynyl, aryl, alkoxy, alkylthio, alkylsulfinyl, alkylsulfonyl, arylalkyl, amino, arylalkenyl, arylalkynyl, thionitroso, or $-(CH_2)_{0-3}NR^{7c}C(=W')WR^{7a}$;
W is $CR^{7d}R^{7e}$, S, $NR^{7b}$ or O; W' is O, S, or $NR^{7f}$;
$R^{7a}$, $R^{7b}$, $R^{7c}$, $R^{7d}$, and $R^{7e}$ are each independently hydrogen, acyl, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;
$R^8$ is hydrogen, hydroxyl, halogen, thiol, alkyl, alkenyl, alkynyl, aryl, alkoxy, alkylthio, alkylsulfinyl, alkylsulfonyl, alkylamino, or an arylalkyl;
$R^{13}$ is hydrogen, hydroxy, alkyl, alkenyl, alkynyl, alkoxy, alkylthio, alkylsulfinyl, alkylsulfonyl, alkylamino, or an arylalkyl; and
Y' and Y are each independently hydrogen, halogen, hydroxyl, cyano, sulihydryl, amino, alkyl, alkenyl, alkynyl, alkoxy, alkylthio, alkylsulfinyl, alkylsulfonyl, alkylamino, or an arylalkyl, and pharmaceutically acceptable salts thereof.

In an embodiment, the tetracycline compound is a oxytetracycline compound (e.g., wherein $R^4$ is $NR^{4'}R^{4''}$, $R^{4'}$ and $R^{4''}$ are each methyl, $R^5$ is OH, X is $CR^6R^{6'}$, $R^6$ is OH, and $R^{6'}$ is $CH_3$). In another embodiment, the aminoalkyl tetracycline compound is a demeclocycline compound (e.g., wherein $R^4$ is $NR^{4'}R^{4''}$, $R^{4'}$ and $R^{4''}$ are each methyl, $R^5$ is hydrogen, X is $CR^6R^{6'}$, $R^6$ is OH, $R^{6'}$ is hydrogen, and $R^7$ is chlorine). In another embodiment, the aminoalkyl tetracycline compound is a methacycline compound (e.g., wherein $R^4$ is $NR^{4'}R^{4''}$, $R^{4'}$ and $R^{4''}$ are each methyl, $R^5$ is OH, X is CR$^6$R$^{6'}$, R$^6$ and R$^{6'}$ are, taken together, CH$_2$). In another embodiment, the aminoalkyl tetracycline compound is a doxycycline compound (e.g., wherein R$^4$ is NR$^{4'}$R$^{4''}$, R$^{4'}$ and R$^{4''}$ are each methyl, R$^5$ is OH, X is CR$^6$R$^{6'}$, R$^6$ is OH, and R$^{6'}$ is CH$_3$). In another embodiment, the aminoalkyl tetracycline compound is a chlorotetracycline compound (e.g., wherein R$^4$ is NR$^{4'}$R$^{4''}$, R$^{4'}$ and R$^{4''}$ are each methyl, R$^5$ is hydrogen, X is CR$^6$R$^{6'}$, R$^6$ is OH, R$^{6'}$ is CH$_3$, and R$^7$ is chlorine). In another embodiment, the aminoalkyl tetracycline compound is a tetracycline compound (e.g., wherein R$^4$ is NR$^{4'}$R$^{4''}$, R$^{4'}$ and R$^{4''}$ are each methyl, R$^5$ is hydrogen, X is CR$^6$R$^{6'}$, R$^6$ and R$^{6'}$ are each hydrogen and R$^7$ is N(CH$_3$)$_2$). In a further embodiment, R$^5$ of formula I is a protected hydroxyl group, e.g. a prodrug moiety. Examples of prodrug moieties include, for example, acyl esters and esters. In certain embodiments, the prodrug moiety is aroyl, alkanoyl, or alkaroyl and may or may not be cleaved in vivo to the hydroxyl group. In certain embodiments, R$^4$ is hydrogen.

In an embodiment, J$^7$ and J$^8$ are hydrogen. In another embodiment, J$^5$ may be substituted or unsubstituted alkyl. J$^5$ also may be sulfonyl or J$^5$ and J$^6$ may be linked to form a ring. In a further embodiment, J$^5$ maybe heteroaryl or substituted carbonyl.

Examples of aminoalkyltetracycline compounds synthesized by methods of the invention include, but are not limited to, compounds of the following formulae:

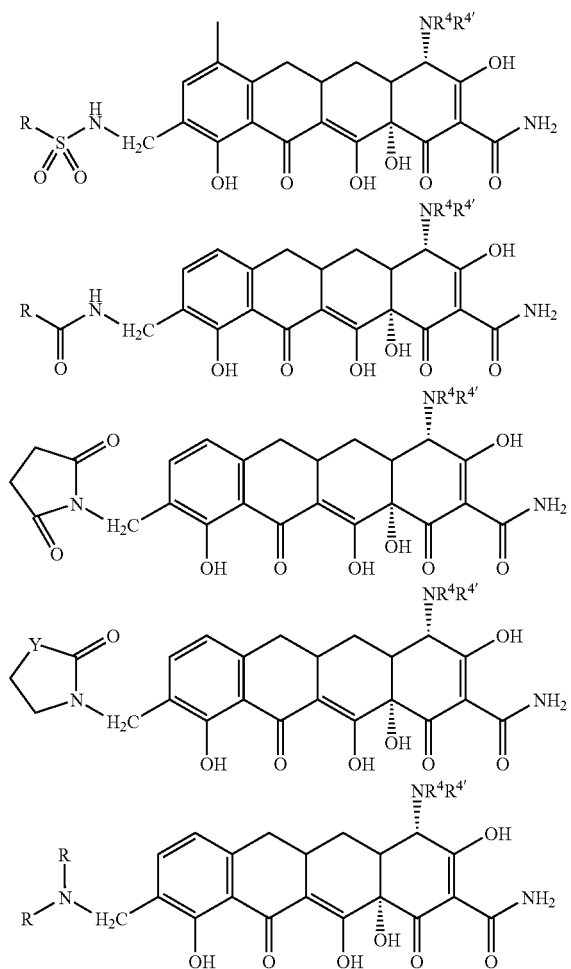

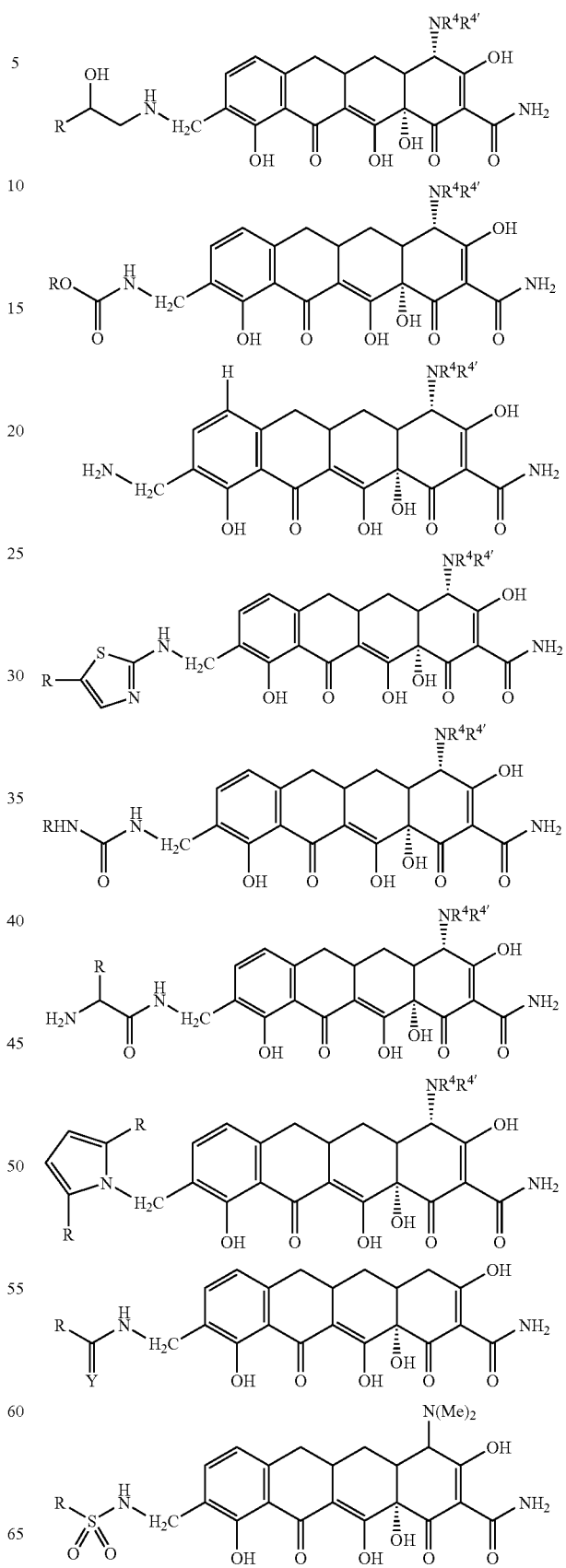

-continued
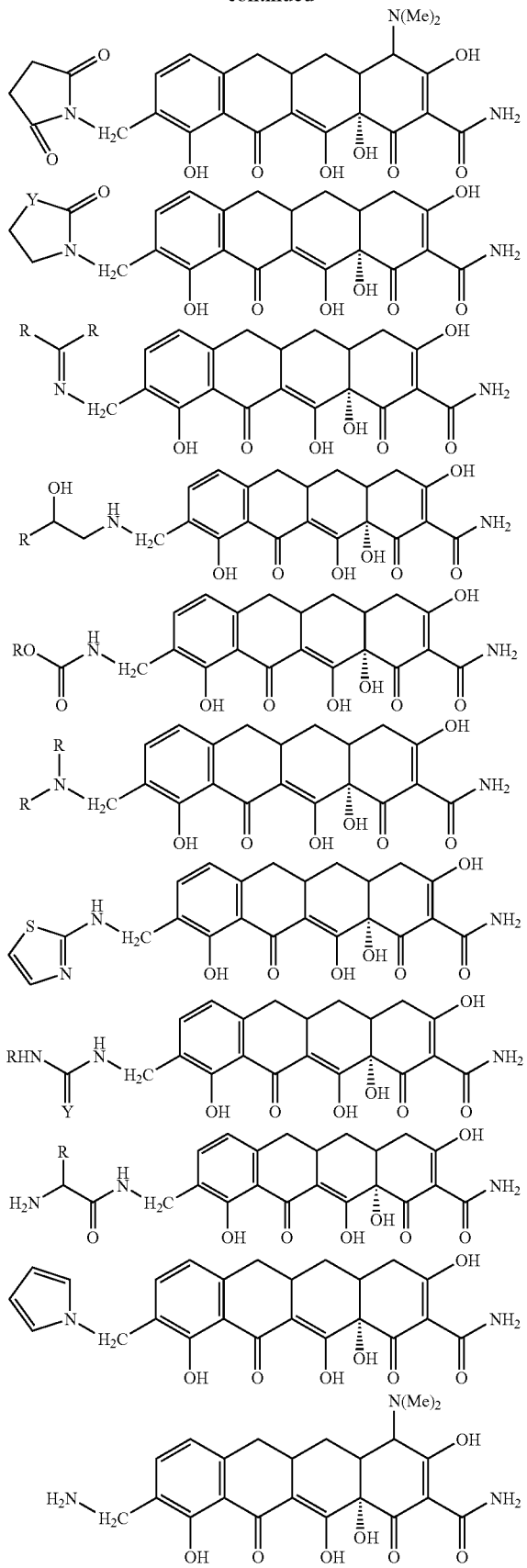
-continued
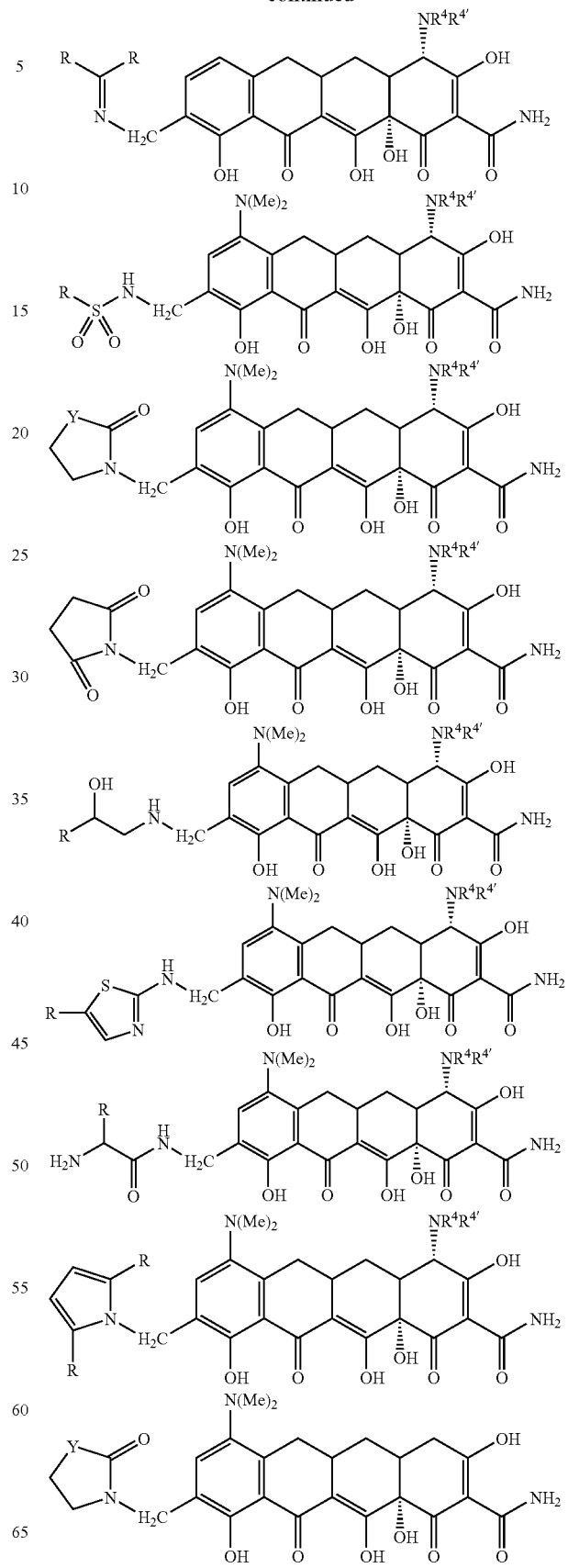

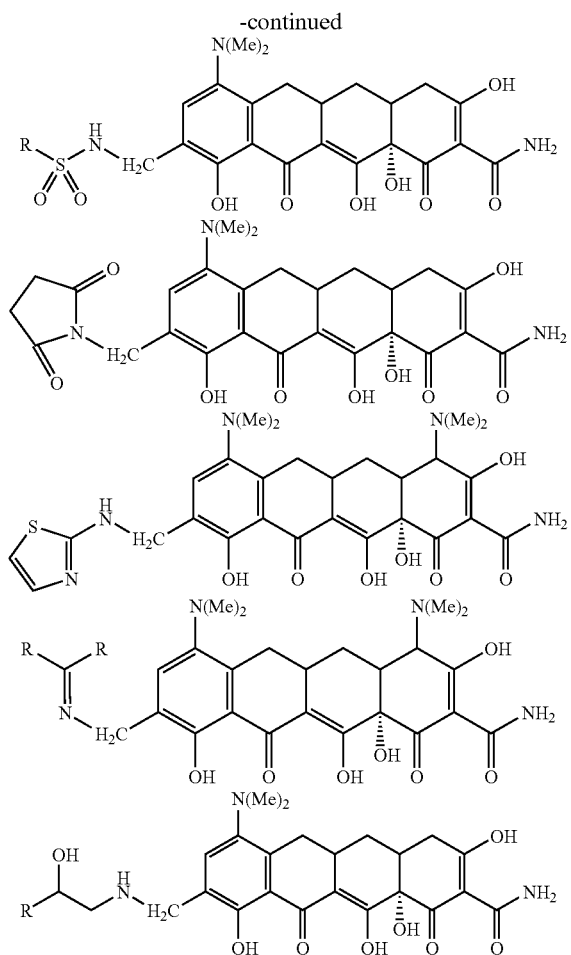
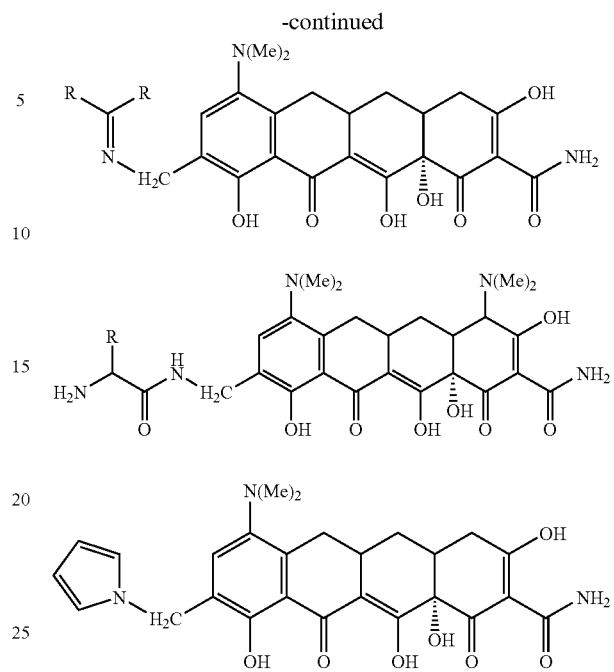
wherein
R is substituted or unsubstituted alkyl, alkenyl, alkynyl, halogen, alkoxy; and
Y is N, O, or S, or pharmaceutically acceptable salts or prodrugs thereof.
Other aminoalkyl tetracycline compounds of the invention are shown in Table 1. The invention includes pharmaceutically acceptable esters, salts, and prodrugs of the compounds shown in Table 1.
TABLE 1
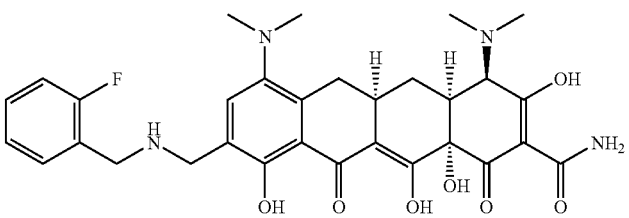
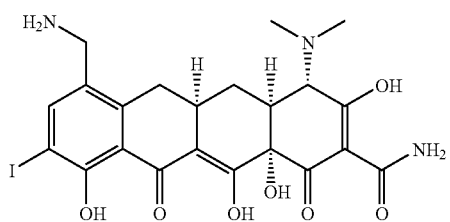

TABLE 1-continued
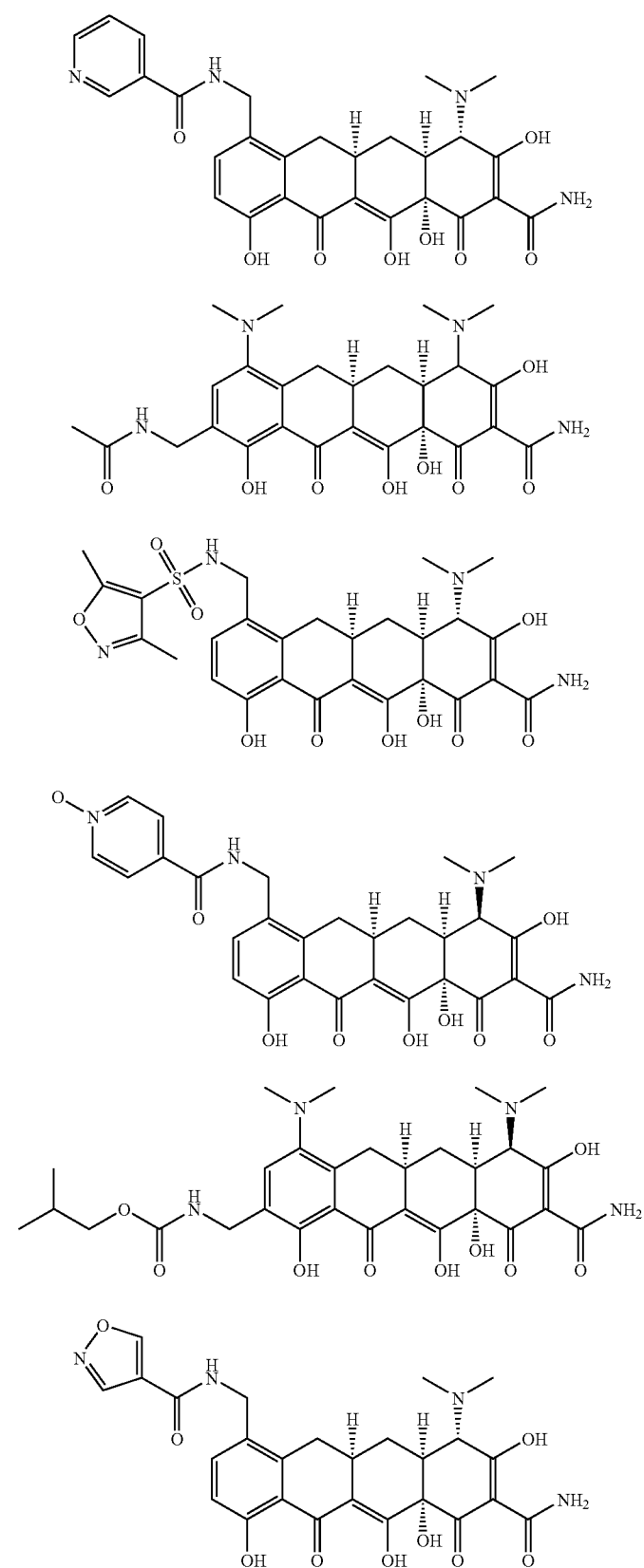

TABLE 1-continued
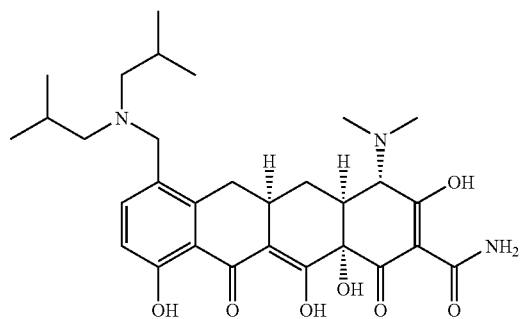
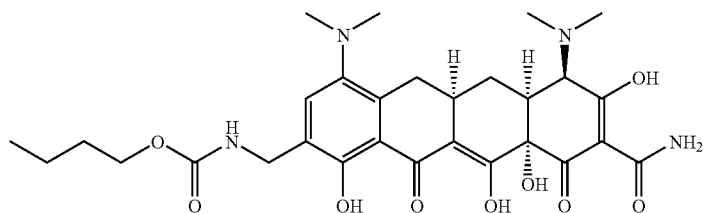
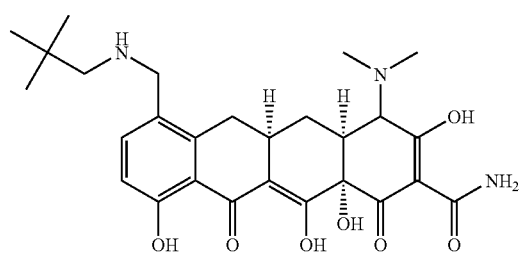
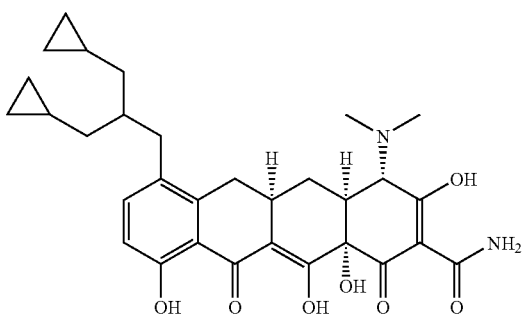
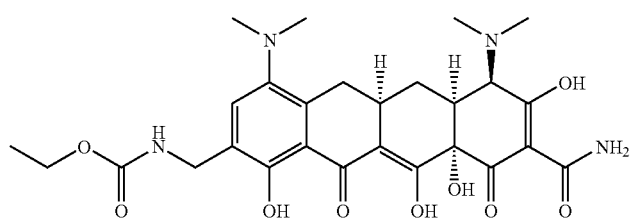

TABLE 1-continued
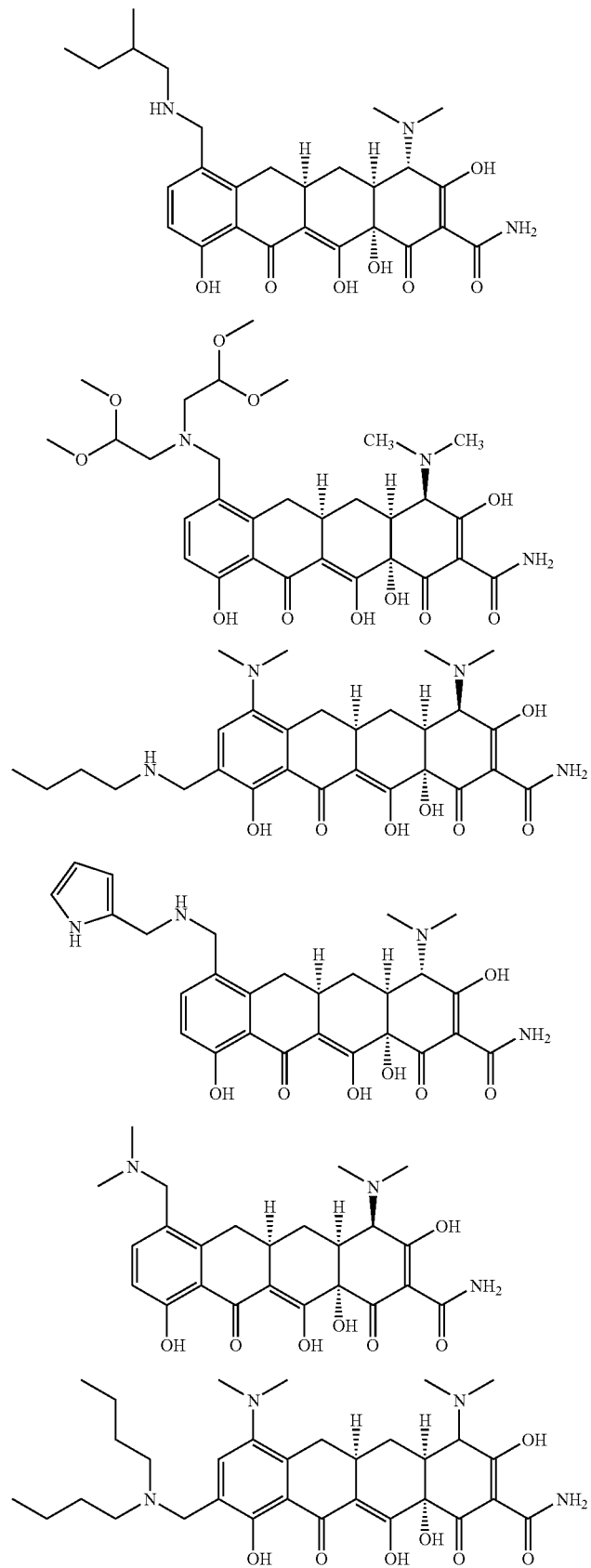

TABLE 1-continued
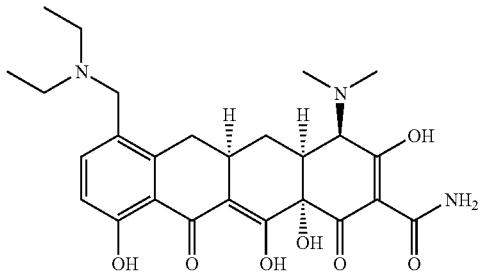
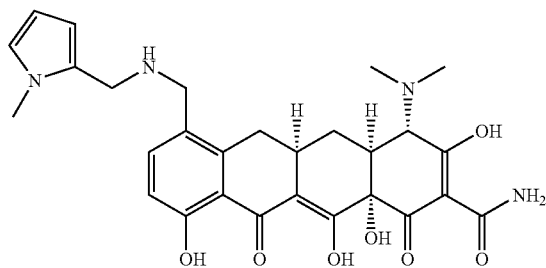
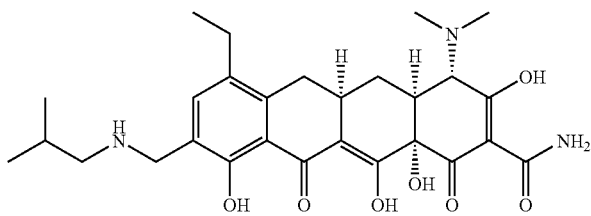
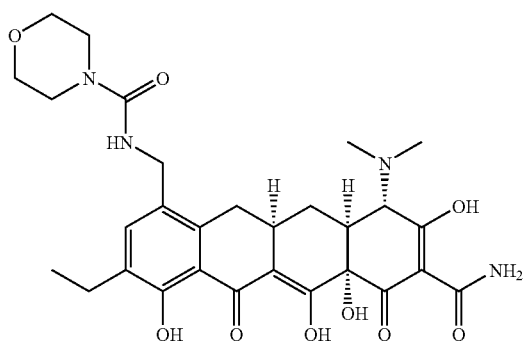
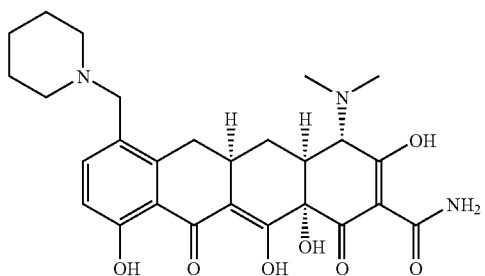

TABLE 1-continued
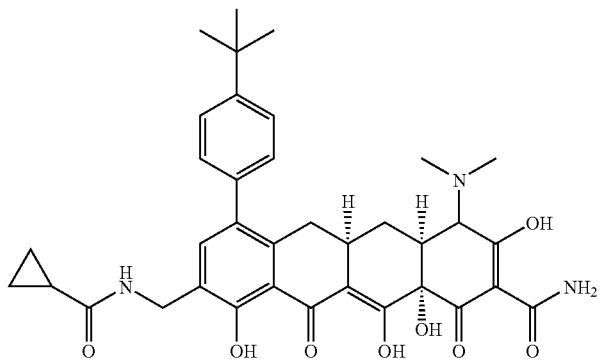
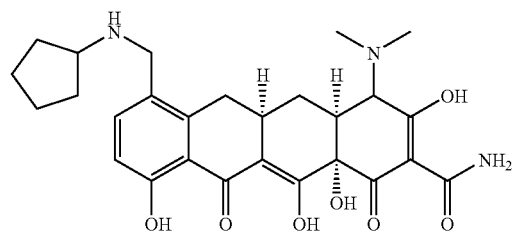
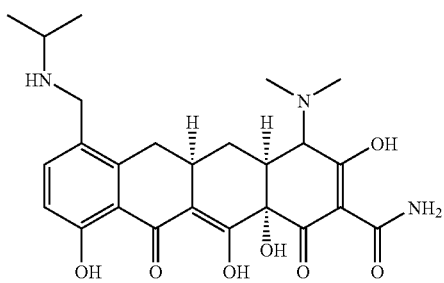
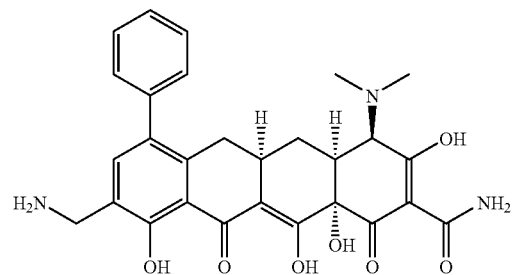
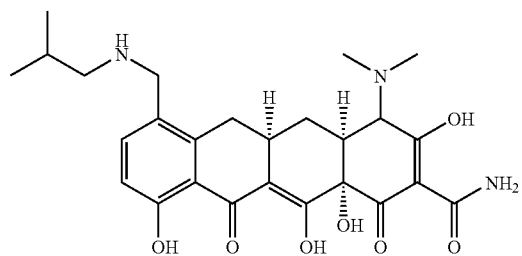

TABLE 1-continued
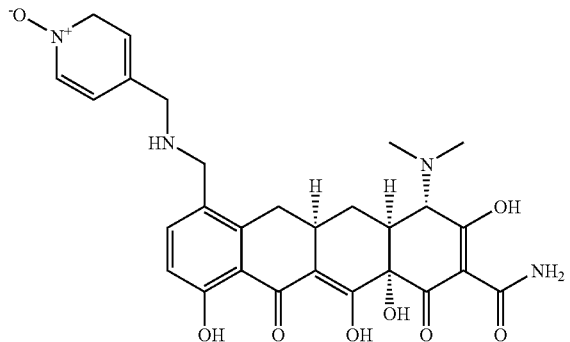
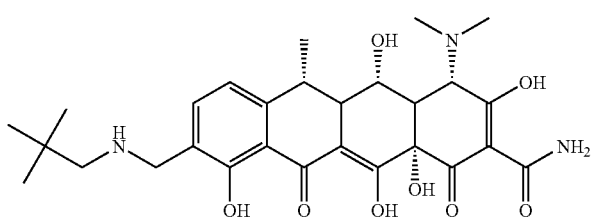
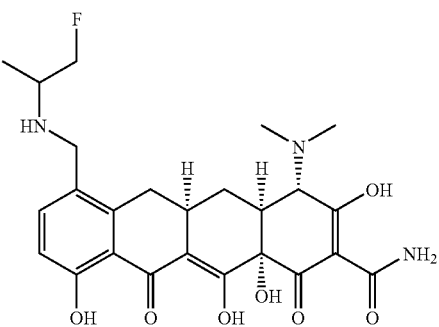
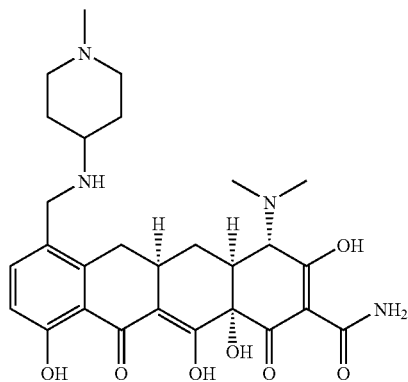
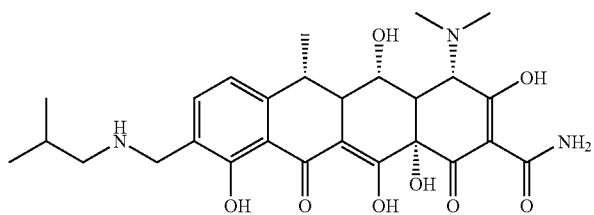

TABLE 1-continued
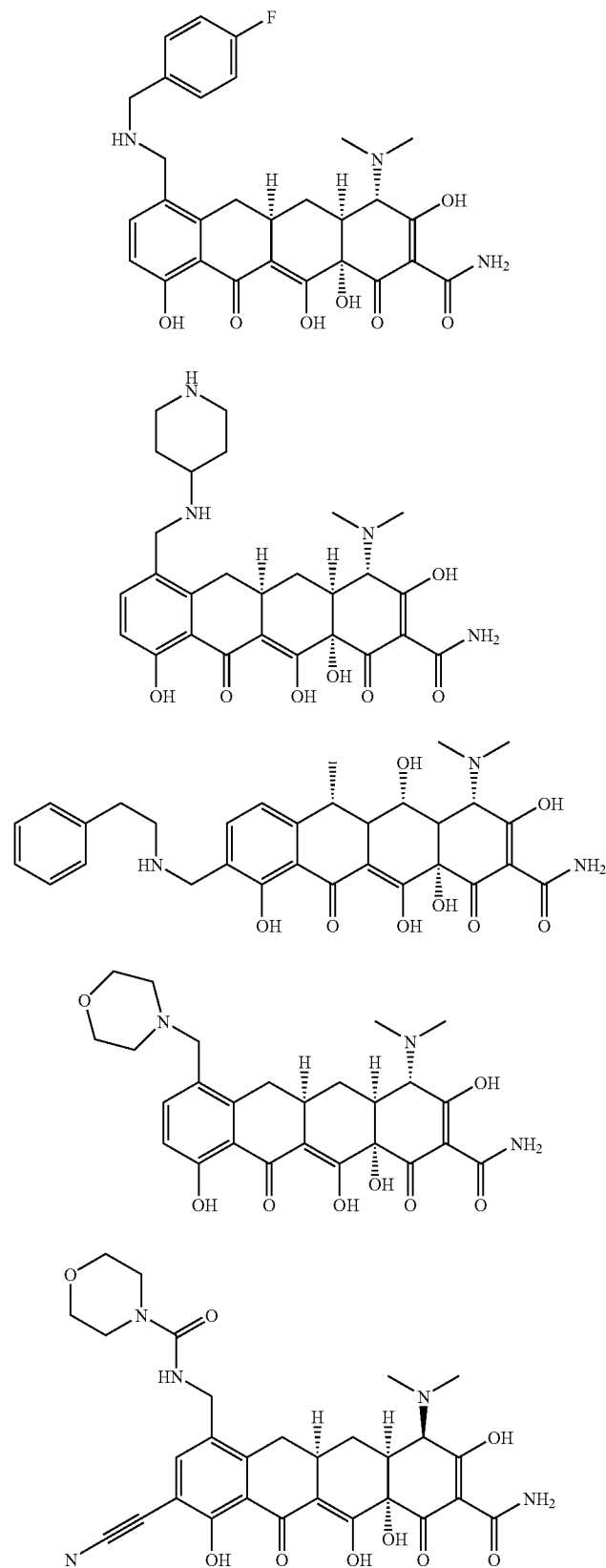

TABLE 1-continued
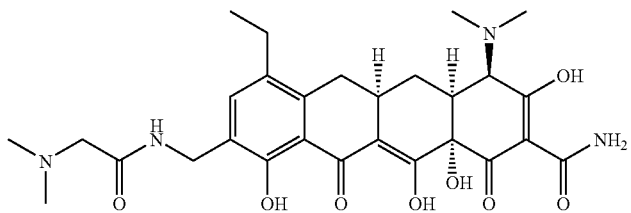
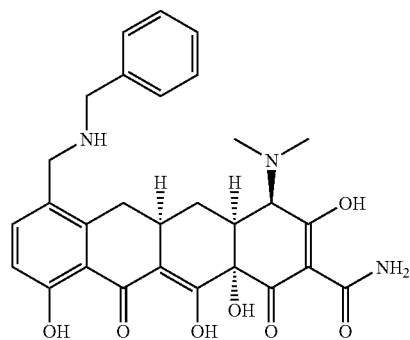
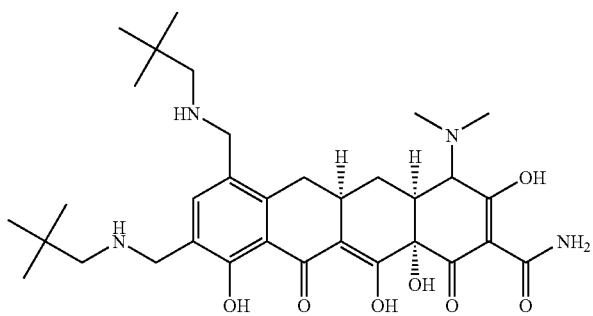
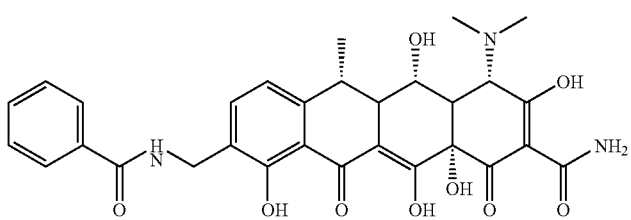
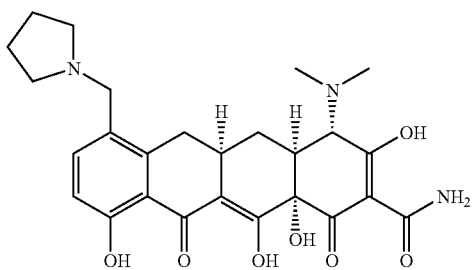

TABLE 1-continued
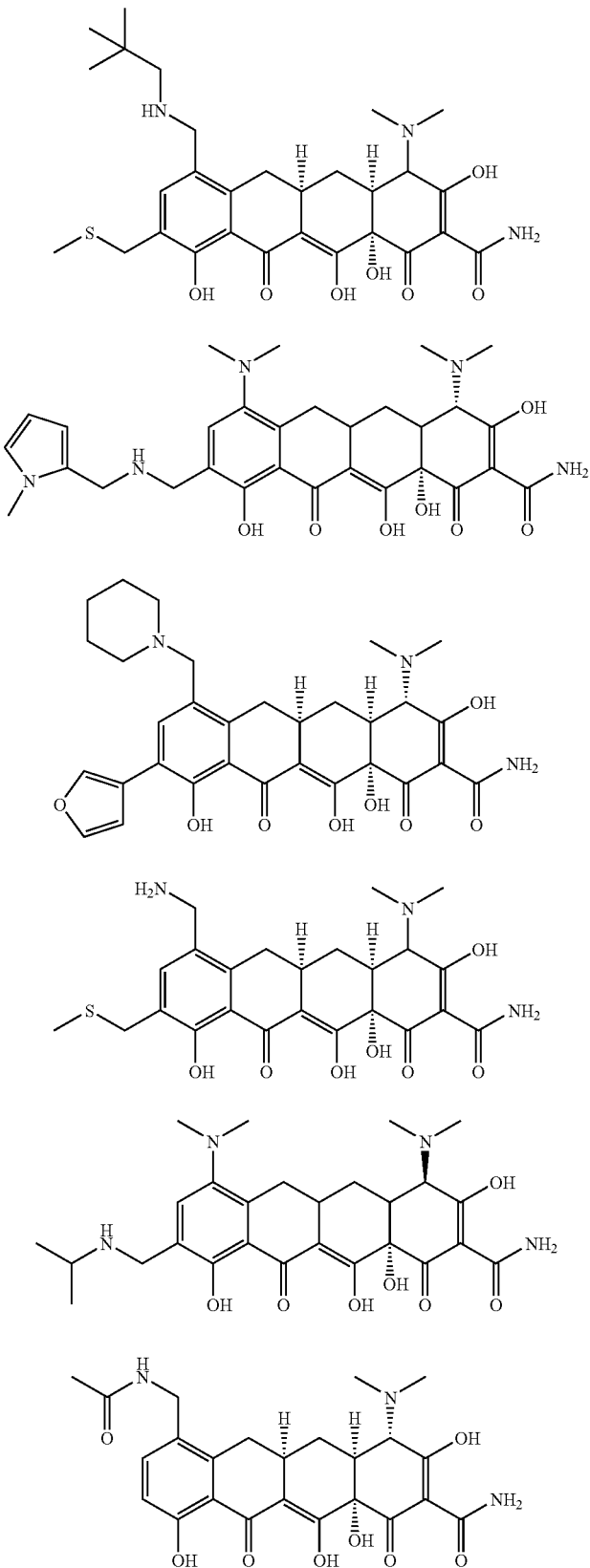

TABLE 1-continued
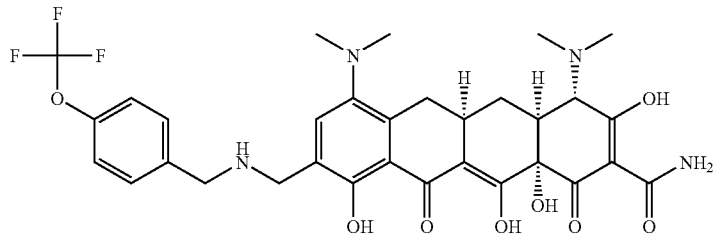
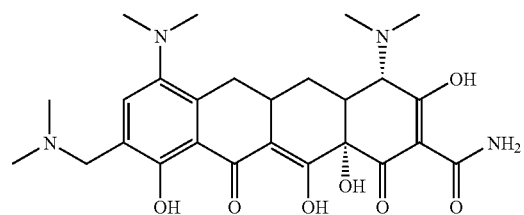
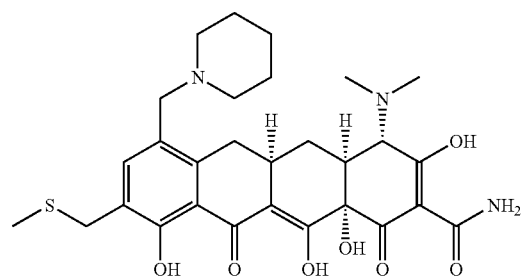
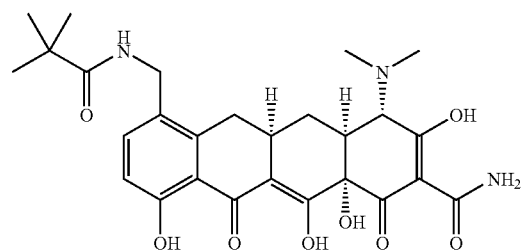
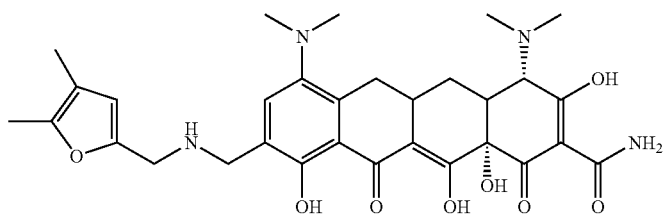
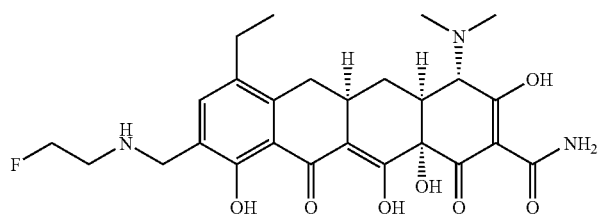

TABLE 1-continued
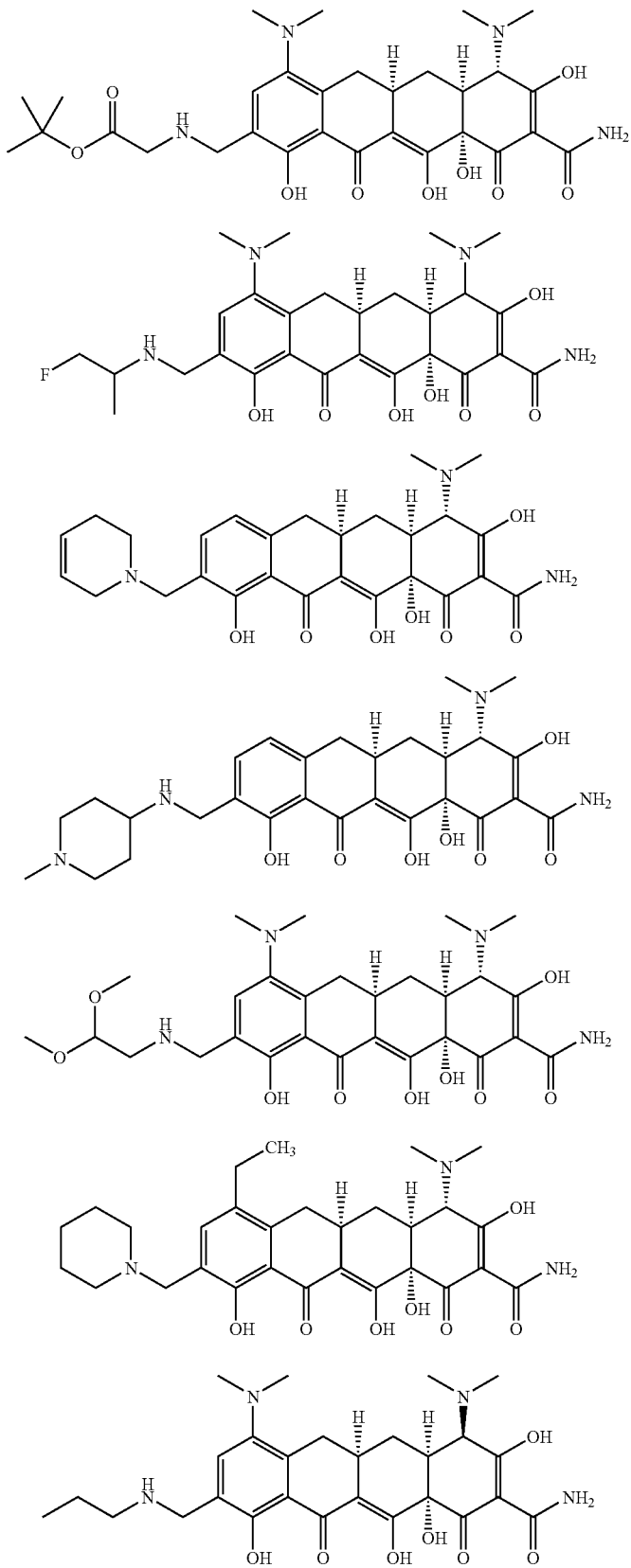

TABLE 1-continued
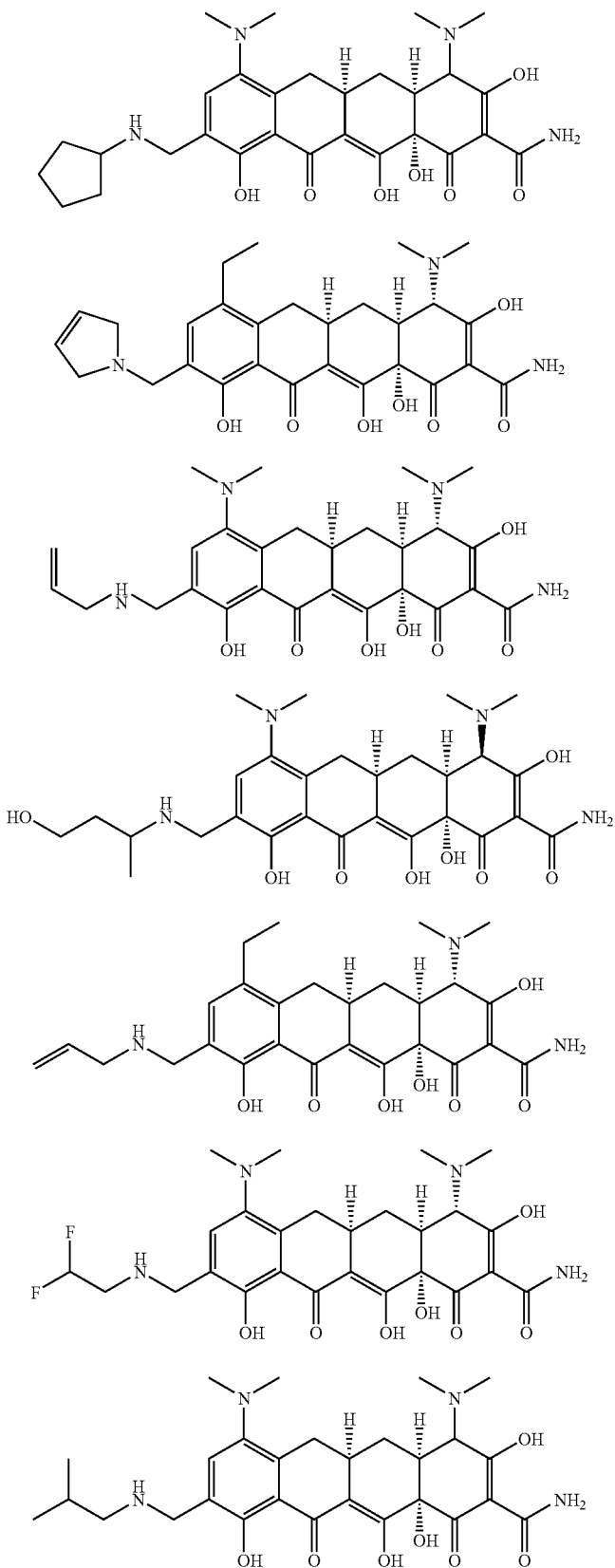

TABLE 1-continued
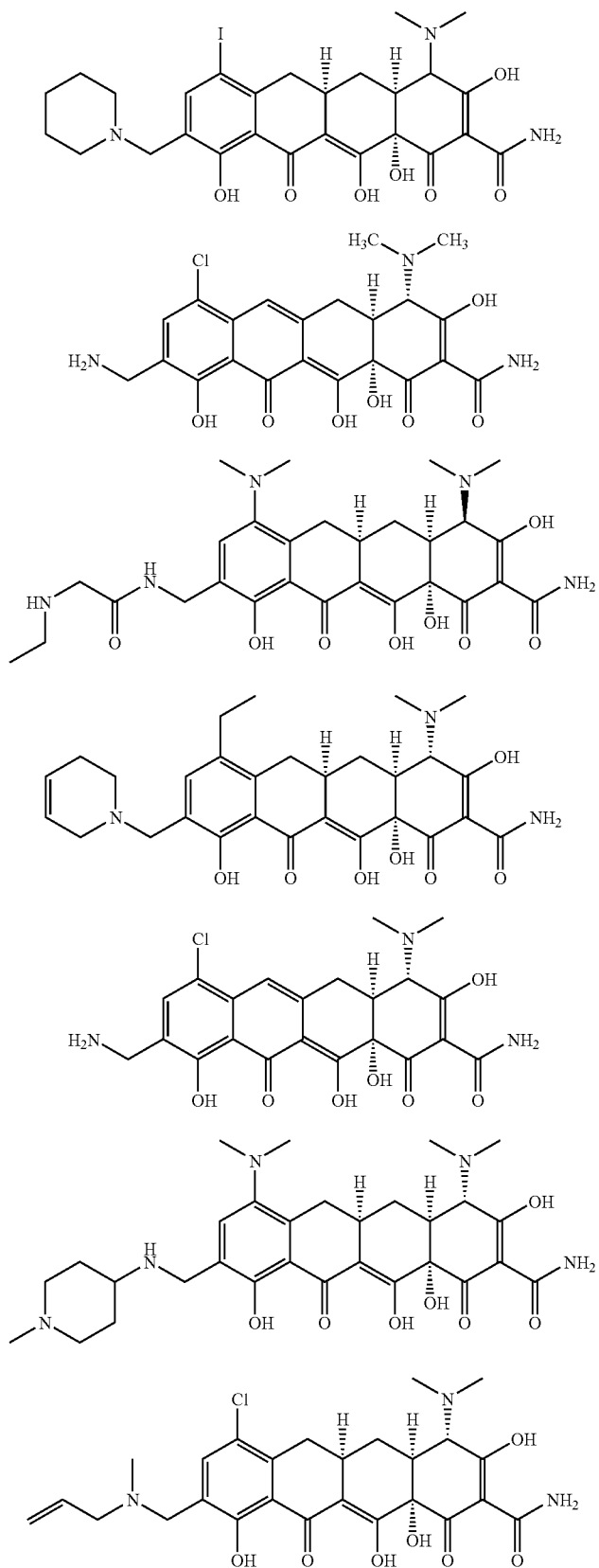

TABLE 1-continued
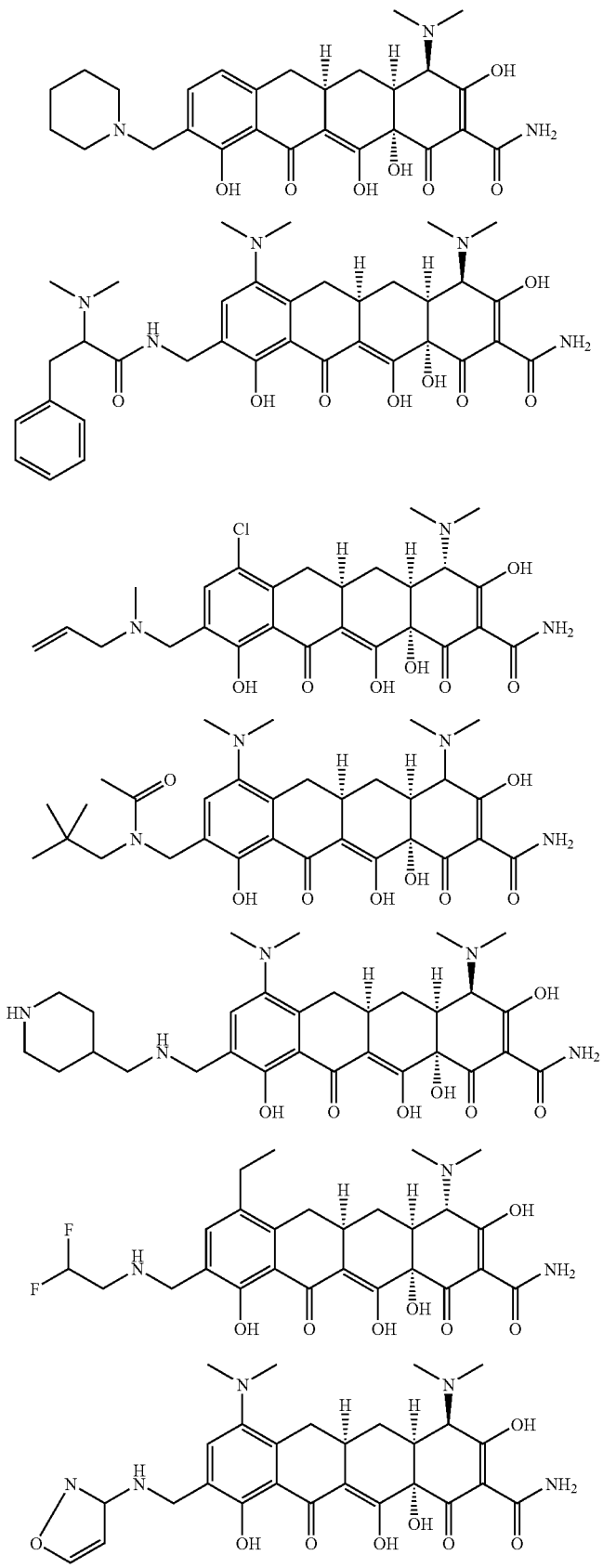

TABLE 1-continued
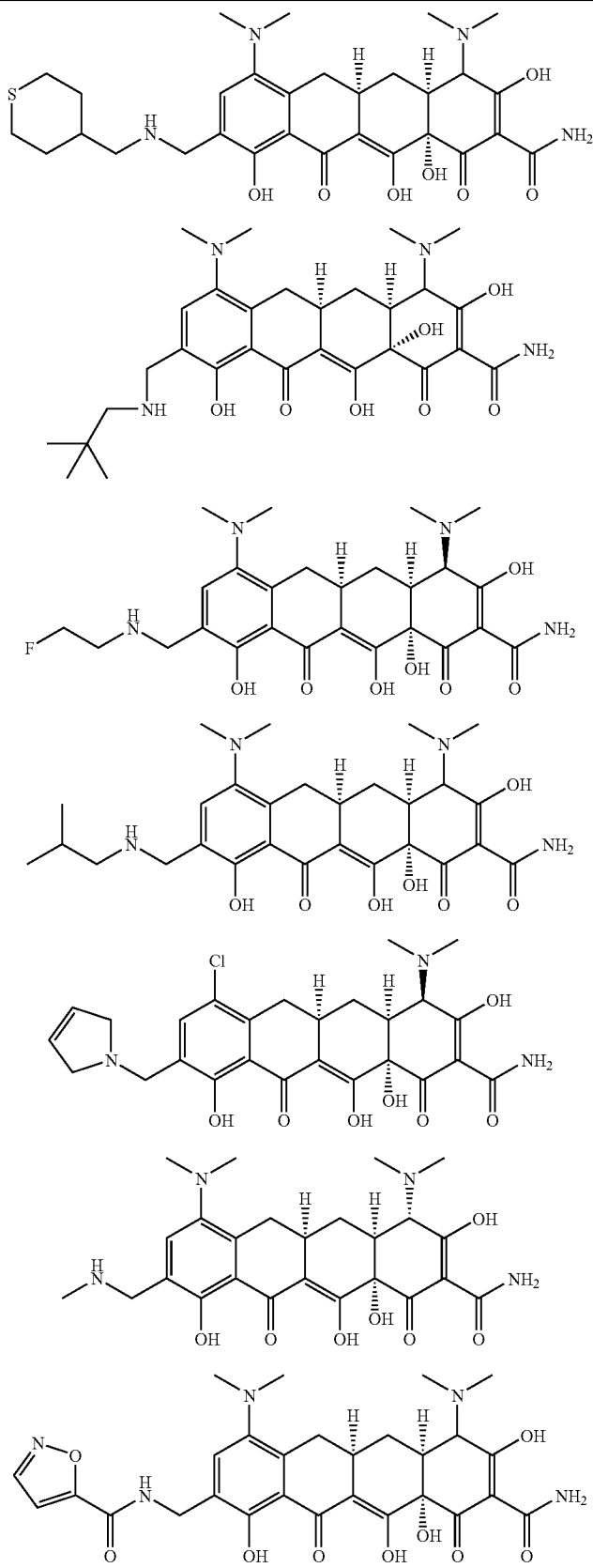

TABLE 1-continued
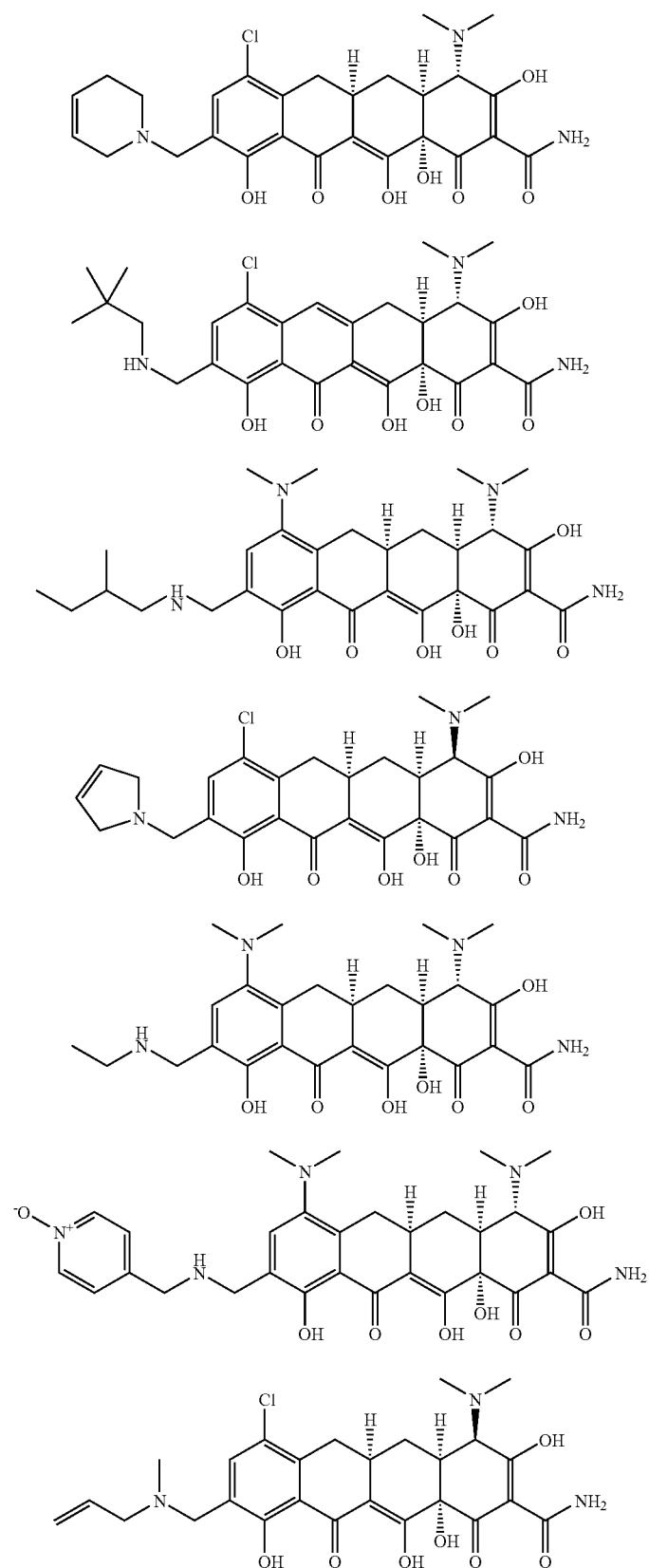

TABLE 1-continued
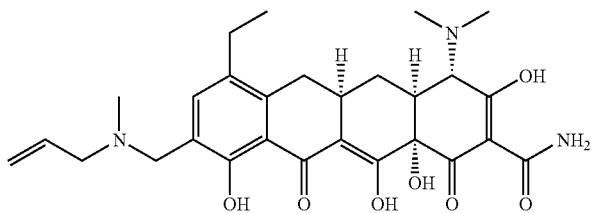
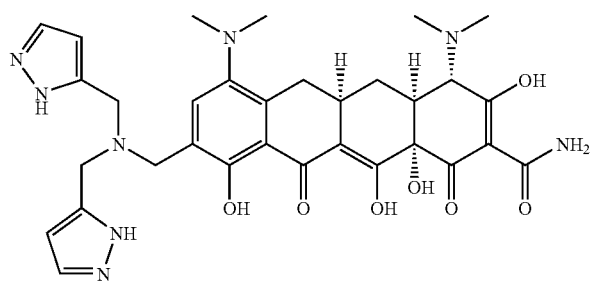
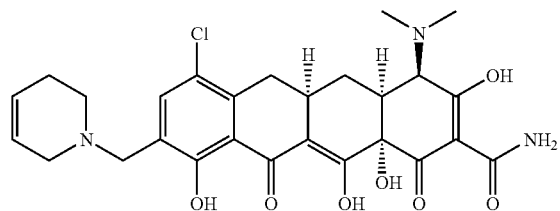
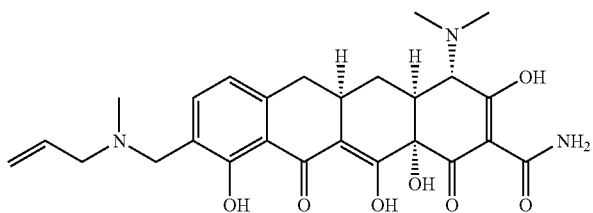
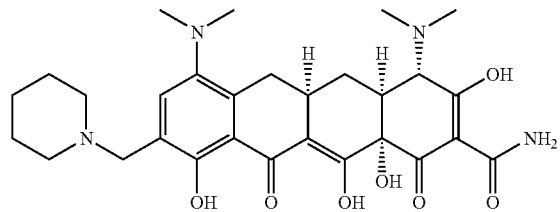
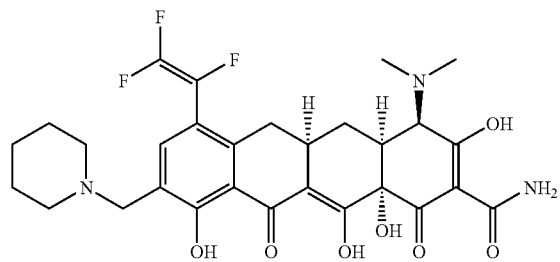

TABLE 1-continued
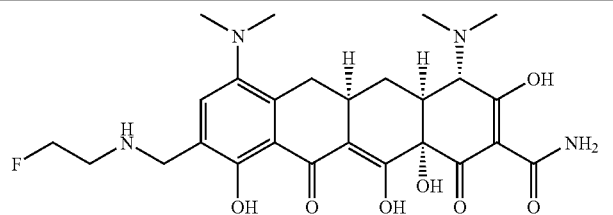
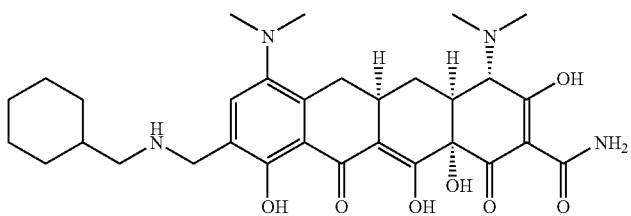
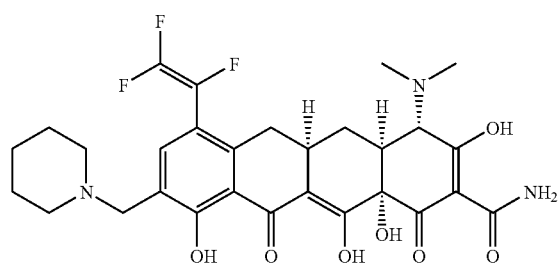
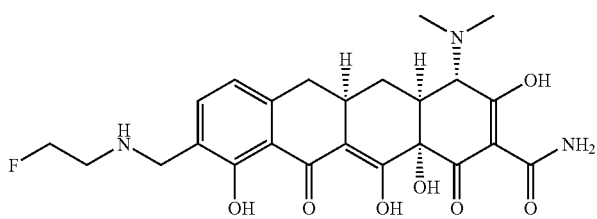
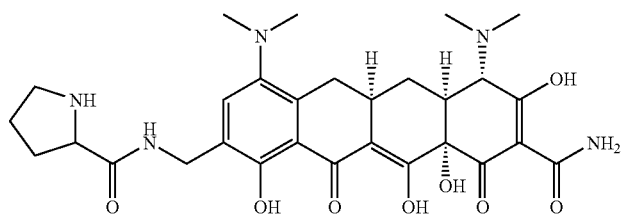
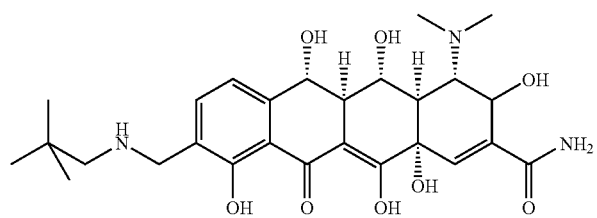
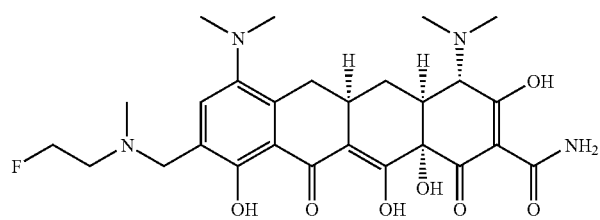

TABLE 1-continued
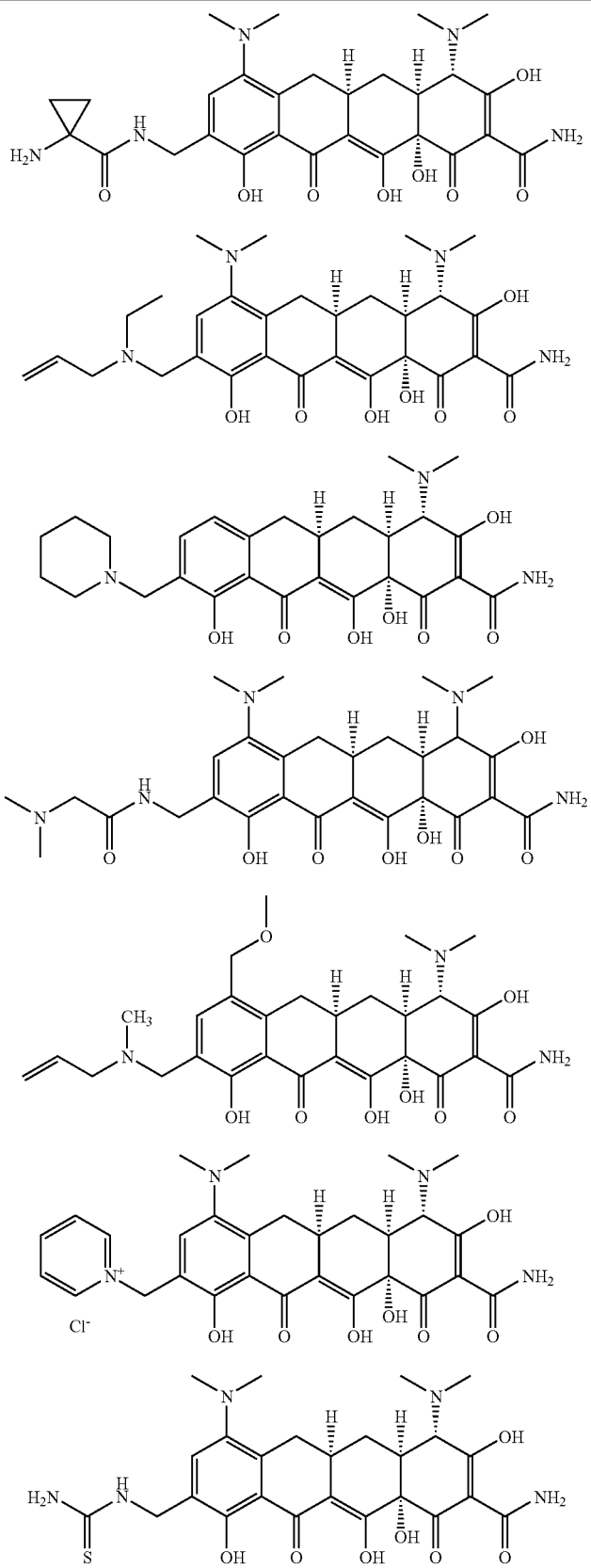

TABLE 1-continued
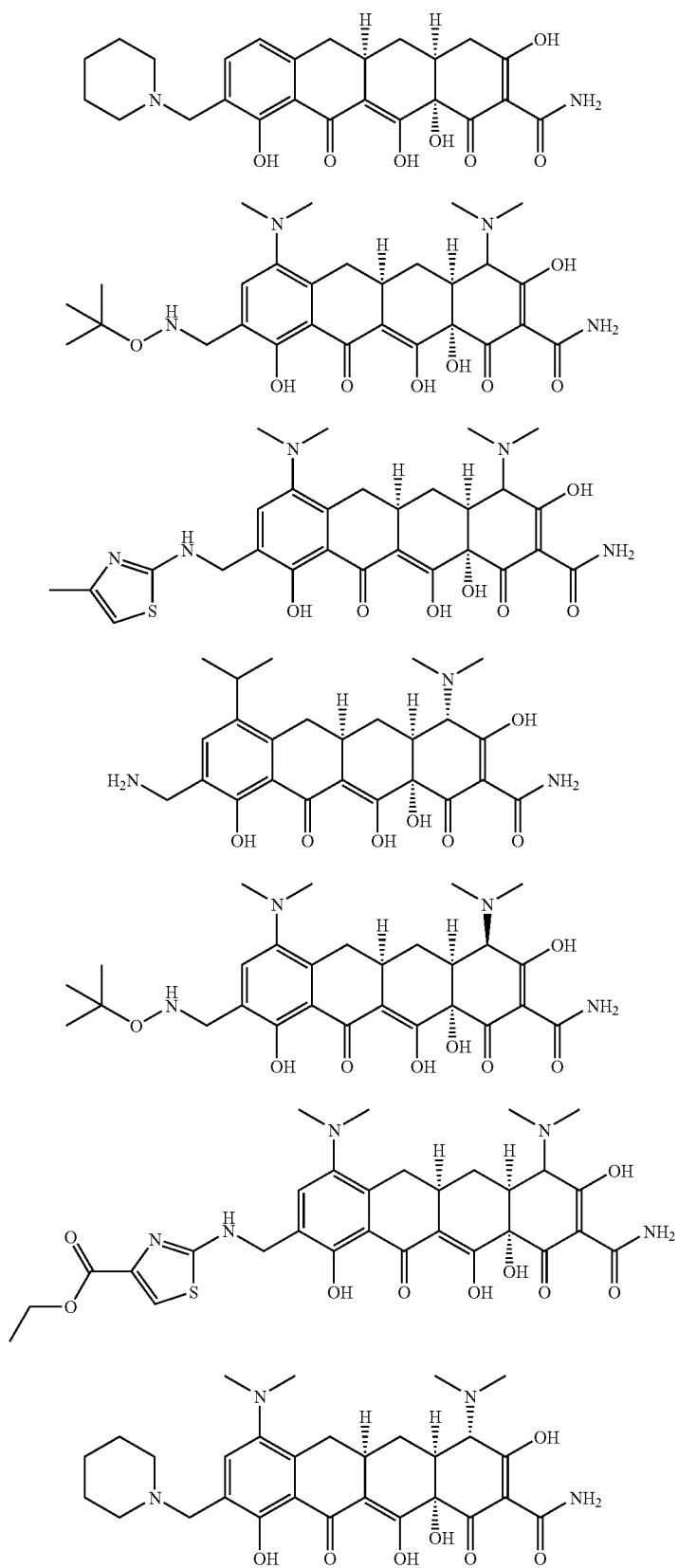

TABLE 1-continued
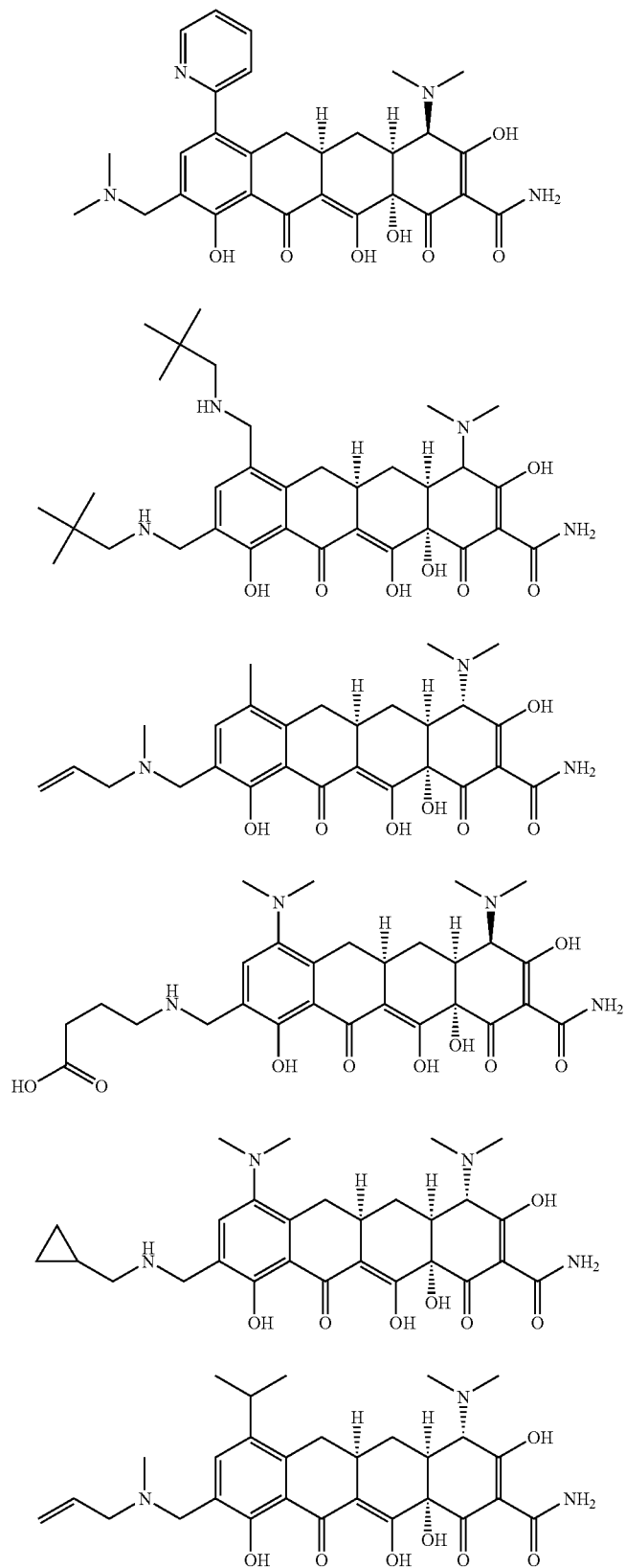

TABLE 1-continued
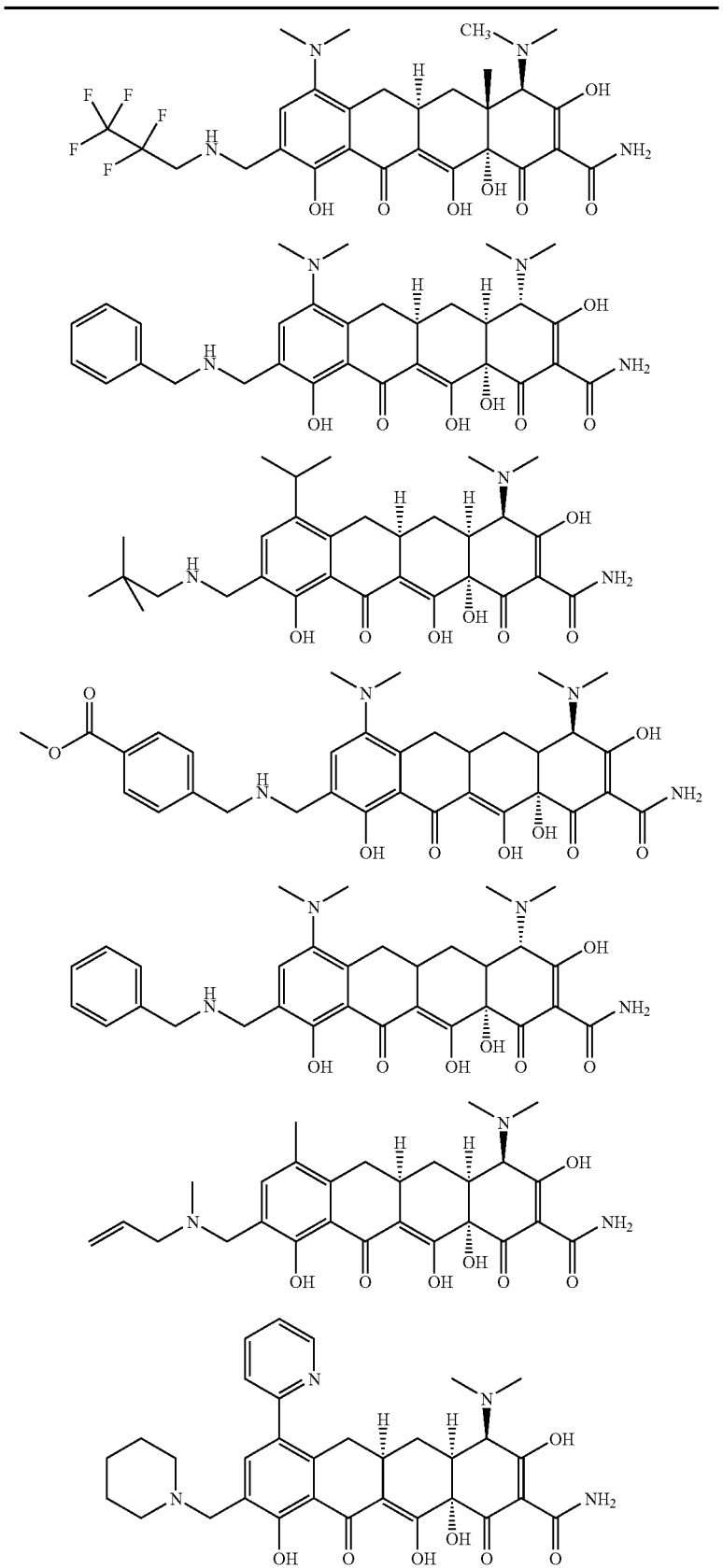

TABLE 1-continued
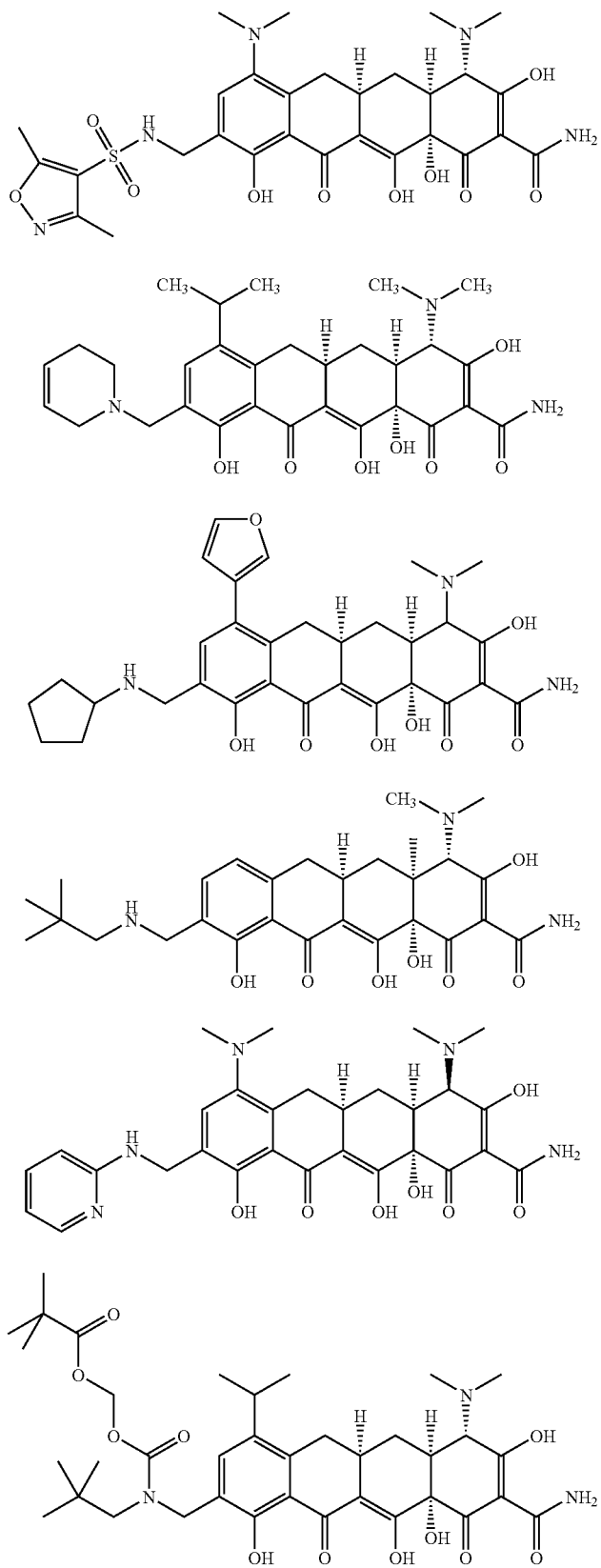

TABLE 1-continued
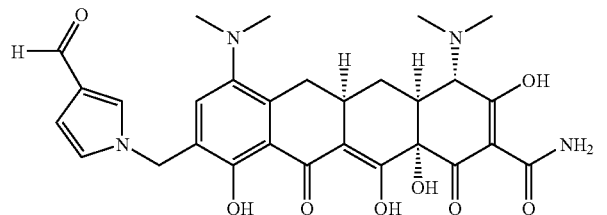
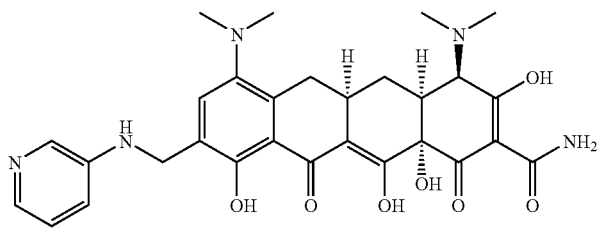
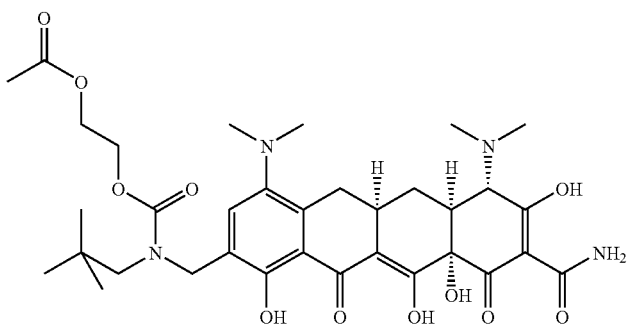
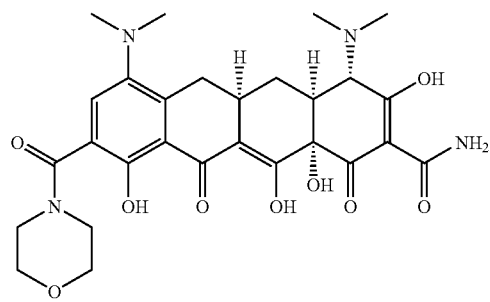
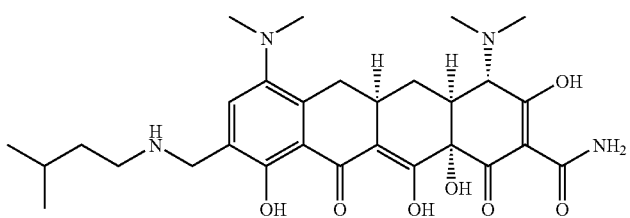
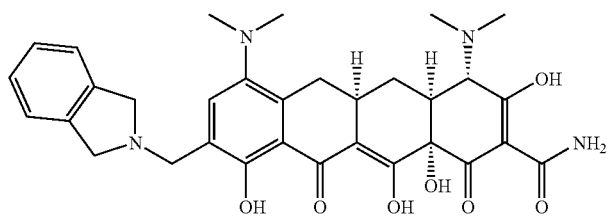

TABLE 1-continued
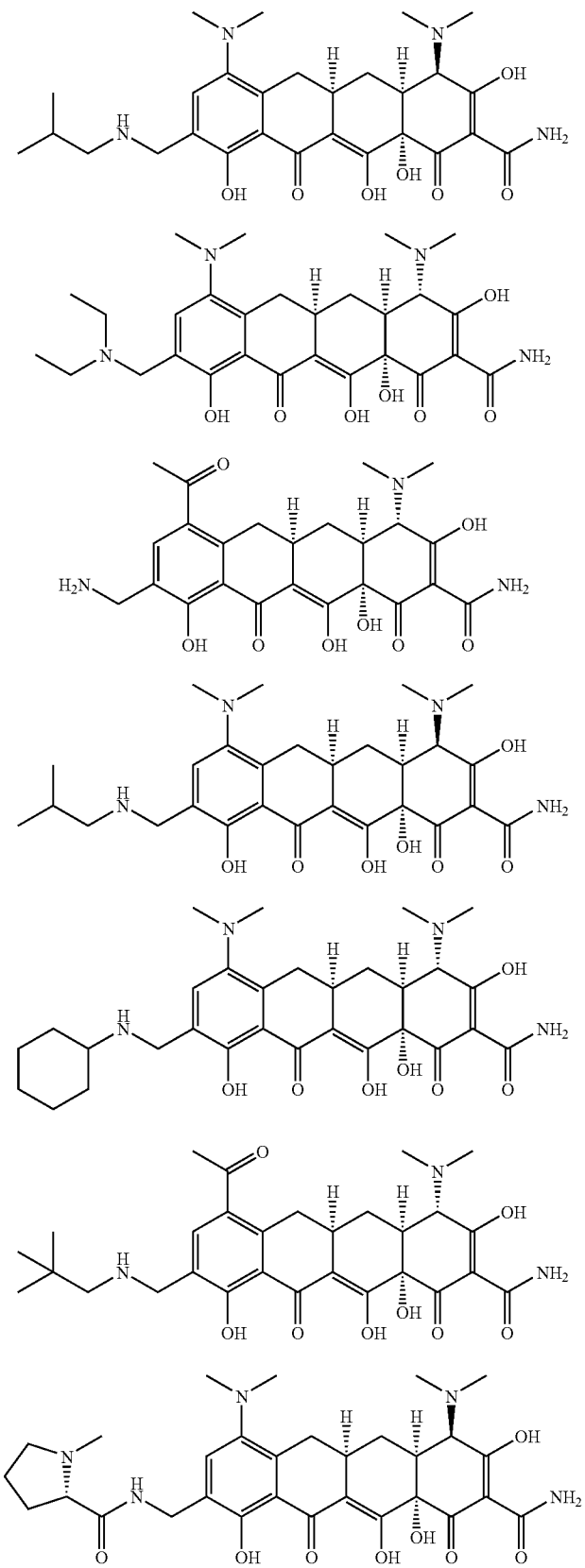

TABLE 1-continued
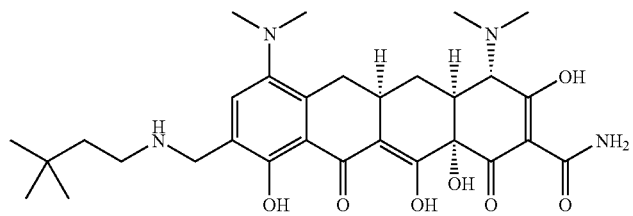
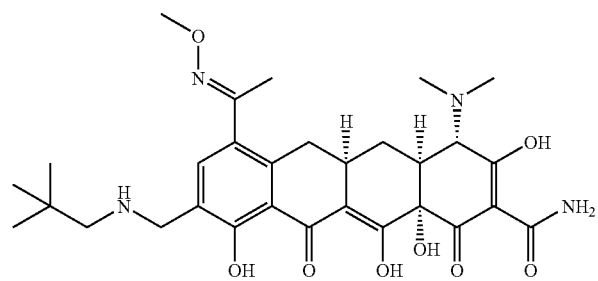
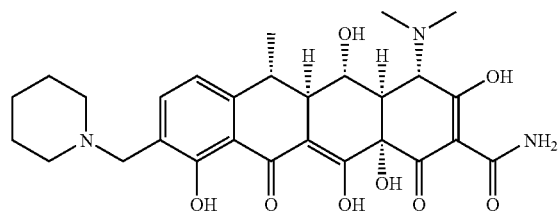
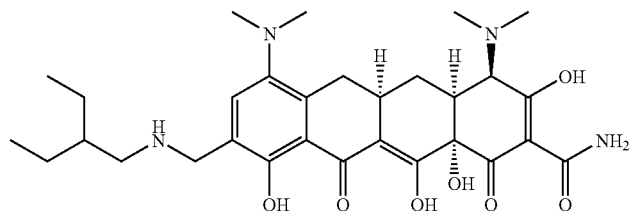
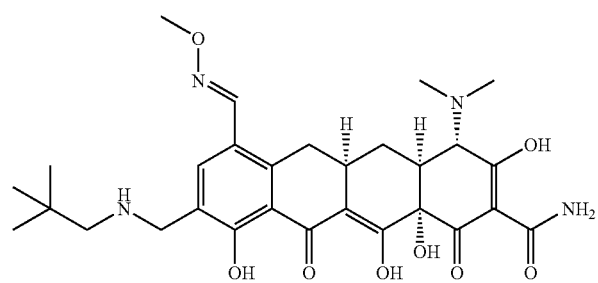
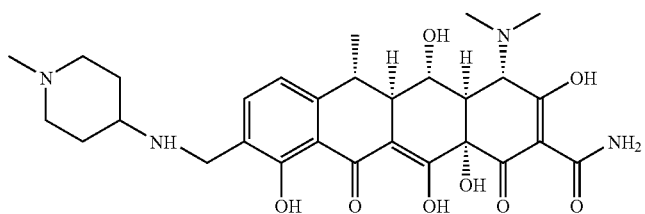

TABLE 1-continued
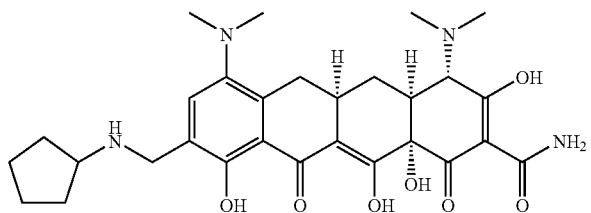
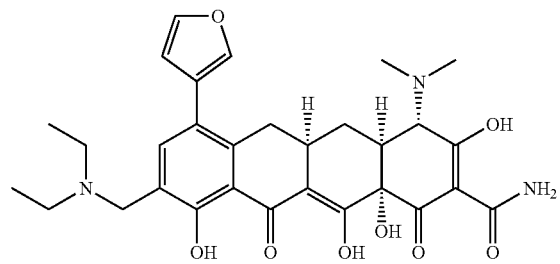
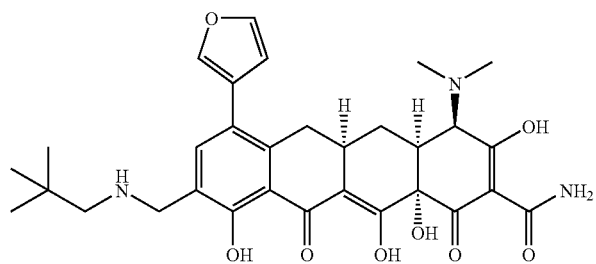
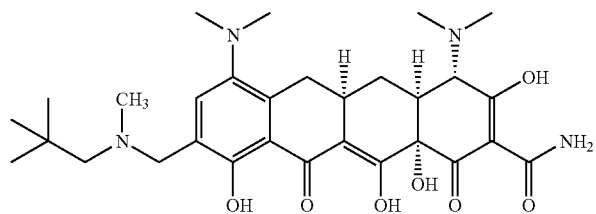
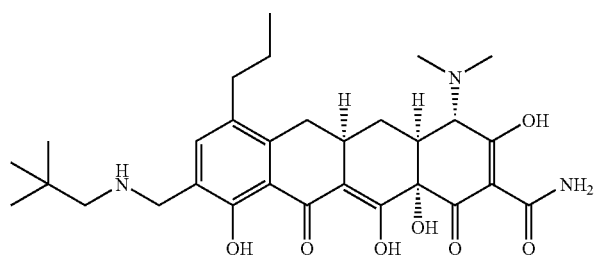
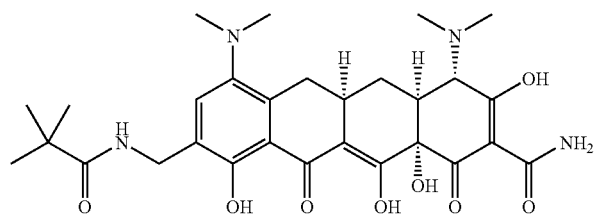

TABLE 1-continued
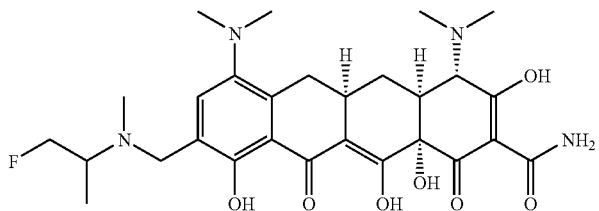
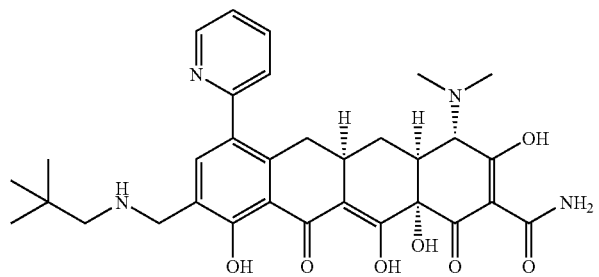
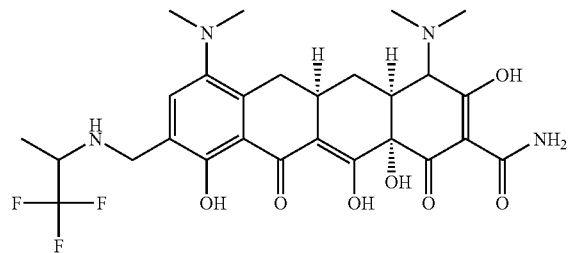
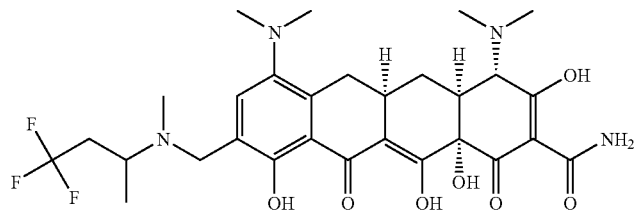
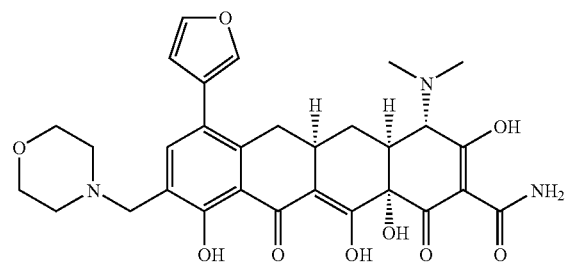
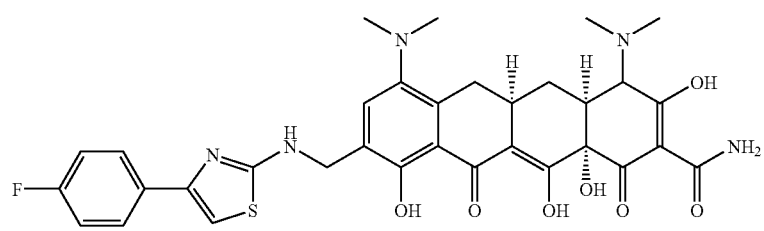

TABLE 1-continued
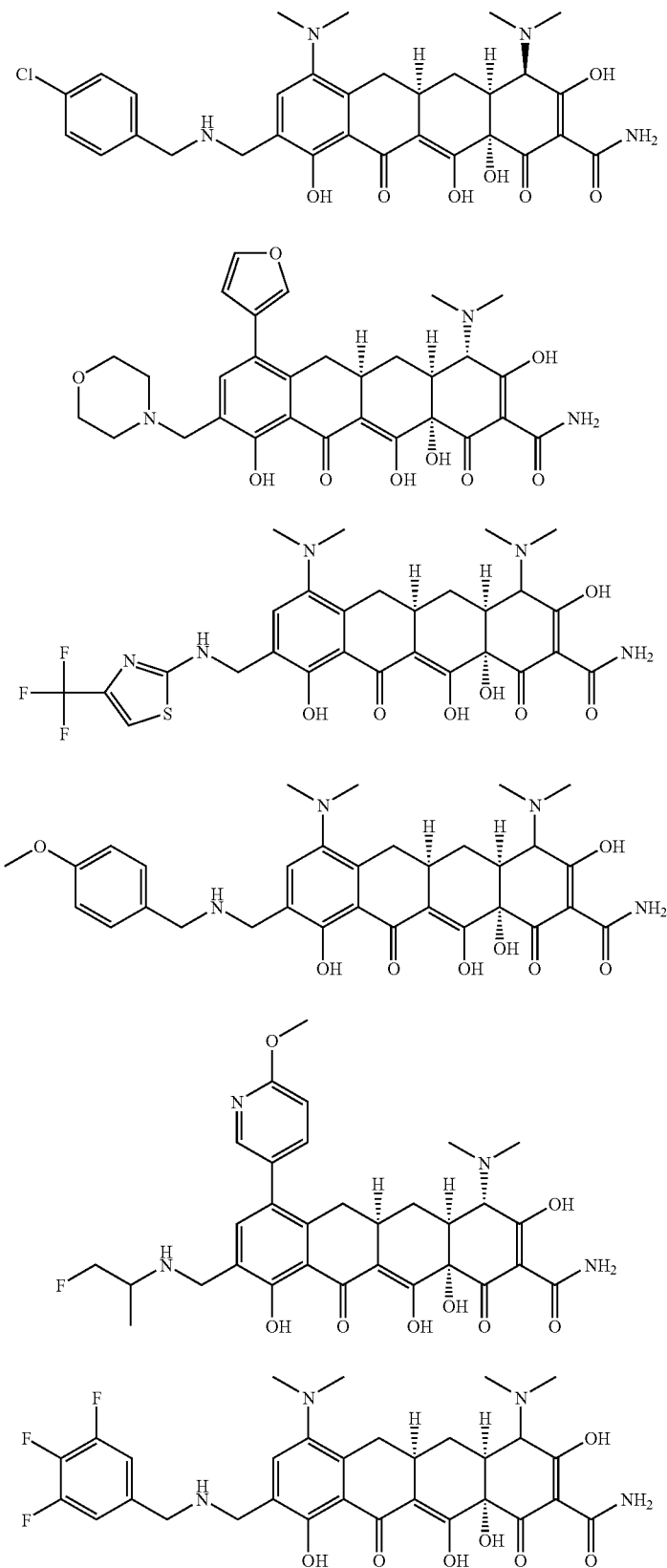

TABLE 1-continued
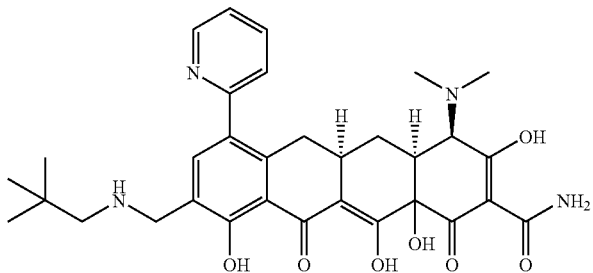
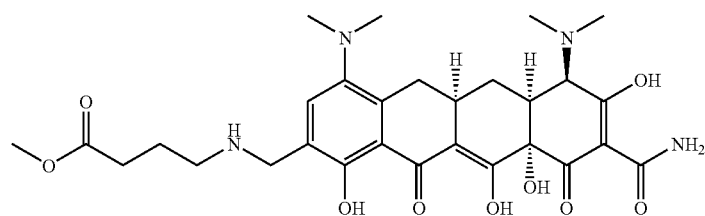
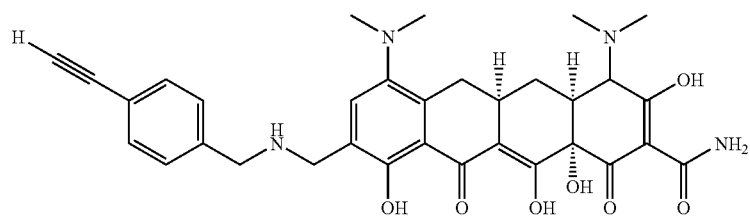
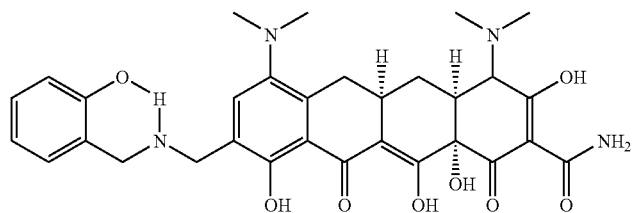
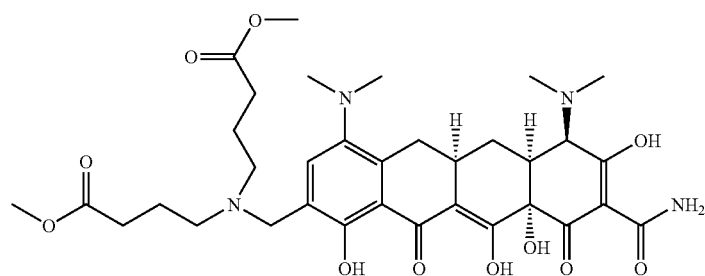
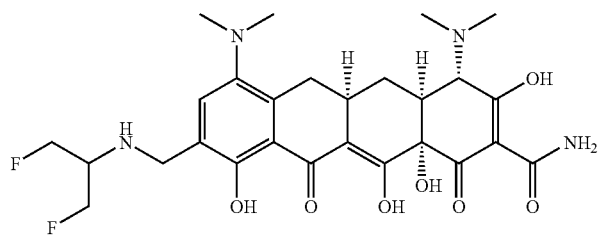

TABLE 1-continued
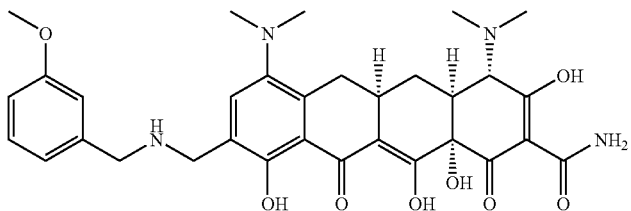
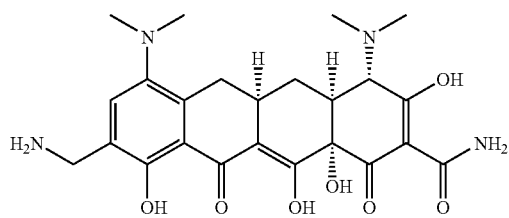
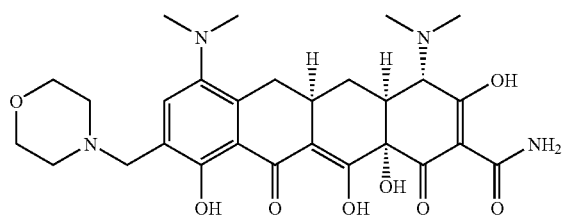
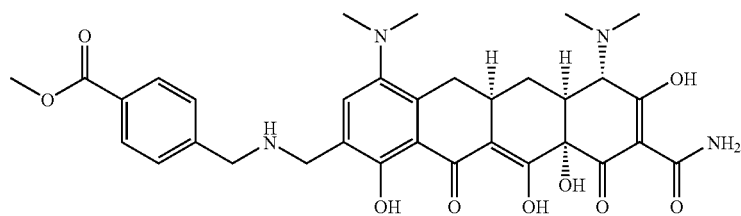
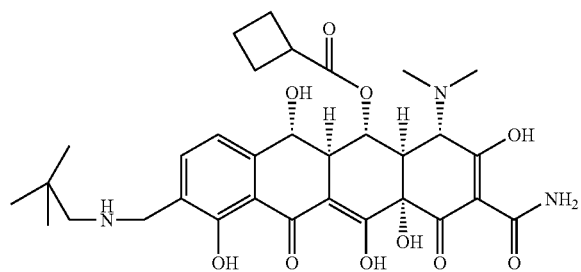
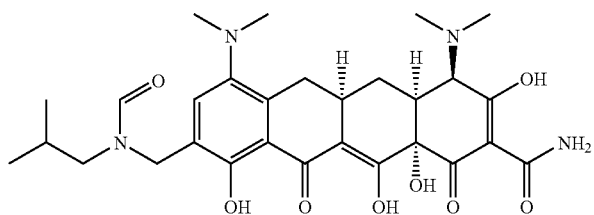

TABLE 1-continued
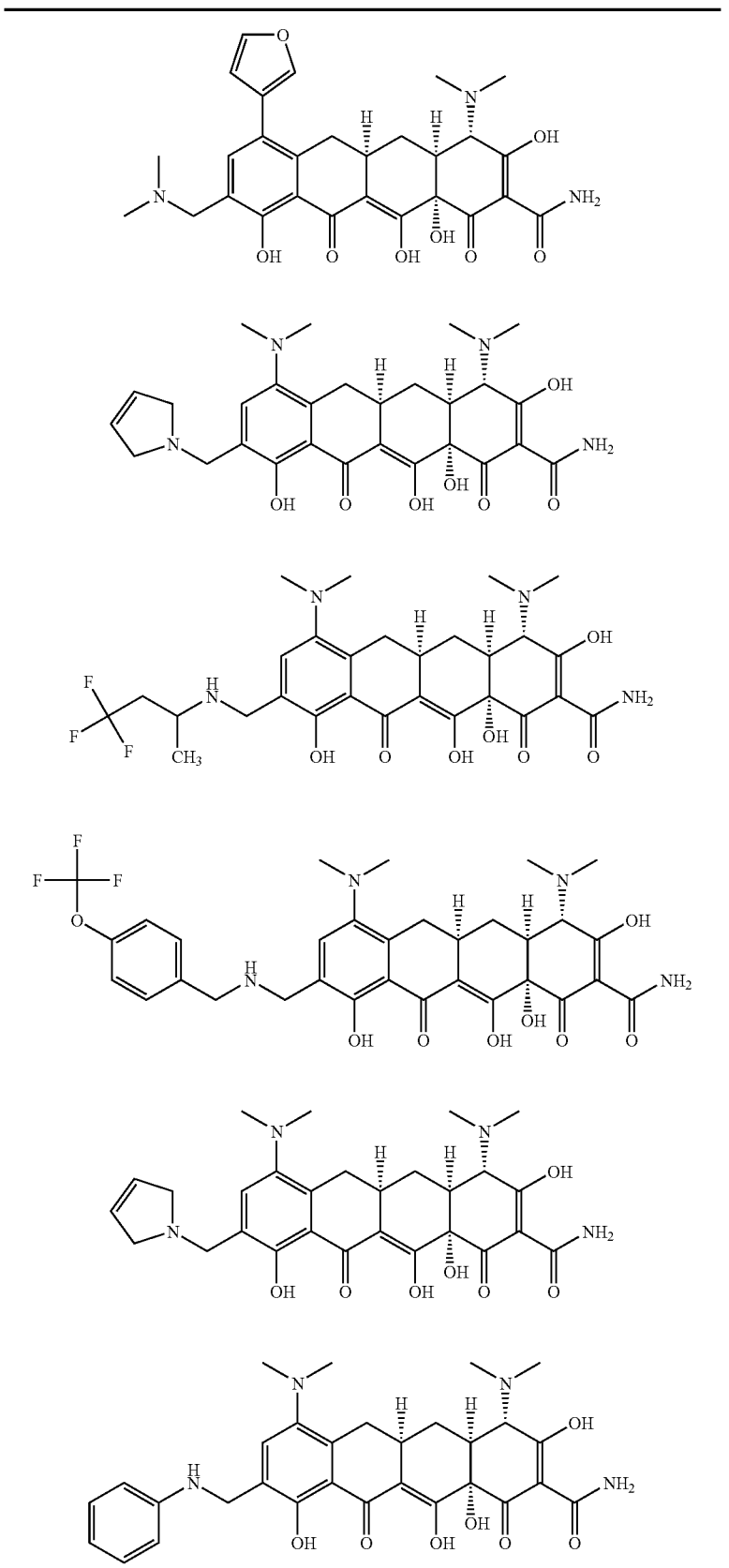

TABLE 1-continued
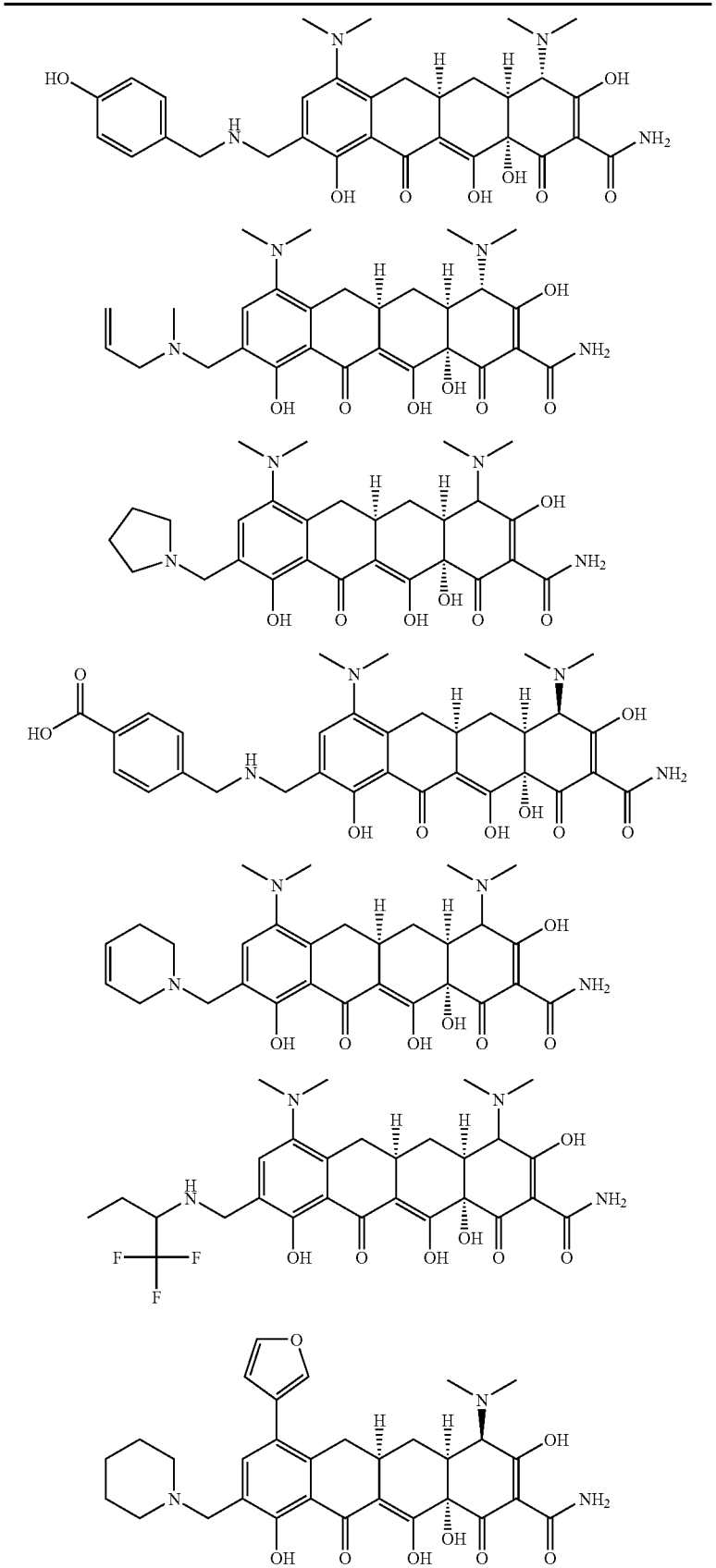

TABLE 1-continued

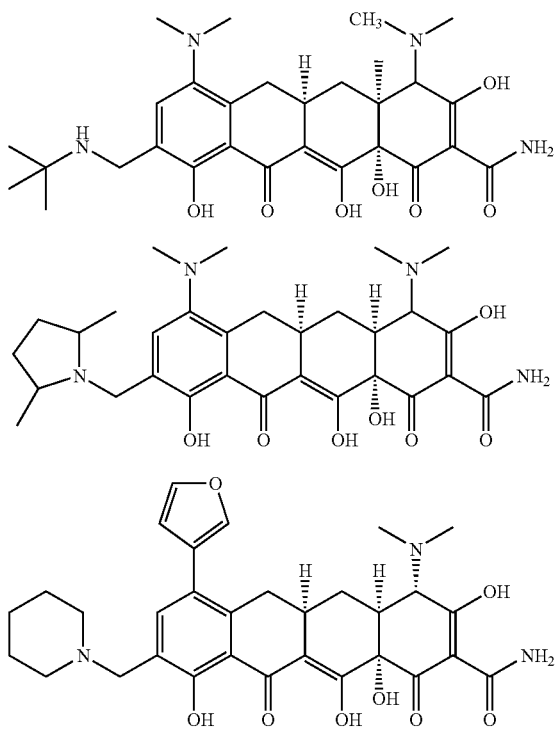

The invention also pertains, at least in part to a method for the synthesis of aminoalkyl tetracycline compounds, such as those described above. The method includes contacting a tetracycline compound with an aminoalkylating reagent under appropriate conditions to form an aminoalkyl tetracycline compound.

The term "tetracycline compound" includes many compounds with a similar ring structure to tetracycline. Examples of tetracycline compounds include: tetracycline, chlortetracycline, oxytetracycline, demeclocycline, methacycline, sancycline, doxycycline, minocycline, chelocardin, rolitetracycline, lymecycline, apicycline; clomocycline, guamecycline, meglucycline, mepylcycline, penimepicycline, pipacycline, etamocycline, penimocycline, etc. Other derivatives and analogues comprising a similar four ring structure are also included (for a review, see W. Rogalski, "Chemical Modifications of Tetracyclines," the entire contents of which are hereby incorporated herein by reference). Table 2 depicts tetracycline and several known other tetracycline derivatives.

TABLE 2

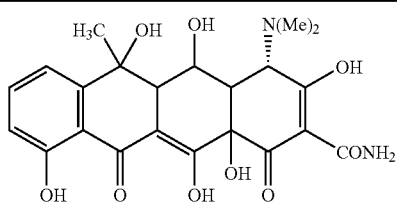

Oxytetracycline

TABLE 2-continued

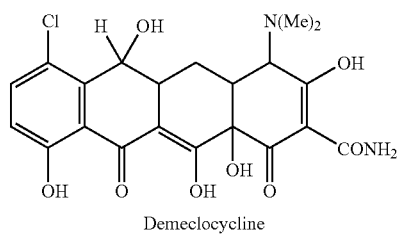

Demeclocycline

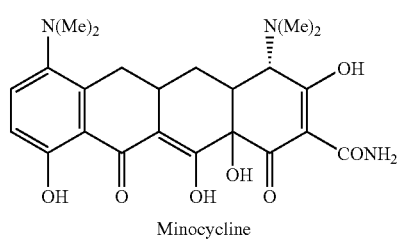

Minocycline

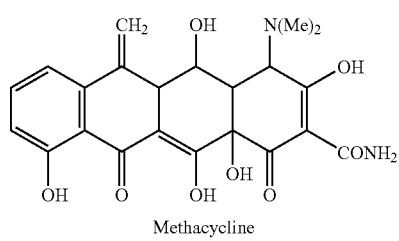

Methacycline

TABLE 2-continued

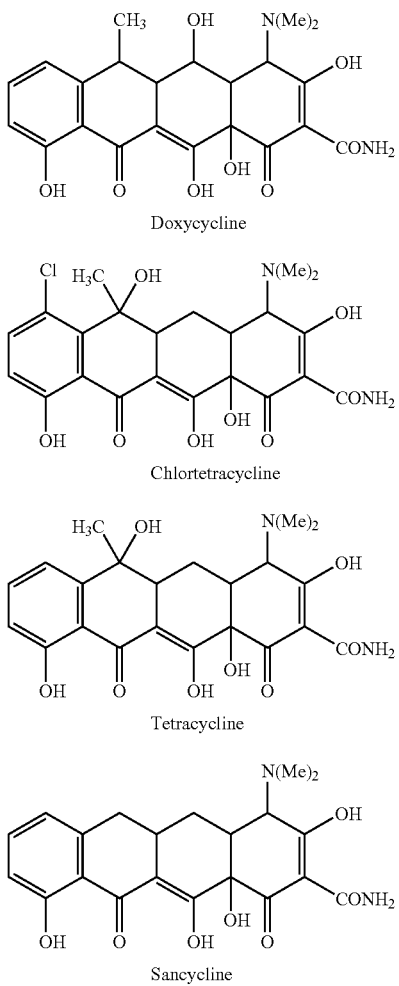

Doxycycline

Chlortetracycline

Tetracycline

Sancycline

Other tetracycline compounds which may be modified using the methods of the invention include, but are not limited to, 6-demethyl-6-deoxy-4-dedimethylaminotetracycline; tetracyclino-pyrazole; 7-chloro4-dedimethylaminotetracycline; 4-hydroxy-4-dedimethylaminotetracycline; 12α-deoxy-4-dedimethylaminotetracycline; 5-hydroxy-6α-deoxy-4-dedimethylaminotetracycline; 4-dedimethylamino-12α-deoxyanhydrotetracycline; 7-dimethylamino-6-demethyl-6-deoxy-4-dedimethylaminotetracycline; tetracyclinonitrile; 4-oxo4-dedimethylaminotetracycline 4,6-hemiketal; 4-oxo-11a Cl-4-dedimethylaminotetracycline-4,6-hemiketal; 5a,6-anhydro-4-hydrazono-4-dedimethylamino tetracycline; 4-hydroxyimino-4-dedimethylamino tetracyclines; 4-hydroxyimino-4-dedimethylamino 5a,6-anhydrotetracyclines; 4-amino-4-dedimethylamino-5a, 6 anhydrotetracycline; 4-methylamino-4-dedimethylamino tetracycline; 4-hydrazono-11a-chloro-6-deoxy-6-demethyl-6-methylene-4-dedimethylamino tetracycline; tetracycline quaternary ammonium compounds; anhydrotetracycline betaines; 4-hydroxy-6-methyl pretetramides; 4-keto tetracyclines; 5-keto tetracyclines; 5a, 11a dehydro tetracyclines; 11a Cl-6, 12 hemiketal tetracyclines; 11a Cl-6-methylene tetracyclines; 6, 13 diol tetracyclines; 6-benzylthiomethylene tetracyclines; 7, 11a-dichloro-6-fluoro-methyl-6-deoxy tetracyclines; 6-fluoro (α)-6-demethyl-6-deoxy tetracyclines; 6-fluoro (β)-6-demethyl-6-deoxy tetracyclines;6-α acetoxy-6-demethyl tetracyclines; 6-β acetoxy-6-demethyl tetracyclines; 7, 13-epithiotetracyclines; oxytetracyclines; pyrazolotetracyclines; 11a halogens of tetracyclines; 12a formyl and other esters of tetracyclines; 5, 12a esters of tetracyclines; 10, 12a-diesters of tetracyclines; isotetracycline; 12-a-deoxyanhydro tetracyclines; 6-demethyl-12a-deoxy-7-chloroanhydrotetracyclines; B-nortetracyclines; 7-methoxy-6-demethyl-6-deoxytetracyclines; 6-demethyl-6-deoxy-5a-epitetracyclines; 8-hydroxy-6-demethyl-6-deoxy tetracyclines; monardene; chromocycline; 5a methyl-6-demethyl-6-deoxy tetracyclines; 6-oxa tetracyclines, and 6 thia tetracyclines.

The term "aminoalkyl tetracycline compounds" includes tetracycline compounds with an aminoalkyl substituent, (e.g., —CH$_2$NR'R") at the 7 and/or 9 positions. In an embodiment, the substitution at the 7 and/or 9 position enhances the ability of the tetracycline compound to perform its intended function (e.g., as an antibiotic, to treat a tetracycline compound responsive state, etc.). The term "aminoalkylating reagent" includes reagents which are capable of contacting the tetracycline compound and, under appropriate conditions, reacting with it to form an aminoalkyl tetracycline compound. The amino alkylating reagent may be added to the reaction mixture or may be formed in situ. Examples of aminoalkylating reagents, include, but are not limited to, compounds of the formula (IV):

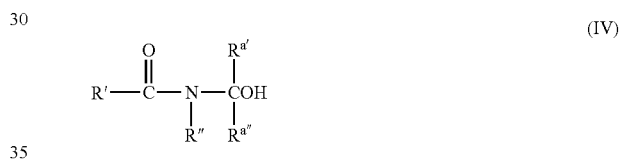

(IV)

wherein $R^{a'}$ and $R^{a''}$ are each independently hydrogen or halogen;

R' is hydrogen, alkyl, alkenyl, alkynyl, aryl, heteroaryl, or halogen; and

R" is hydrogen or optionally linked to R' to form a 4–8 membered ring. The ring may be optionally substituted, e.g., with halogens and may comprise carbons and/or heteroatoms such as oxygen, nitrogen, and sulfur. R' may be further substituted with any substituent which does not prevent the reagent from reacting with the tetracycline compound of the invention, under the appropriate conditions. In another further embodiment, R' is alkyl, e.g., unsubstituted or substituted (e.g., with halogens, e.g., chlorine, fluorine, bromine, iodine, etc.). In another embodiment, R' is aryl, e.g., phenyl, e.g., unsubstituted or substituted (e.g., with halogens (e.g., chlorine, bromine, fluorine, etc.), hydroxy, alkoxy, esters, amino, etc.). In another embodiment, $R^{a'}$ and $R^{a''}$ are each hydrogen. Other examples of aminoalkylating reagents include N-hydroxymethylphthalimide.

Examples of amino-alkylating reagents include, but are not limited to:

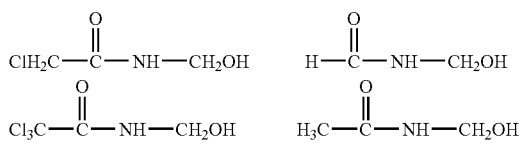

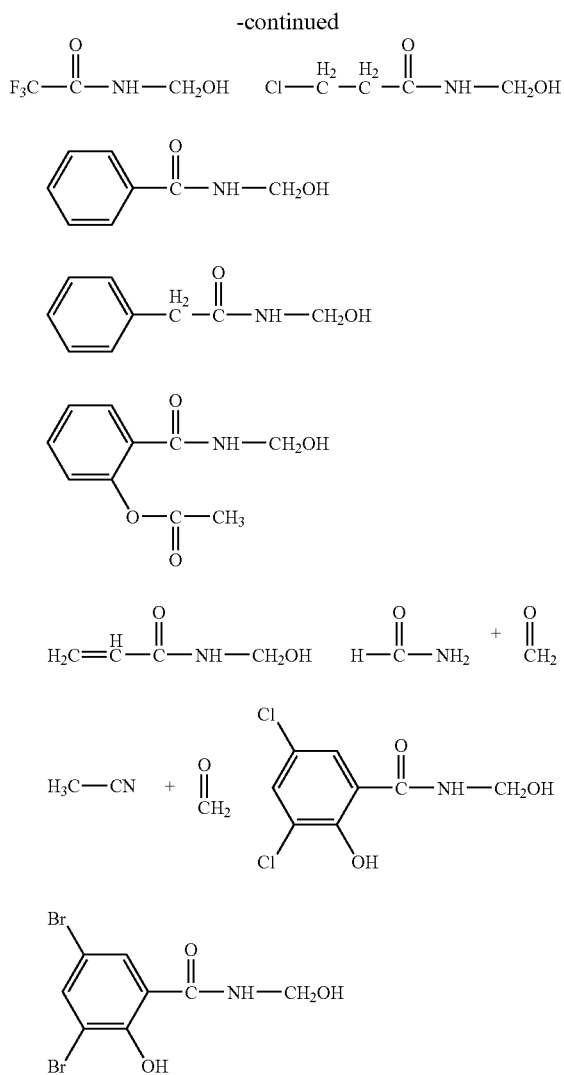

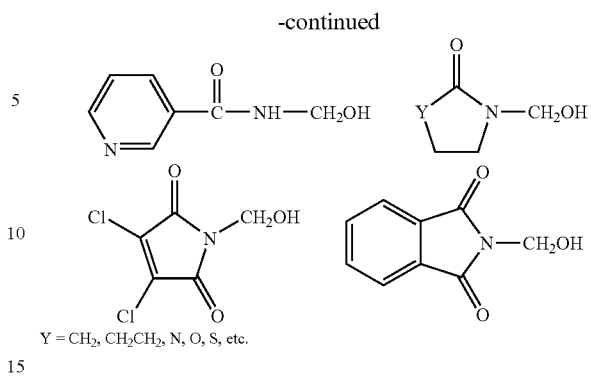

Y = CH$_2$, CH$_2$CH$_2$, N, O, S, etc.

The term "appropriate conditions" include those conditions under which the aminoalkylating reagent and the tetracycline compound interact such that an aminoalkyl tetracycline compound is formed. In an embodiment, the appropriate conditions comprise treating the tetracycline compound with an acid prior to, or concurrently with the addition of the aminoalkylating reagent to the reaction mixture. Examples of acids which maybe used alone or in combination include acids known in the art, as well as, sulfuric acid, hydrofluoric acid (HF), methanesulfonic acid, trifluoromethane sulfonic acid, hydrochloric acid, hydrochloric acid in aqueous ethanol, acetic acid, methanesulfonic acid, and trifluoroacetic acid (TFA). In a further embodiment, appropriate conditions may also comprise treating the resulting tetracycline compound with a reaction quenching agent (e.g., water).

Each of the reactions described below may be applied to other tetracycline compounds described above. In addition, although many of the schemes depicts substituting the tetracycline compound at the 9 position, similar substituents can be added at the 7 position by using a protecting group at the 9 position, (e.g., such as t-butyl).

Scheme 1 depicts the reaction of sancycline with an aminoalkylating reagent under appropriate conditions such that an aminoalkyl tetracycline compound is formed.

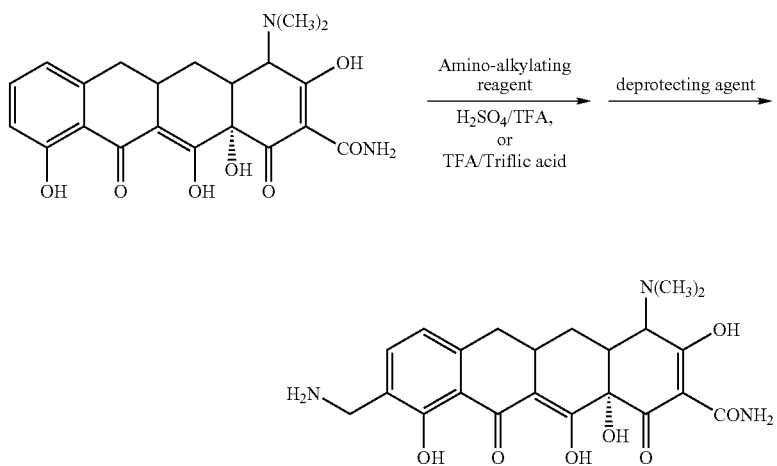

Scheme 2 shows two aminoalkylations of a tetracycline compound with aminoalkylating reagents which comprise a 5 membered ring. Similar reactions can be also be carried out using reagents, with, for example, 6- or 7-membered rings.

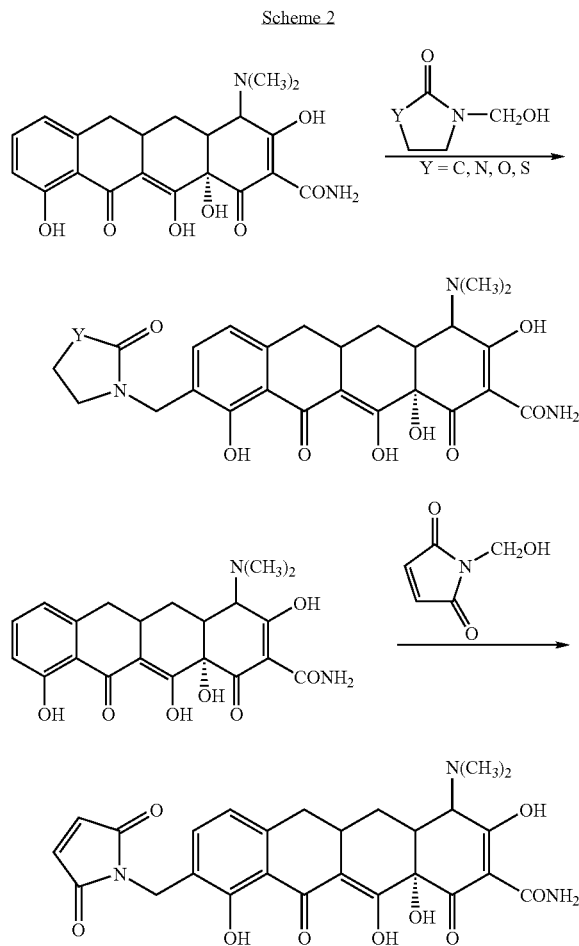

As shown in Scheme 3 below, the synthesis of 7-monosubstituted aminomethyl tetracyclines may be synthesized using protecting groups (i.e. the 9-t-butyl protecting group) to be cleaved using art recognized techniques, such as acid. Examples of acids which can be used include, but are not limited to, HF, trifluoroacetic acid (TFA), H₂SO₄ and mixtures thereof. In this way, regioselective aminomethylation at position 7 is achieved.

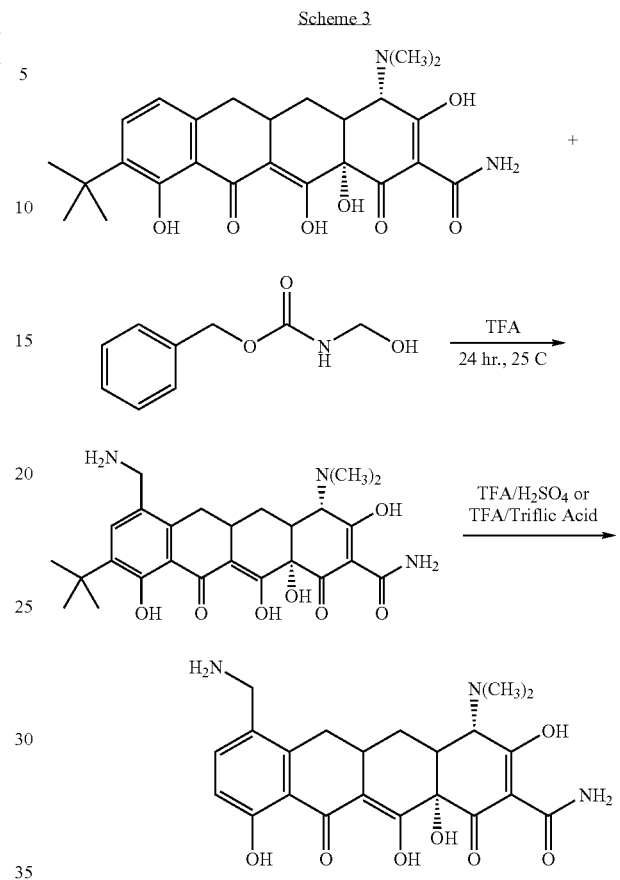

In a further embodiment, the appropriate conditions may further comprise treating the reaction mixture (which may comprise an intermediate aminoalkyl tetracycline compound) with a derivatizing agent under secondary appropriate conditions such that the desired aminoalkyl tetracycline compound is formed. The reactions in Scheme 4 are shown for the 9 position, but the reactions are also applicable to other positions of the tetracycline compound. Additional derivatizing agents and secondary appropriate conditions may be found, for example, in the chemical literature. See, for example, R. C. LaRock, *Comprehensive Organic Transformations*, (New York: VCH Publishers, Inc., 1989) and references cited therein. Any reagent that can react with a primary amine to form a new compound is possible. Examples of some of the diverse structures are shown in Scheme 4 below.

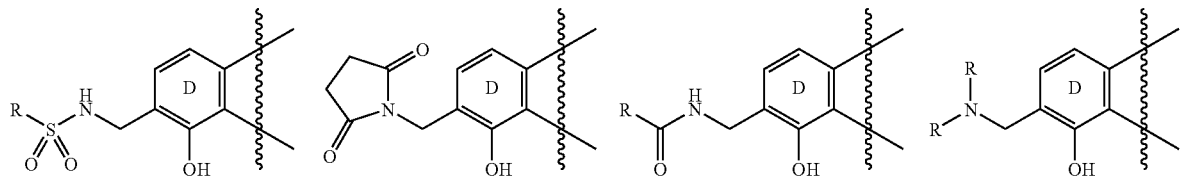

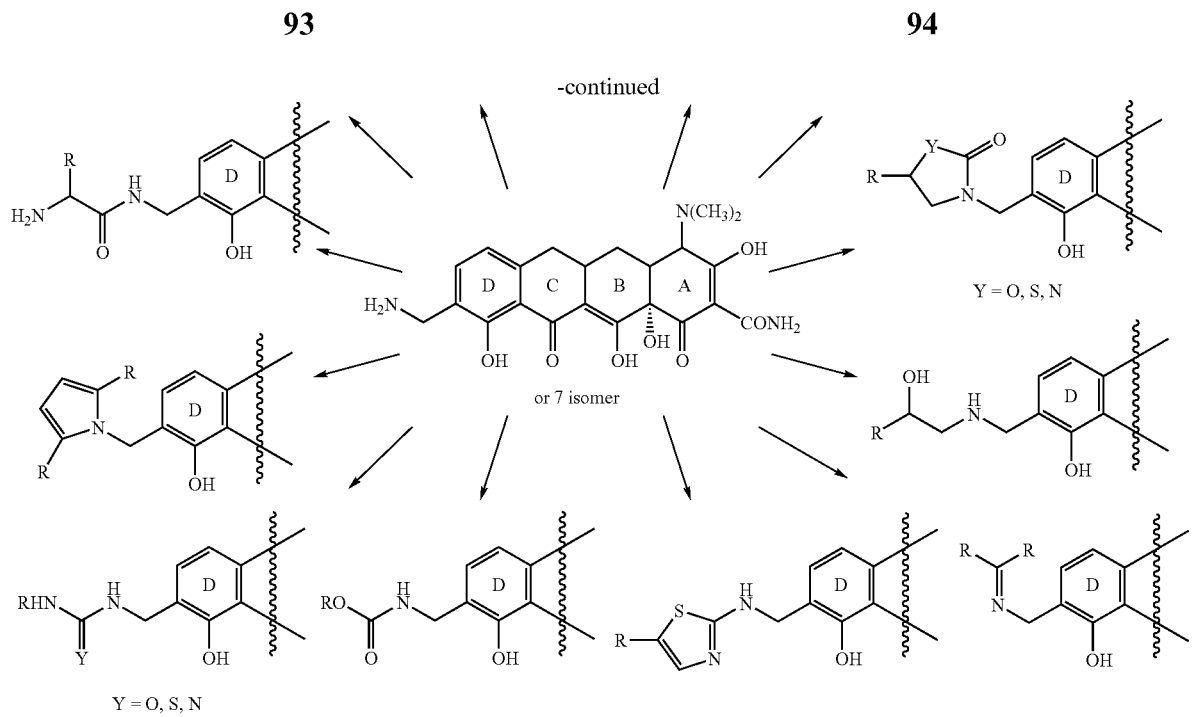

For example, in Scheme 5, an acid chloride derivatizing agent is added to the reaction mixture to form the desired amide aminoalkyl tetracycline compound (*J. Am. Chem Soc.* 71, 2215 (1949); *J. Am. Chem. Soc.* 108, 1039 (1986); *Org. Syn. Coll. Vol.* 4, 339 (1963); *Org. Syn. Coll. Vol.* 5, 387 (1973)).

Scheme 5

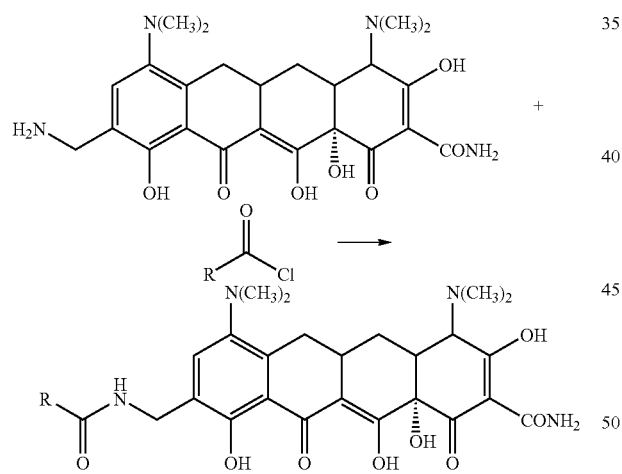

Scheme 6 depicts the reaction of an intermediate aminoalkyl tetracycline compound with an appropriate sulfonyl chloride derivatizing agent, such that the desired sulfonamide aminoalkyl compound is formed (*Org. Syn. Coll. Vol.* 5, 736, 758 (1973)).

Scheme 6

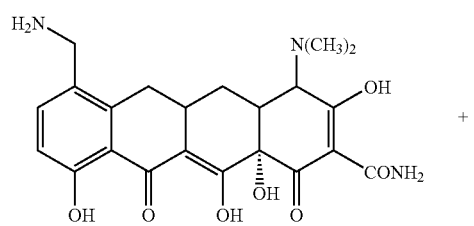

-continued

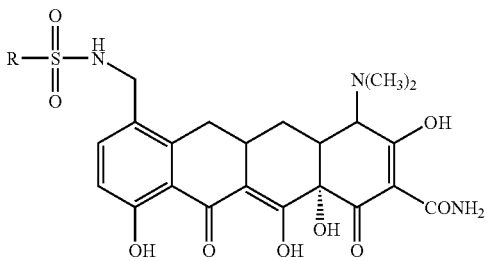

Scheme 7 depicts the reaction of a derivatizing agent with an aminoalkyl tetracycline intermediate to form the resulting carbamate aminoalkyl tetracycline compound.

Scheme 7

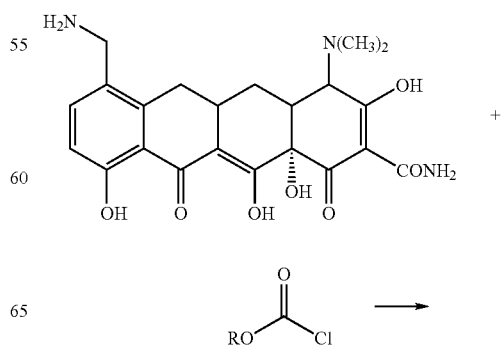

-continued

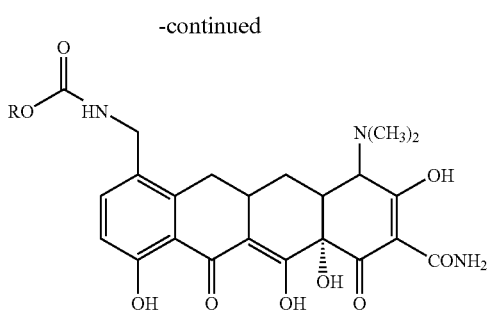

The term "alkyl" includes saturated aliphatic groups, including straight-chain alkyl groups, branched-chain alkyl groups, cycloalkyl (alicyclic) groups, alkyl substituted cycloalkyl groups, and cycloalkyl substituted alkyl groups. The term alkyl further includes alkyl groups, which can further include oxygen, nitrogen, sulfur or phosphorous atoms replacing one or more carbons of the hydrocarbon backbone, e.g., oxygen, nitrogen, sulfur or phosphorous atoms. In preferred embodiments, a straight chain or branched chain alkyl has 6 or fewer carbon atoms in its backbone (e.g., $C_1$–$C_6$ for straight chain, $C_3$–$C_6$ for branched chain), and more preferably 4 or fewer. Likewise, preferred cycloalkyls have from 4–7 carbon atoms in their ring structure, and more preferably have 5 or 6 carbons in the ring structure.

Moreover, the term alkyl includes both "unsubstituted alkyls" and "substituted alkyls", the latter of which refers to alkyl moieties having substituents replacing a hydrogen on one or more carbons of the hydrocarbon backbone. Such substituents can include, for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, aryloxy, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkylaryl, or an aromatic or heteroaromatic moiety. Cycloalkyls can be further substituted, e.g., with the substituents described above. An "alkylaryl" moiety is an alkyl substituted with an aryl (e.g., phenylmethyl (benzyl)).

The term "aryl" includes aryl groups, including 5- and 6-membered single-ring aromatic groups that may include from zero to four heteroatoms, for example, benzene, pyrrole, furan, thiophene, imidazole, benzoxazole, benzothiazole, triazole, tetrazole, pyrazole, pyridine, pyrazine, pyridazine and pyrimidine, and the like. Aryl groups also include polycyclic fused aromatic groups such as naphthyl, quinolyl, indolyl, and the like. Those aryl groups having heteroatoms in the ring structure may also be referred to as "aryl heterocycles", "heteroaryls" or "heteroaromatics". The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings which are not aromatic so as to form a polycycle (e.g., tetralin).

The terms "alkenyl" and "alkynyl" include unsaturated aliphatic groups analogous in length and possible substitution to the alkyls described above, but that contain at least one double or triple bond, respectively.

Unless the number of carbons is otherwise specified, "lower alkyl" as used herein means an alkyl group, as defined above, but having from one to five carbon atoms in its backbone structure. Likewise, "lower alkenyl" and "lower alkynyl" have similar chain lengths.

The terms "alkoxyalkyl", "polyaminoalkyl" and "thioalkoxyalkyl" include alkyl groups, as described above, which further include oxygen, nitrogen or sulfur atoms replacing one or more carbons of the hydrocarbon backbone, e.g., oxygen, nitrogen or sulfur atoms.

The terms "polycyclyl" or "polycyclic radical" refer to two or more cyclic rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkyl, alkylaryl, or an aromatic or heteroaromatic moiety.

The term "heterocyclic ring" refers to a ring containing one or more heteroatoms as part of the ring. Examples of "heterocyclic rings" include tetrahydrofuran, furan, ethylene oxide, pyrrolidine, piperidine, thiophene, and pyrrole.

The term "heteroatom" as used herein means an atom of any element other than carbon or hydrogen. Preferred heteroatoms are nitrogen, oxygen, sulfur and phosphorus.

The term "bicyclic ring" includes rings where 2 atoms share more than one ring. Examples of bicyclic rings include bicyclbutane, camphene, decalin, and phthalimide.

The term "carbonyl" includes moieties which contain a carbon double bonded to an oxygen atom. The term "substituted carbonyl" includes groups wherein the carbon of the carbonyl group is further bonded to another carbon or a heteroatom. Examples of substituents include, but are not limited to, alkyl, alkenyl, alkynyl, aryl, halogen, hydroxyl, alkylcarbonyloxy, arylcarbonyloxy, alkoxycarbonyloxy, aryloxycarbonyloxy, alkoxy, aryloxy, aryloxycarbonyloxy, carboxylate, alkylcarbonyl, alkoxycarbonyl, aminocarbonyl, alkylthiocarbonyl, aphosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkylaryl, or an aromatic or heteroaromatic moiety.

The term "thiocarbonyl" includes moieties which contain a carbon double bonded to a sulfur atom. The term "substituted thiocarbonyl" includes groups wherein the carbon of the carbonyl group is further bonded to another carbon or a heteroatom. Examples of substituents include, but are not limited to, alkyl, alkenyl, alkynyl, aryl, halogen, hydroxyl, alkylcarboriyloxy, arylcarbonyloxy, alkoxycarbonyloxy, aryloxycarbonyloxy, alkoxy, aryloxy, aryloxycarbonyloxy, carboxylate, alkylcarbonyl, alkoxycarbonyl, aminocarbonyl, alkylthiocarbonyl, aphosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkylaryl, or an aromatic or heteroaromatic moiety.

Suitable alkanoyl groups include groups having 1 to about 4 or 5 carbonyl groups. Suitable aroyl groups include groups having one or more carbonyl groups as a substituent to an aryl group such as phenyl or other carbocyclic aryl. Suitable alkaroyl groups have one or more alkylcarbonyl groups as a substituent to an aryl group such as phenylacetyl and the like. Suitable carbocyclic aryl groups have 6 or more carbons such as phenyl, naphthyl and the like. Suitable aryloyl groups are carbocyclic aryl groups that are substituted with one or more carbonyl groups, typically 1 or 2 carbonyl groups.

Prodrugs are compounds which are converted in vivo to active forms (see, e.g., R. B. Silverman, 1992, "The Organic Chemistry of Drug Design and Drug Action", Academic Press, Chp. 8). Prodrugs can be used to alter the biodistribution (e.g., to allow compounds which would not typically enter the reactive site of the protease) or the pharmacokinetics for a particular compound. For example, a hydroxyl group, can be esterified, e.g., with a carboxylic acid group to yield an ester. When the ester is administered to a subject, the ester is cleaved, enzymatically or non-enzymatically, reductively or hydrolytically, to reveal the hydroxyl group. Prodrugs may be metabolized in vivo by esterases or by other mechanisms to hydroxyl groups or other advantageous groups. Examples of prodrugs and their uses are well known in the art (See, e.g., Berge et al. (1977) "Pharmaceutical Salts", *J. Pharm. Sci.* 66:1–19). The prodrugs can be prepared in situ during the final isolation and purification of the compounds, or by separately reacting the purified compound in its free acid form or hydroxyl with a suitable esterifying agent. Hydroxyl groups can be converted into esters via treatment with a carboxylic acid. Examples of prodrugs include substituted and unsubstituted, branch or unbranched lower alkyl ester moieties, (e.g., propionoic acid esters), lower alkenyl esters, di-lower alkyl-amino lower-alkyl esters (e.g., dimethylaminoethyl ester), acylamino lower alkyl esters (e.g., acetyloxymethyl ester), acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, di-lower alkyl amides, and hydroxy amides.

It will be noted that the structure of some of the compounds of this invention includes asymmetric carbon atoms. It is to be understood accordingly that the isomers arising from such asymmetry (e.g., all enantiomers and diastereomers) are included within the scope of this invention, unless indicated otherwise. Such isomers can be obtained in substantially pure form by classical separation techniques and by stereochemically controlled synthesis.

The invention also pertains, at least in part, to methods of treating a subject, e.g., a mammal, e.g., a human, for a tetracycline responsive state by administering an effective amount of an aminomethyl tetracycline compound of the invention, e.g., a compound of Formula (I), (III), (III), Table 1, or otherwise described herein.

The language "tetracycline compound responsive state" or "tetracycline responsive state" includes states which can be treated, prevented, or otherwise ameliorated by the administration of a tetracycline compound of the invention, e.g., a 9-aminomethyl tetracycline compound. Tetracycline compound responsive states include bacterial, viral, and fungal infections (including those which are resistant to other tetracycline compounds), cancer (e.g., prostate, breast, colon, lung melanoma and lymph cancers and other disorders characterized by unwanted cellular proliferation, including, but not limited to, those described in U.S. Pat. No. 6,100,248), arthritis, osteoporosis, diabetes, cystic fibrosis, neurological disorders and other states for which tetracycline compounds have been found to be active (see, for example, U.S. Pat. Nos. 5,789,395; 5,834,450; 6,277,061 and 5,532,227, each of which is expressly incorporated herein by reference). Compounds of the invention can be used to prevent or control important mammalian and veterinary diseases such as diarrhea, urinary tract infections, infections of skin and skin structure, ear, nose and throat infections, wound infection, mastitis and the like. In addition, methods for treating neoplasms using tetracycline compounds of the invention are also included (van der Bozert et al., *Cancer Res.,* 48:6686–6690 (1988)). In a further embodiment, the tetracycline responsive state is not a bacterial infection. Other tetracycline compound responsive states include, for example, those described in U.S. Ser. No. 10/196,010.

Tetracycline compound responsive states also include inflammatory process associated states (IPAS). The term "inflammatory process associated state" includes states in which inflammation or inflammatory factors (e.g., matrix metalloproteinases (MMPs), nitric oxide (NO), TNF, interleukins, plasma proteins, cellular defense systems, cytokines, lipid metabolites, proteases, toxic radicals, adhesion molecules, etc.) are involved or are present in an area in aberrant amounts, e.g., in amounts which may be advantageous to alter, e.g. to benefit the subject. The inflammatory process is the response of living tissue to damage. The cause of inflammation may be due to physical damage, chemical substances, micro-organisms, tissue necrosis, cancer or other agents. Acute inflammation is short-lasting, lasting only a few days. If it is longer lasting however, then it may be referred to as chronic inflammation.

IPAS's include inflammatory disorders. Inflammatory disorders are generally characterized by heat, redness, swelling, pain and loss of function. Examples of causes of inflammatory disorders include, but are not limited to, microbial infections (e.g., bacterial and fungal infections), physical agents (e.g., burns, radiation, and trauma), chemical agents (e.g., toxins and caustic substances), tissue necrosis and various types of immunologic reactions.

Examples of inflammatory disorders include, but are not limited to, osteoarthritis, rheumatoid arthritis, acute and chronic infections (bacterial and fungal, including diphtheria and pertussis); acute and chronic bronchitis, sinusitis, and upper respiratory infections, including the common cold; acute and chronic gastroenteritis and colitis; acute and chronic cystitis and urethritis; acute and chronic dermatitis; acute and chronic conjunctivitis; acute and chronic serositis (pericarditis, peritonitis, synovitis, pleuritis and tendinitis);

uremic pericarditis; acute and chronic cholecystis; acute and chronic vaginitis; acute and chronic uveitis; drug reactions; insect bites; burns (thermal, chemical, and electrical); and sunburn.

Tetracycline compound responsive states also include NO associated states. The term "NO associated state" includes states which involve or are associated with nitric oxide (NO) or inducible nitric oxide synthase (iNOS). NO associated state includes states which are characterized by aberrant amounts of NO and/or iNOS. Preferably, the NO associated state can be treated by administering tetracycline compounds of the invention, e.g., compounds of formula I, II, III, Table 1, or otherwise described herein. The disorders, diseases and states described in U.S. Pat. Nos. 6,231,894; 6,015,804; 5,919,774; and 5,789,395 are also included as NO associated states. The entire contents of each of these patents are hereby incorporated herein by reference.

Other examples of NO associated states include, but are not limited to, malaria, senescence, diabetes, vascular stroke, neurodegenerative disorders (Alzheimer's disease, Huntington's disease), cardiac disease (reperfusion-associated injury following infarction), juvenile diabetes, inflammatory disorders, osteoarthritis, rheumatoid arthritis, acute and chronic infections (bacterial, viral, and fungal); cystic fibrosis, acute and chronic bronchitis, sinusitis, and respiratory infections, including the common cold; acute and chronic gastroenteritis and colitis; acute and chronic cystitis and urethritis; acute and chronic dermatitis; acute and chronic conjunctivitis; acute and chronic serositis (pericarditis, peritonitis, synovitis, pleuritis and tendinitis); uremic pericarditis; acute and chronic cholecystis; acute and chronic vaginitis; acute and chronic uveitis; drug reactions; insect bites; burns (thermal, chemical, and electrical); and sunburn.

The term "inflammatory process associated state" also includes, in one embodiment, matrix metalloproteinase associated states (MMPAS). MMPAS include states characterized by aberrant amounts of MMPs or MMP activity. These are also include as tetracycline compound responsive states which may be treated using compounds of the invention, e.g., 9-aminomethyl tetracycline compounds such as those described herein, e.g., in formula I.

Examples of matrix metalloproteinase associated states ("MMPAS's") include, but are not limited to, arteriosclerosis, corneal ulceration, emphysema, osteoarthritis, multiple sclerosis (Liedtke et al., *Ann. Neurol.* 1998, 44:35–46; Chandler et al., *J. Neuroimmunol.* 1997, 72:155–71), osteosarcoma, osteomyelitis, bronchiectasis, chronic pulmonary obstructive disease, skin and eye diseases, periodontitis, osteoporosis, rheumatoid arthritis, ulcerative colitis, inflammatory disorders, tumor growth and invasion (Stetler-Stevenson et al., *Annu. Rev. Cell Biol.* 1993, 9:541–73; Tryggvason et al., *Biochim. Biophys. Acta* 1987, 907:191–217; Li et al., *Mol. Carcinog.* 1998, 22:84–89), metastasis, acute lung injury, stroke, ischemia, diabetes, aortic or vascular aneurysms, skin tissue wounds, dry eye, bone and cartilage degradation (Greenwald et al., *Bone* 1998, 22:33–38; Ryan et al., *Curr. Op. Rheumatol.* 1996, 8;238–247). Other MMPAS include those described in U.S. Pat. Nos. 5,459,135; 5,321,017; 5,308,839; 5,258,371; 4,935,412; 4,704,383, 4,666,897, and RE 34,656, incorporated herein by reference in their entirety.

In another embodiment, the tetracycline compound responsive state is cancer. Examples of cancers which the tetracycline compounds of the invention may be useful to treat include all solid tumors, i.e., carcinomas e.g., adenocarcinomas, and sarcomas. Adenocarcinomas are carcinomas derived from glandular tissue or in which the tumor cells form recognizable glandular structures. Sarcomas broadly include tumors whose cells are embedded in a fibrillar or homogeneous substance like embryonic connective tissue. Examples of carcinomas which may be treated using the methods of the invention include, but are not limited to, carcinomas of the prostate, breast, ovary, testis, lung, colon, and breast. The methods of the invention are not limited to the treatment of these tumor types, but extend to any solid tumor derived from any organ system. Examples of treatable cancers include, but are not limited to, colon cancer, bladder cancer, breast cancer, melanoma, ovarian carcinoma, prostatic carcinoma, lung cancer, and a variety of other cancers as well. The methods of the invention also cause the inhibition of cancer growth in adenocarcinomas, such as, for example, those of the prostate, breast, kidney, ovary, testes, and colon.

In an embodiment, the tetracycline responsive state of the invention is cancer. The invention pertains to a method for treating a subject suffering or at risk of suffering from cancer, by administering an effective amount of a substituted tetracycline compound, such that inhibition cancer cell growth occurs, i.e., cellular proliferation, invasiveness, metastasis, or tumor incidence is decreased, slowed, or stopped. The inhibition may result from inhibition of an inflammatory process, down-regulation of an inflammatory process, some other mechanism, or a combination of mechanisms. Alternatively, the tetracycline compounds may be useful for preventing cancer recurrence, for example, to treat residual cancer following surgical resection or radiation therapy. The tetracycline compounds useful according to the invention are especially advantageous as they are substantially non-toxic compared to other cancer treatments. In a further embodiment, the compounds of the invention are administered in combination with standard cancer therapy, such as, but not limited to, chemotherapy.

The language "in combination with" another therapeutic agent or treatment includes co-administration of the tetracycline compound and with the other therapeutic agent or treatment, administration of the tetracycline compound first, followed by the other therapeutic agent or treatment and administration of the other therapeutic agent or treatment first, followed by the tetracycline compound. The other therapeutic agent may be any agent which is known in the art to treat, prevent, or reduce the symptoms of a tetracycline responsive state. Furthermore, the other therapeutic agent may be any agent of benefit to the patient when administered in combination with the administration of an tetracycline compound. In one embodiment, the cancers treated by methods of the invention include those described in U.S. Pat. Nos. 6,100,248; 5,843,925; 5,837,696; or 5,668,122, incorporated herein by reference in their entirety.

In another embodiment, the tetracycline compound responsive state is diabetes, e.g., juvenile diabetes, diabetes mellitus, diabetes type I, diabetes type II, diabetic ulcers, or other diabetic complications. In a further embodiment, protein glycosylation is not affected by the administration of the tetracycline compounds of the invention. In another embodiment, the tetracycline compound of the invention is administered in combination with standard diabetic therapies, such as, but not limited to insulin therapy. In a further embodiment, the IPAS includes disorders described in U.S. Pat. Nos. 5,929,055; and 5,532,227, incorporated herein by reference in their entirety.

In another embodiment, the tetracycline compound responsive state is a bone mass disorder. Bone mass disorders include disorders where a subjects bones are disorders and states where the formation, repair or remodeling of bone is advantageous. For examples bone mass disorders include osteoporosis (e.g., a decrease in bone strength and density), bone fractures, bone formation associated with surgical procedures (e.g., facial reconstruction), osteogenesis imperfecta (brittle bone disease), hypophosphatasia, Paget's disease, fibrous dysplasia, osteopetrosis, myeloma bone disease, and the depletion of calcium in bone, such as that which is related to primary hyperparathyroidism. Bone mass disorders include all states in which the formation, repair or remodeling of bone is advantageous to the subject as well as all other disorders associated with the bones or skeletal system of a subject which can be treated with the tetracycline compounds of the invention. In a further embodiment, the bone mass disorders include those described in U.S. Pat. Nos. 5,459,135; 5,231,017; 5,998,390; 5,770,588; RE 34,656; 5,308,839; 4,925,833; 3,304,227; and 4,666,897, each of which is hereby incorporated herein by reference in its entirety.

In another embodiment, the tetracycline compound responsive state is acute lung injury. Acute lung injuries include adult respiratory distress syndrome (ARDS), post-pump syndrome (PPS), and trauma. Trauma includes any injury to living tissue caused by an extrinsic agent or event. Examples of trauma include, but are not limited to, crush injuries, contact with a hard surface, or cutting or other damage to the lungs.

The invention also pertains to a method for treating acute lung injury by administering a tetracycline compound of the invention.

The tetracycline responsive states of the invention also include chronic lung disorders. The invention pertains to methods for treating chronic lung disorders by administering a tetracycline compound, such as those described herein. The method includes administering to a subject an effective amount of a substituted tetracycline compound such that the chronic lung disorder is treated. Examples of chronic lung disorders include, but are not limited, to asthma, cystic fibrosis, and emphysema. In a further embodiment, the tetracycline compounds of the invention used to treat acute and/or chronic lung disorders such as those described in U.S. Pat. Nos. 5,977,091; 6,043,231; 5,523,297; and 5,773,430, each of which is hereby incorporated herein by reference in its entirety.

In yet another embodiment, the tetracycline compound responsive state is ischemia, stroke, or ischemic stroke. The invention also pertains to a method for treating ischemia, stroke, or ischemic stroke by administering an effective amount of a substituted tetracycline compound of the invention. In a further embodiment, the tetracycline compounds of the invention are used to treat such disorders as described in U.S. Pat. Nos. 6,231,894; 5,773,430; 5,919,775 or 5,789,395, incorporated herein by reference.

In another embodiment, the tetracycline compound responsive state is a skin wound. The invention also pertains, at least in part, to a method for improving the healing response of the epithelialized tissue (e.g., skin, mucosae) to acute traumatic injury (e.g., cut, burn, scrape, etc.). The method may include using a tetracycline compound of the invention (which may or may not have antibacterial activity) to improve the capacity of the epithelialized tissue to heal acute wounds. The method may increase the rate of collagen accumulation of the healing tissue. The method may also decrease the proteolytic activity in the epthithelialized tissue by decreasing the collagenolytic and/or gelatinolytic activity of MMPs. In a further embodiment, the tetracycline compound of the invention is administered to the surface of the skin (e.g., topically). In a further embodiment, the tetracycline compound of the invention is used to treat a skin wound, and other such disorders as described in, for example, U.S. Pat. Nos. 5,827,840; 4,704,383; 4,935,412; 5,258,371; 5,308,8391 5,459,135; 5,532,227; and 6,015,804; each of which is incorporated herein by reference in its entirety.

Examples of tetracycline responsive states also include neurological disorders which include both neuropsychiatric and neurodegenerative disorders, but are not limited to, such as Alzheimer's disease, dementias related to Alzheimer's disease (such as Pick's disease), Parkinson's and other Lewy diffuse body diseases, senile dementia, Huntington's disease, Gilles de la Tourette's syndrome, multiple sclerosis, amyotrophic lateral sclerosis (ALS), progressive supranuclear palsy, epilepsy, and Creutzfeldt-Jakob disease; autonomic function disorders such as hypertension and sleep disorders, and neuropsychiatric disorders, such as depression, schizophrenia, schizoaffective disorder, Korsakoff's psychosis, mania, anxiety disorders, or phobic disorders; learning or memory disorders, e.g., amnesia or age-related memory loss, attention deficit disorder, dysthymic disorder, major depressive disorder, mania, obsessive-compulsive disorder, psychoactive substance use disorders, anxiety, phobias, panic disorder, as well as bipolar affective disorder, e.g., severe bipolar affective (mood) disorder (BP-1), bipolar affective neurological disorders, e.g., migraine and obesity. Further neurological disorders include, for example, those listed in the American Psychiatric Association's Diagnostic and Statistical manual of Mental Disorders (DSM), the most current version of which is incorporated herein by reference in its entirety.

In yet another embodiment, the tetracycline compound responsive state is an aortic or vascular aneurysm in vascular tissue of a subject (e.g., a subject having or at risk of having an aortic or vascular aneurysm, etc.). The tetracycline compound may by effective to reduce the size of the vascular aneurysm or it may be administered to the subject prior to the onset of the vascular aneurysm such that the aneurysm is prevented. In one embodiment, the vascular tissue is an artery, e.g., the aorta, e.g., the abdominal aorta. In a further embodiment, the tetracycline compounds of the invention are used to treat disorders described in U.S. Pat. Nos. 6,043,225 and 5,834,449, incorporated herein by reference in their entirety.

Bacterial infections may be caused by a wide variety of gram positive and gram negative bacteria. The compounds of the invention are useful as antibiotics against organisms which are resistant to other tetracycline compounds. The antibiotic activity of the tetracycline compounds of the invention may be determined using the method discussed in Example 2, or by using the in vitro standard broth dilution method described in Waitz, J. A., *National Commission for Clinical Laboratory Standards, Document* M7-A2, vol. 10, no. 8, pp. 13–20, $2^{nd}$ edition, Villanova, PA (1990).

The tetracycline compounds of the invention may also be used to treat infections traditionally treated with tetracycline compounds such as, for example, rickettsiae; a number of gram-positive and gram-negative bacteria; and the agents responsible for lymphogranuloma venereum, inclusion conjunctivitis, psittacosis. The tetracycline compounds may be used to treat infections of, e.g., *K. pneumoniae, Salmonella, E. hirae, A. baumanii, B. catarrhalis, H. influenzae, P. aeruginosa, E. faecium, E. coli, S. aureus* or *E. faecalis*. In one embodiment, the tetracycline compound is used to treat a bacterial infection that is resistant to other tetracycline antibiotic compounds. The tetracycline compound of the invention may be administered with a pharmaceutically acceptable carrier.

The language "effective amount" of the compound is that amount necessary or sufficient to treat or prevent a tetracycline compound responsive state. The effective amount can vary depending on such factors as the size and weight of the subject, the type of illness, or the particular tetracycline compound. For example, the choice of the tetracycline compound can affect what constitutes an "effective amount". One of ordinary skill in the art would be able to study the aforementioned factors and make the determination regarding the effective amount of the tetracycline compound without undue experimentation.

In an embodiment, the invention pertains to pharmaceutical composition comprising a tetracycline compound of the invention, e.g., a compound of Formula (I), (II), (III), or otherwise described herein. Preferably, the tetracycline compound is provided in an effective amount, e.g., effective to treat a tetracycline responsive state in a subject, e.g., a mammal, e.g., a human. In a further embodiment, the pharmaceutical composition of the invention also comprises an appropriate pharmaceutically acceptable carrier.

The language "pharmaceutically acceptable carrier" includes substances capable of being coadministered with the tetracycline compound(s), and which allow both to perform their intended function, e.g., treat or prevent a tetracycline compound responsive state. Suitable pharmaceutically acceptable carriers include but are not limited to water, salt solutions, alcohol, vegetable oils, polyethylene glycols, gelatin, lactose, amylose, magnesium stearate, talc, silicic acid, viscous paraffin, perfume oil, fatty acid monoglycerides and diglycerides, petroethral fatty acid esters, hydroxymethyl-cellulose, polyvinylpyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously react with the active compounds of the invention.

The tetracycline compounds of the invention that are basic in nature are capable of forming a wide variety of salts with various inorganic and organic acids. The acids that may be used to prepare pharmaceutically acceptable acid addition salts of the tetracycline compounds of the invention that are basic in nature are those that form non-toxic acid addition salts, ie., salts containing pharmaceutically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and palmoate [i.e., 1,1'-methylene-bis-(2-hydroxy-3-naphthoate)] salts. Although such salts must be pharmaceutically acceptable for administration to a subject, e.g., a mammal, it is often desirable in practice to initially isolate a tetracycline compound of the invention from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained.

The tetracycline compounds of the invention that are acidic in nature are capable of forming a wide variety of base salts. The chemical bases that may be used as reagents to prepare pharmaceutically acceptable base salts of those tetracycline compounds of the invention that are acidic in nature are those that form non-toxic base salts with such compounds. Such non-toxic base salts include, but are not limited to those derived from such pharmaceutically acceptable cations such as alkali metal cations (e.g., potassium and sodium) and alkaline earth metal cations (e.g., calcium and magnesium), ammonium or water-soluble amine addition salts such as N-methylglucamine-(meglumine), and the lower alkanolammonium and other base salts of pharmaceutically acceptable organic amines. The pharmaceutically acceptable base addition salts of tetracycline compounds of the invention that are acidic in nature may be formed with pharmaceutically acceptable cations by conventional methods. Thus, these salts may be readily prepared by treating the tetracycline compound of the invention with an aqueous solution of the desired pharmaceutically acceptable cation and evaporating the resulting solution to dryness, preferably under reduced pressure. Alternatively, a lower alkyl alcohol solution of the tetracycline compound of the invention may be mixed with an alkoxide of the desired metal and the solution subsequently evaporated to dryness.

The preparation of other tetracycline compounds of the invention not specifically described in the foregoing experimental section can be accomplished using combinations of the reactions described above that will be apparent to those skilled in the art.

The tetracycline compounds of the invention and pharmaceutically acceptable salts thereof can be administered via either the oral, parenteral or topical routes. In general, these compounds are most desirably administered in effective dosages, depending upon the weight and condition of the subject being treated and the particular route of administration chosen. Variations may occur depending upon the species of the subject being treated and its individual response to said medicament, as well as on the type of pharmaceutical formulation chosen and the time period and interval at which such administration is carried out.

The pharmaceutical compositions of the invention may be administered alone or in combination with other known compositions for treating tetracycline responsive states in subjects, e.g., mammals. The subjects may be suffering from or at risk of suffering from a tetracycline responsive state. Examples of subjects include pets (e.g., cats, dogs, ferrets, etc.), farm animals (cows, sheep, pigs, horses, goats, etc.), lab animals (rats, mice, monkeys, etc.), and primates (chimpanzees, humans, gorillas).

The language "in combination with" a known composition is intended to include simultaneous administration of the composition of the invention and the known composition, administration of the composition of the invention first, followed by the known composition and administration of the known composition first, followed by the composition of the invention. Any of the therapeutically composition known in the art for treating tetracycline responsive states can be used in the methods of the invention.

The compounds of the invention may be administered alone or in combination with pharmaceutically acceptable carriers or diluents by any of the routes previously mentioned, and the administration may be carried out in single or multiple doses. For example, the novel therapeutic agents of this invention can be administered advantageously in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various non-toxic organic solvents, etc. Moreover, oral pharmaceutical compositions can be suitably sweetened and/or flavored. In general, the therapeutically-effective compounds of this invention are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration (including intraperitoneal, subcutaneous, intravenous, intradermal or intramuscular injection), solutions of a therapeutic compound of the present invention in either sesame or peanut oil or in aqueous propylene glycol may be employed. The aqueous solutions should be suitably buffered (preferably pH greater than 8) if necessary and the liquid diluent first rendered isotonic. These aqueous solutions are suitable for intravenous injection purposes. The oily solutions are suitable for intraarticular, intramuscular and subcutaneous injection purposes. The preparation of all these solutions under sterile conditions is readily accomplished by standard pharmaceutical techniques well known to those skilled in the art. For parenteral application, examples of suitable preparations include solutions, preferably oily or aqueous solutions as well as suspensions, emulsions, or implants, including suppositories. Therapeutic compounds may be formulated in sterile form in multiple or single dose formats such as being dispersed in a fluid carrier such as sterile physiological saline or 5% saline dextrose solutions commonly used with injectables.

Additionally, it is also possible to administer the compounds of the present invention topically when treating inflammatory conditions of the skin. Examples of methods of topical administration include transdermal, buccal or sublingual application. For topical applications, therapeutic compounds can be suitably admixed in a pharmacologically inert topical carrier such as a gel, an ointment, a lotion or a cream. Such topical carriers include water, glycerol, alcohol, propylene glycol, fatty alcohols, triglycerides, fatty acid esters, or mineral oils. Other possible topical carriers are liquid petrolatum, isopropylpalmitate, polyethylene glycol, ethanol 95%, polyoxyethylene monolauriate 5% in water, sodium lauryl sulfate 5% in water, and the like. In addition, materials such as anti-oxidants, humectants, viscosity stabilizers and the like also may be added if desired.

For enteral application, particularly suitable are tablets, dragees or capsules having talc and/or carbohydrate carrier binder or the like, the carrier preferably being lactose and/or corn starch and/or potato starch. A syrup, elixir or the like can be used wherein a sweetened vehicle is employed. Sustained release compositions can be formulated including those wherein the active component is protected with differentially degradable coatings, e.g., by microencapsulation, multiple coatings, etc.

In addition to treatment of human subjects, the therapeutic methods of the invention also will have significant veterinary applications, e.g. for treatment of livestock such as cattle, sheep, goats, cows, swine and the like; poultry such as chickens, ducks, geese, turkeys and the like; horses; and pets such as dogs and cats. Also, the compounds of the invention may be used to treat non-animal subjects, such as plants.

It will be appreciated that the actual preferred amounts of active compounds used in a given therapy will vary according to the specific compound being utilized, the particular compositions formulated, the mode of application, the particular site of administration, etc. Optimal administration rates for a given protocol of administration can be readily ascertained by those skilled in the art using conventional dosage determination tests conducted with regard to the foregoing guidelines.

In general, compounds of the invention for treatment may, in certain embodiments, be administered to a subject in dosages used in prior tetracycline therapies. See, for example, the *Physicians' Desk Reference*. For example, a suitable effective dose of one or more compounds of the invention will be in the range of from 0.01 to 100 milligrams per kilogram of body weight of recipient per day, preferably in the range of from 0.1 to 50 milligrams per kilogram body weight of recipient per day, more preferably in the range of 1 to 20 milligrams per kilogram body weight of recipient per day. The desired dose is suitably administered once daily, or several sub-doses, e.g. 2 to 5 sub-doses, are administered at appropriate intervals through the day, or other appropriate schedule.

It will also be understood that normal, conventionally known precautions will be taken regarding the administration of tetracyclines generally to ensure their efficacy under normal use circumstances. Especially when employed for therapeutic treatment of humans and animals in vivo, the practitioner should take all sensible precautions to avoid conventionally known contradictions and toxic effects. Thus, the conventionally recognized adverse reactions of gastrointestinal distress and inflammations, the renal toxicity, hypersensitivity reactions, changes in blood, and impairment of absorption through aluminum, calcium, and magnesium ions should be duly considered in the conventional manner.

The invention is further illustrated by the following examples, which should not be construed as further limiting.

EXEMPLIFICATION OF THE INVENTION

Example 1

Synthesis of 9-Aminomethyl Minocycline and Derivatives Thereof

Trifluoroacetic acid (1 L) was charged into a 2 L flask under argon and minocycline. HCl (200 g, 1 eq) and N-hydroxymethylphthalimide (100 g) were added to the flask while stirring. Once the entire solid dissolved, $H_2SO_4$ (200 mL) was added to the reaction. The reaction was heated to 40–50° C. for 5–6 hours. N-hydroxymethylamine (100 g) was added portionwise. When HPLC analysis confirmed that all the starting material was converted to 2,9-bis-aminomethylphthalimidominocycline, the mixture was precipitated out of 4 L of acetone. An exotherm of 15–20° C. was observed. After 1 hour of stirring, the solid was filtered, washed with acetone (200 ml), and dried with the aid of a latex rubber dam. The solid was reslurried in a methanol (1 L)/t-BME (2 L) mixture and the pH was adjusted to 3 using triethylamine. The solid was filtered and washed with 50 mL of methanol. The yield was 97% of 2,9-bis-aminomethylphthalimideminocycline.

2,9-bis-aminomethylphthalimideminocycline (100 g) was suspended in 2M solution of methylamine in methanol (10 eq). The reaction was stirred at room temperature for 2–3 hours, at which point HPLC analysis confirmed total conversion of the starting material to 2,9-bis aminomethylminocycline. The reaction mixture was poured into t-BME (5 volumes), and stirred for thirty minutes. Next, the suspension was filtered and washed with t-BME (200 mL) to isolate the desired product, 2,9-bis-aminomethylminocycline.

2,9-bis-aminomethylminocycline (40 g) was slurried in 200 mL water/methanol 1/9 and the pH was adjusted to 3 by the dropwise addition of trifluoroacetic acid. The mixture was heated to 40° C. for 1–2 hours. When HPLC analysis confirmed the hydrolysis of 2,9-bis-aminomethylminocycline to 9-aminomethylminocycline, the reaction was allowed to return to room temperature and the pH was adjusted to 7 using triethylamine. Isopropyl alcohol (200 mL) was added to precipitate out the solid. The product was filtered and washed with 50 mL IPA followed by 100 mL diethyl ether and dried under reduced pressure toisolate 9-aminomethylminocycline.

9-[(Benzylamino)-methyl]-minocycline dihydrochloride

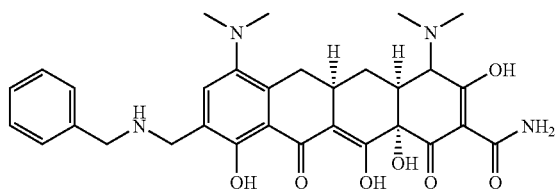

To 1.0 mmol (600 mg) of 9-(aminomethyl)-minocycline dihydrochloride and in 5 mL of dimethylformamide was added 0.2 mmol (5 mg) of indium trichloride and 1.5 mmol (160 mg) of benzaldehyde at room temperature. After 30 minutes of shaking, 2 mmol (424 mg) of sodium triacetoxyborohydride was added and the reaction was monitored by HPLC. After 1.5 hours, 3 equivalents of triethylamine and 1 equivalent of sodium triacetoxyborohydride. The reaction was complete after 3 hours. The solvent was removed in vacuo and the crude product was purified by preparative HPLC to yield 60 mg of 9-[(benzylamino)-methyl]-minocycline dihydrochloride. LCMS (MH+)=577.

9-[(2,2 dimethyl-propyl amino)-methyl]-minocycline dihydrochloride 9-dimethylaminominocycline (200 mg, 1 eq.), DMF, and trimethylacetaldehyde (45 μl, 1 eq.) were combined in 40 mL flasks and stirred. Triethylamine (150 μL, 3 eq.) was then added. After stirring at room temperature for several minutes, NaBH(OAc)$_3$ (175 mg, 2 eq.) and InCl$_3$ (9 mg, 0.1 eq.) was added. After one hour, the reactions were clear and red. Liquid chromatography showed a single product for the reaction. The reaction was quenched with methanol, the solvent was removed, and the product was purified using column chromatography.

9-[3,4-(Methylenedioxo)phenyl-ureido]-methylminocycline dihydrochloride

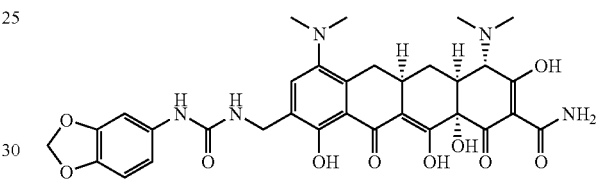

To 0.25 mmol (150 mg) of 9-(aminomethyl)-minocycline dihydrochloride and 2 equivalents of triethylamine in 3 mL of dimethylformamide was added 0.5 mmol (81.5 mg) of 3,4-(methylenedioxo)phenyl isocyanate at room temperature. Solution was shaken until reaction was complete (3 hours). Solvent was removed in vacuo and crude product was purified by preparative HPLC to yield 66 mg of 9-[3,4-(methylenedioxo)phenyl-ureido]-methylminocycline dihydrochloride. Yield 41%. LCMS (MH+)=650.

9-[4-(Trifluoromethoxy)phenyl-ureido]-methylminocycline dihydrochloride

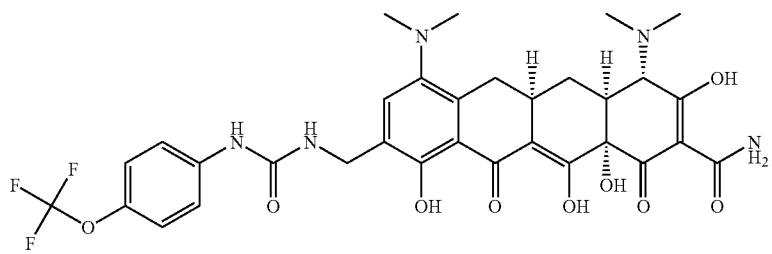

To 0.25 mmol (150 mg) of 9-(aminomethyl)-minocycline dihydrochloride and 2 equivalents of triethylamine in 3 mL of dimethylformamide was added 0.5 mmol (101.5 mg) of 4-(trifluoromethoxy)phenyl isocyanate at room temperature. The solution was shaken until the reaction was complete (3 hours). Solvent was removed in vacuo and crude product was purified by preparative HPLC to yield 68 mg of 9-[4-

(trifluoromethoxy)phenyl-ureido]-methylminocycline dihydrochloride. Yield 39%. LCMS (MH+)=690.

7-[(Bis-dimethoxymethyl-amino)-methyl]-sancycline dihydrochloride

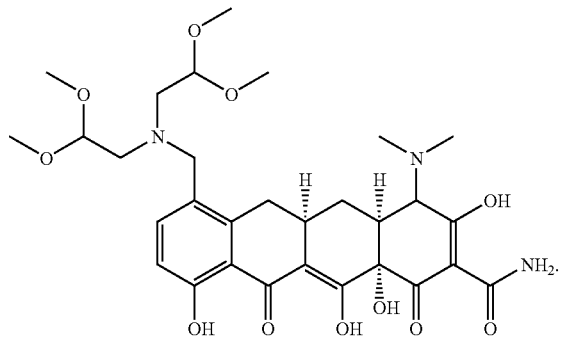

To 1.34 mmol (1 g) of 7-(aminomethyl)-sancycline dihydrochloride and 2 equivalents of triethylamine in 5 mL of dimethylformamide was added 0.134 mmol (29 mg) of indium trichloride and 2.68 mmol (465 mg) of 60% aqueous dimethoxyacetaldehyde at room temperature. After 30 minutes of shaking, 2.68 mmol (568 mg) of sodium triacetoxyborohydride was added and the reaction was monitored by HPLC. The reaction was complete after 1 hour. The solvent was removed in vacuo and the crude product was purified by preparative HPLC to yield 100 mg of 7-[(Bis-dimethoxymethyl-amino)-methyl]-sancycline dihydrochloride. LCMS (MH+)=620.

9-(2'-Phenyl-ethyl-1'-amino)-methyl]-doxycycline

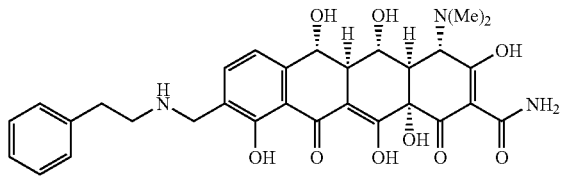

Under an $N_2$ atmosphere, a stirred solution of 9-aminomethyldoxycycline dihydrochloride (1.21 g, 2.21 mmol) in DMF (10 mL), was treated with $InCl_3$ (0.076 g, 0.34 mmol) and phenylacetaldehyde (0.511 mL; 4.4 mmol). HPLC and LCMS monitoring of the reaction indicated the complete consumption of the starting material over the course of 12 hours. The products were both the mono- (major) and bis- (minor) substituted aminodoxycyclines. Methanol (10 mL) was added to quench the reaction. The reaction mixture was filtered through a bed of Celite, the celite washed with methanol (2×5 mL), and the combined organic layer was concentrated to about 7–8 mL and diluted with ether. The resulting amorphous solid was filtered, washed with ether (6×15 mL) and dried under vacuum to afford a red powder, which was purified by preparative HPLC. The final product was characterized by HPLC, MS, and $^1H$ NMR spectroscopic methods. MS (m/z): Theor. 577.24; Found: 578.17 (M+1).

Example 2

In Vitro Minimum Inhibitory Concentration (MIC) Assay

The following assay is used to determine the efficacy of tetracycline derivatives compounds against common bacteria. 2 mg of each compound is dissolved in 100 µl of DMSO. The solution is then added to cation-adjusted Mueller Hinton broth (CAMHB), which results in a final compound concentration of 200 µg per ml. The compound solutions are diluted to 50 µL volumes, with a test compound concentration of 0.098 µg/ml. Optical density (OD) determinations are made from fresh log-phase broth cultures of the test strains. Dilutions are made to achieve a final cell density of $1\times10^6$ CFU/ml. At OD=1, cell densities for different genera should be approximately:

| | |
|---|---|
| E. coli | $1 \times 10^9$ CFU/ml |
| S. aureus | $5 \times 10^8$ CFU/ml |
| Enterococcus sp. | $2.5 \times 10^9$ CFU/ml |

50 µl of the cell suspensions are added to each well of microtiter plates. The final cell density should be approximately $5\times10^5$ CFU/ml. These plates are incubated at 35° C. in an ambient air incubator for approximately 18 hr. The plates are read with a microplate reader and are visually inspected when necessary. The MIC is defined as the lowest concentration of the compound that inhibits growth.

EQUIVALENTS

Those skilled in the art will recognize, or be able to ascertain using no more than routine experimentation, numerous equivalents to the specific procedures described herein. Such equivalents are considered to be within the scope of the present invention and are covered by the following claims. The contents of all references, patents, and patent applications cited throughout this application are hereby incorporated by reference. The appropriate components, processes, and methods of those patents, applications and other documents may be selected for the present invention and embodiments thereof.

The application is related to "9-Substituted Minocycline Compounds," WO 02/04406, filed Jun. 29, 2001, the entire contents of which are hereby incorporated herein by reference.

The invention claimed is:
1. A tetracycline compound of formula (III):

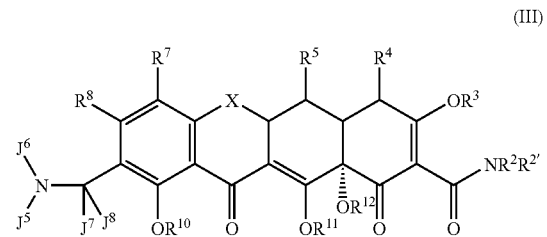

wherein:
$J^5$ and $J^6$ are each independently hydrogen, alkyl, alkenyl, alkynyl, aryl, sulfonyl, acyl, alkoxycarbonyl, alkaminocarbonyl, alkaminothiocarbonyl, substituted thiocarbonyl, substituted carbonyl, alkoxythiocarbonyl, or linked to form a ring;
$J^7$ and $J^8$ are each alkyl, halogen, or hydrogen;
X is $CR^{6'}R^6$;
$R^2$, $R^{2'}$, $R^{4'}$, and $R^{4''}$ are each independently hydrogen, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;
$R^4$ is $NR^{4'}R^{4''}$, alkyl, alkenyl, alkynyl, aryl, hydroxyl, halogen, or hydrogen;

$R^3$, $R^{10}$, $R^{11}$ and $R^{12}$ are each hydrogen or a pro-drug moiety;

$R^5$ is hydroxyl, hydrogen, thiol, alkanoyl, aroyl, alkaroyl, aryl, heteroaromatic, alkyl, alkenyl, alkynyl, alkoxy, alkylthio, alkylsulfinyl, alkylsulfonyl, alkylamino, arylalkyl, alkyl carbonyloxy, or aryl carbonyloxy;

$R^6$ and $R^{6'}$ are each independently hydrogen, methylene, absent, hydroxyl, halogen, thiol, alkyl, alkenyl, alkynyl, aryl, alkoxy, alkylthio, alkylsulfinyl, alkylsulfonyl, alkylamino, or an arylalkyl;

$R^7$ is hydrogen, ethyl, phenyl, 4-t-butylphenyl, t-butylaminophenyl or dimethylamino;

$R^8$ is hydrogen, hydroxyl, halogen, thiol, alkyl, alkenyl, alkynyl, aryl, alkoxy, alkylthio, alkylsulfinyl, alkylsulfonyl, alkylamino, or an arylalkyl;

$R^{13}$ is hydrogen, hydroxyl, alkyl, alkenyl, alkynyl, alkoxy, alkylthio, alkylsulfinyl, alkylsulfonyl, alkylamino, or an arylalkyl; and pharmaceutically acceptable salts thereof.

2. The tetracycline compound of claim 1, wherein $R^4$ is $NR^{4'}R^{4''}$, X is $CR^6R^{6'}$; $R^2$, $R^{2'}$, $R^6$, $R^{6'}$, $R^8$, $R^{10}$, $R^{11}$, and $R^{12}$ are each hydrogen; $R^{4'}$ and $R^{4''}$ are lower alkyl; and $R^5$ is hydroxyl or hydrogen.

3. The tetracycline compound of claim 2, wherein $R^{4'}$ and $R^{4''}$ are each methyl and $R^5$ is hydrogen.

4. The tetracycline compound of claim 1, wherein $J^7$ and $J^8$ are hydrogen.

5. The tetracycline compound of claim 1, wherein $J^5$ is substituted or unsubstituted alkyl.

6. The tetracycline compound of claim 1, wherein $J^5$ is sulfonyl.

7. The tetracycline compound of claim 1, wherein $J^5$ and $J^6$ are linked to form a ring.

8. The tetracycline compound of claim 1, wherein $J^5$ is heteroaryl.

9. The tetracycline compound of claim 1, wherein $J^5$ is substituted carbonyl.

10. The tetracycline compound of claim 1, wherein said compound is selected from the group consisting of:

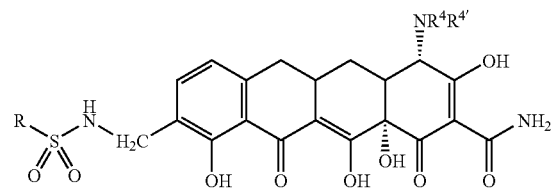

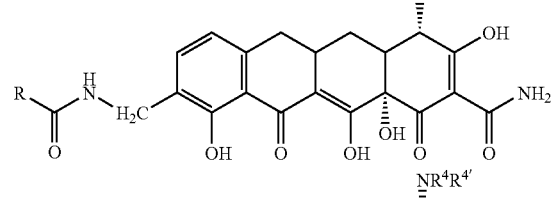

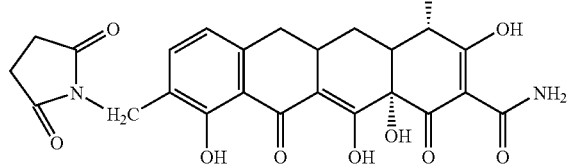

-continued

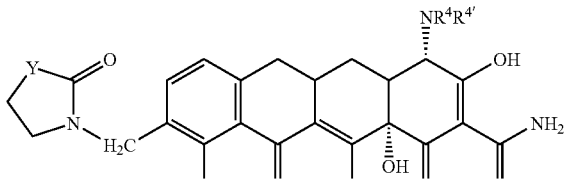

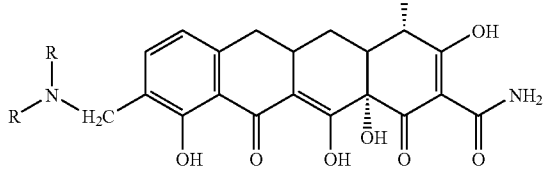

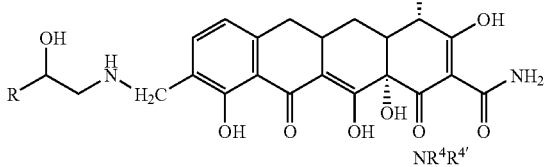

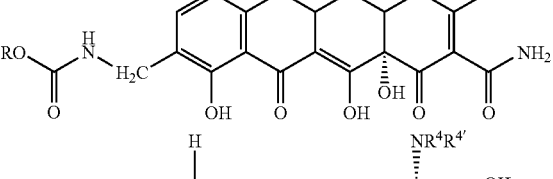

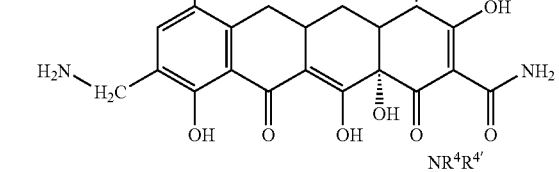

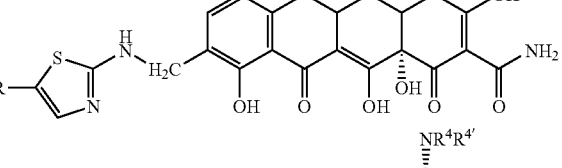

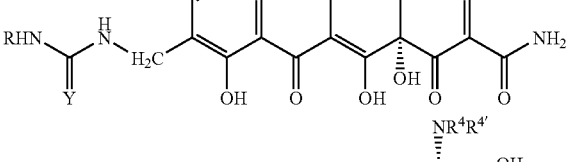

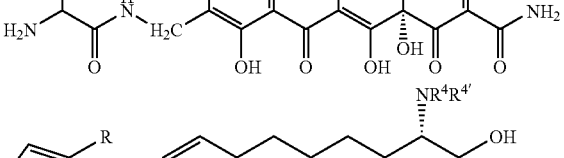

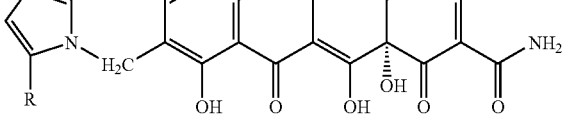

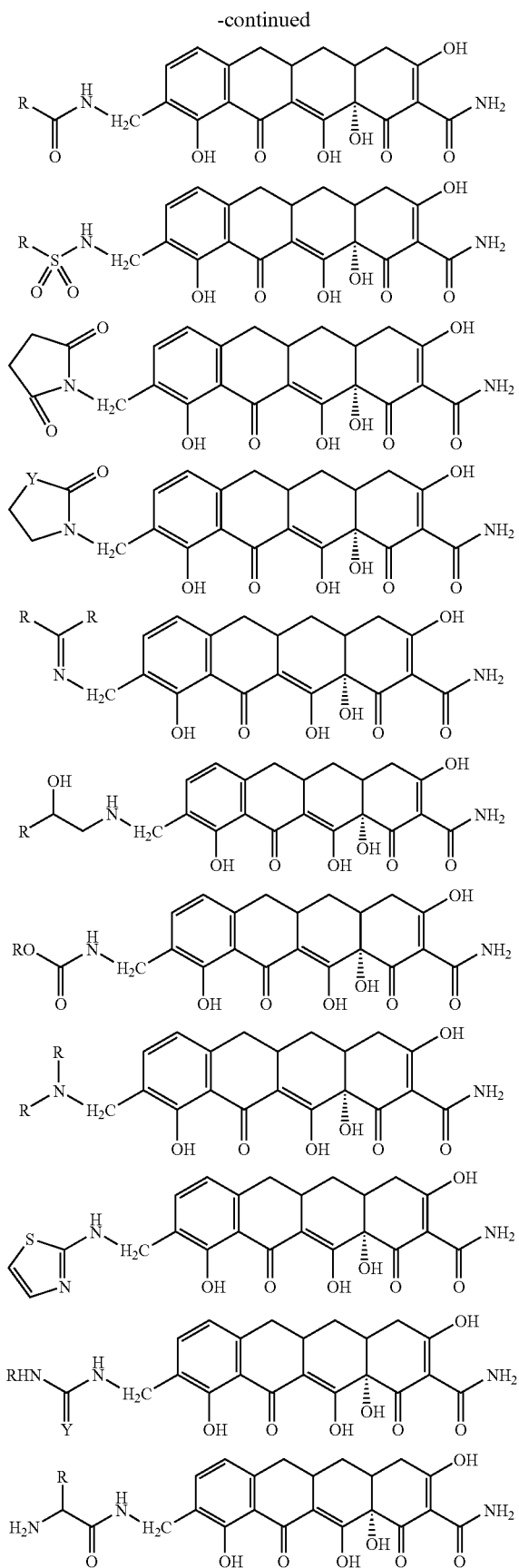
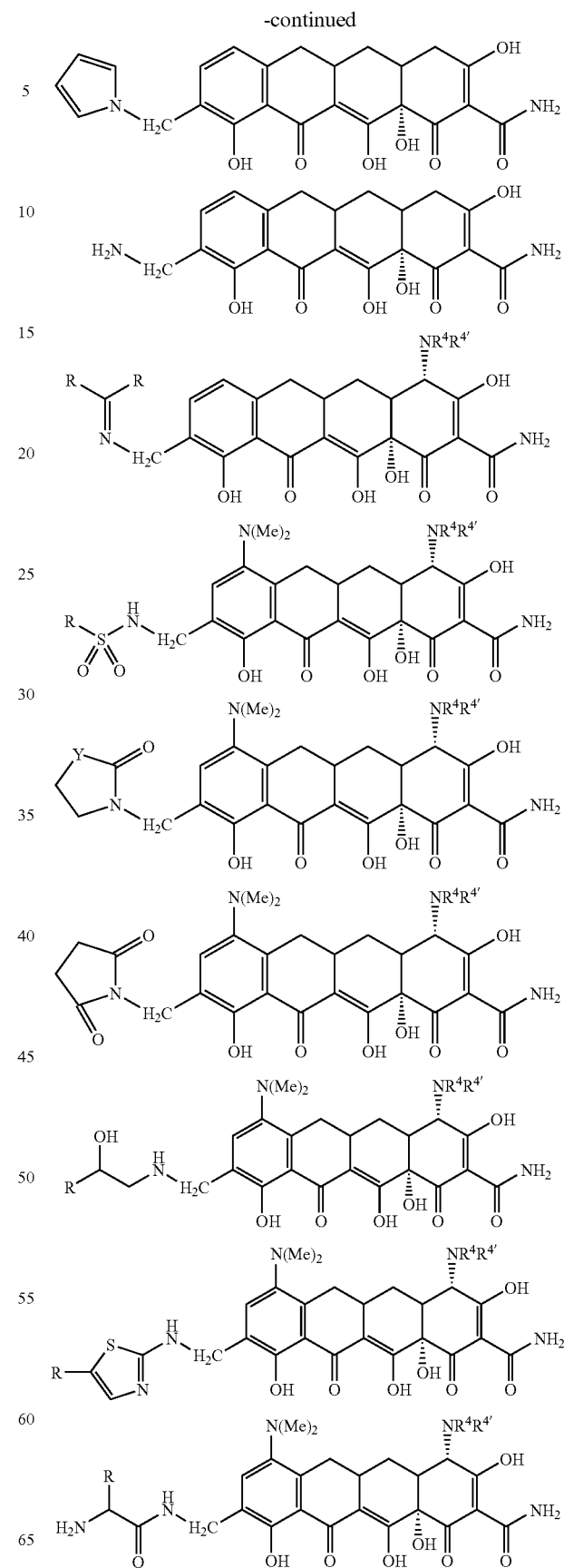

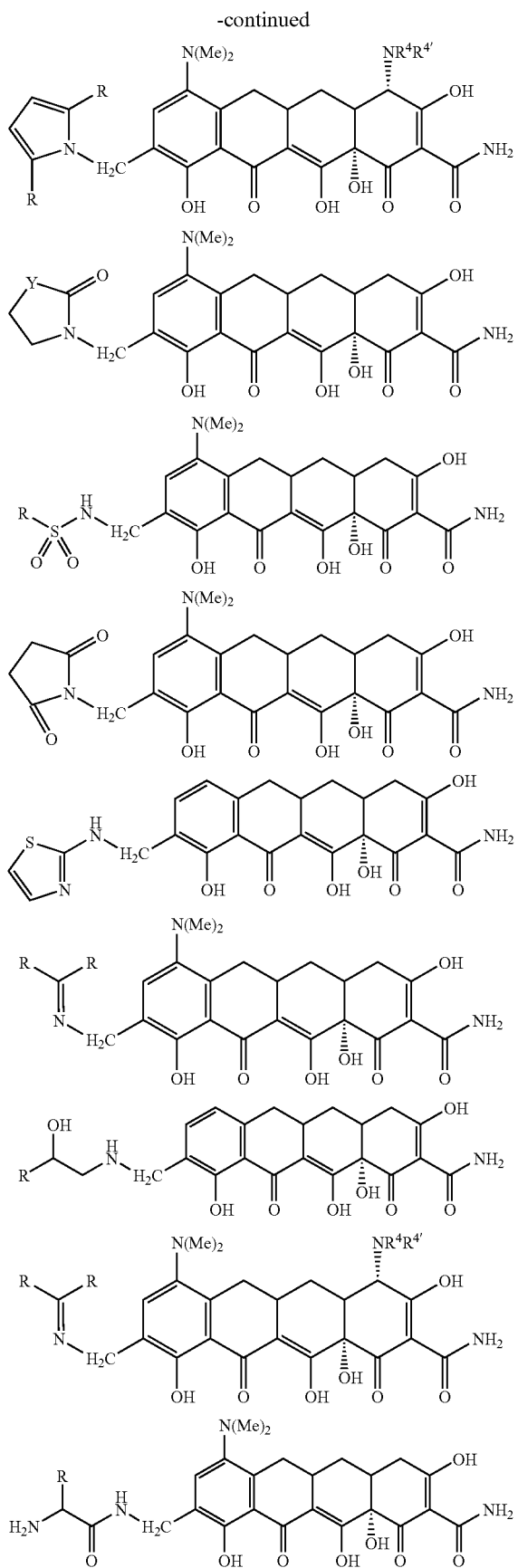
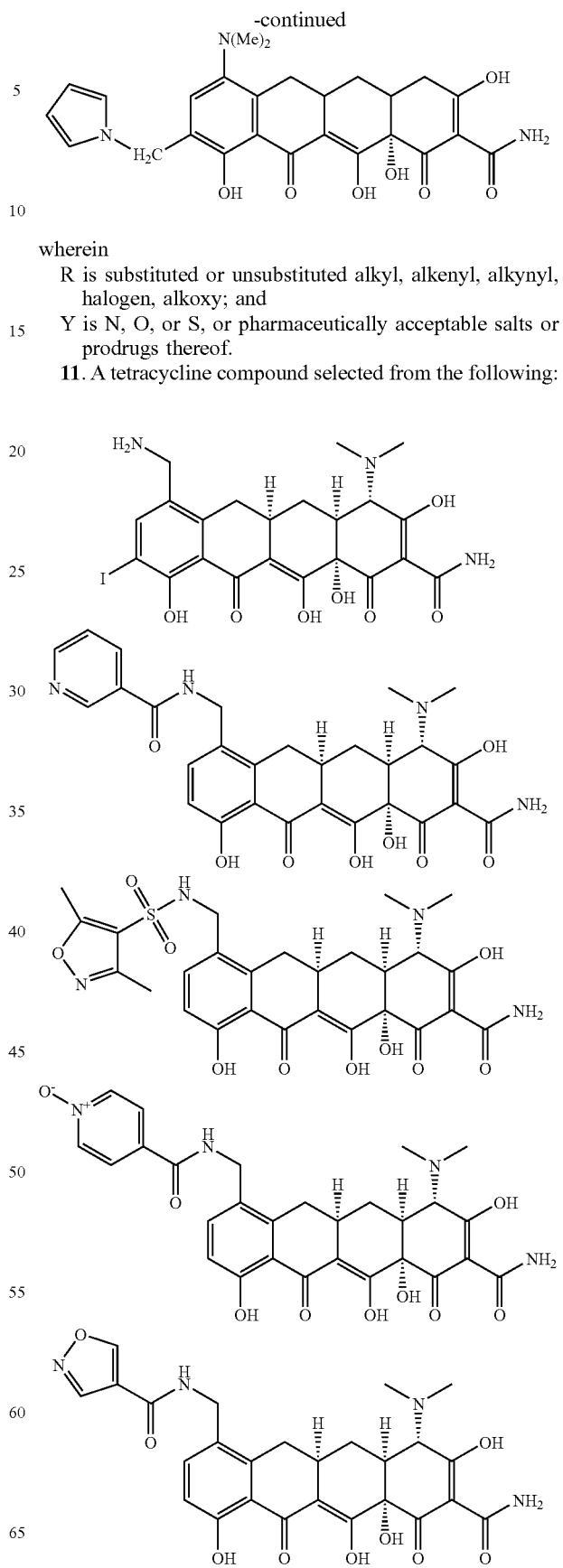
wherein
R is substituted or unsubstituted alkyl, alkenyl, alkynyl, halogen, alkoxy; and
Y is N, O, or S, or pharmaceutically acceptable salts or prodrugs thereof.
11. A tetracycline compound selected from the following:

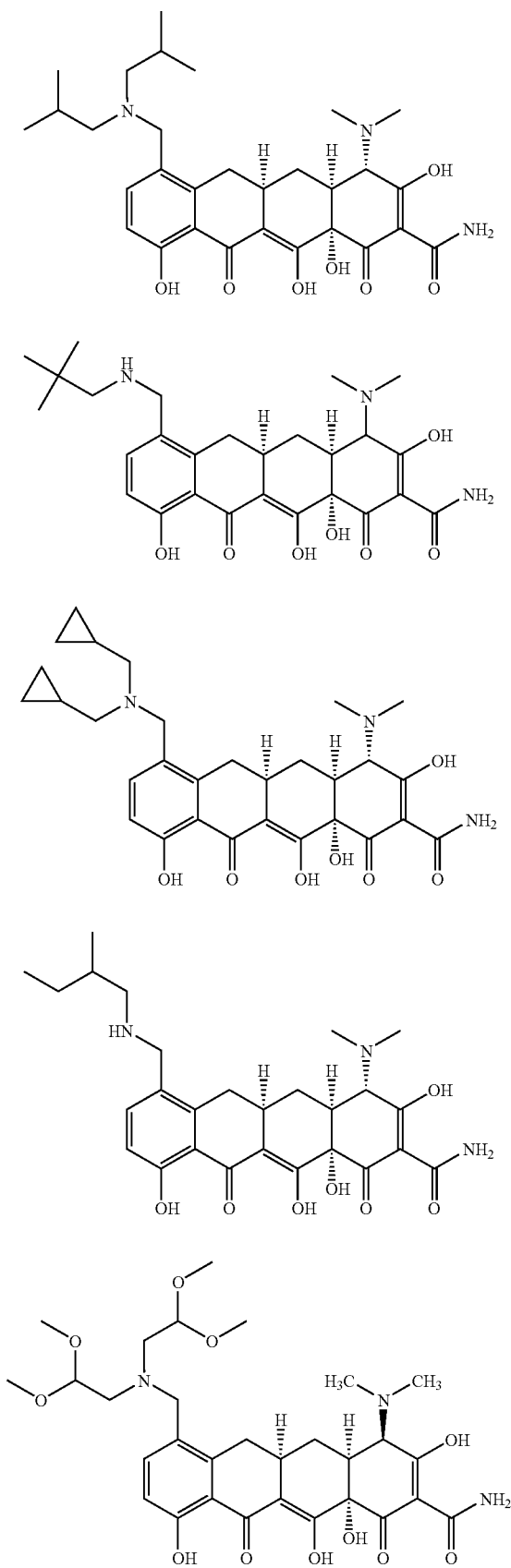
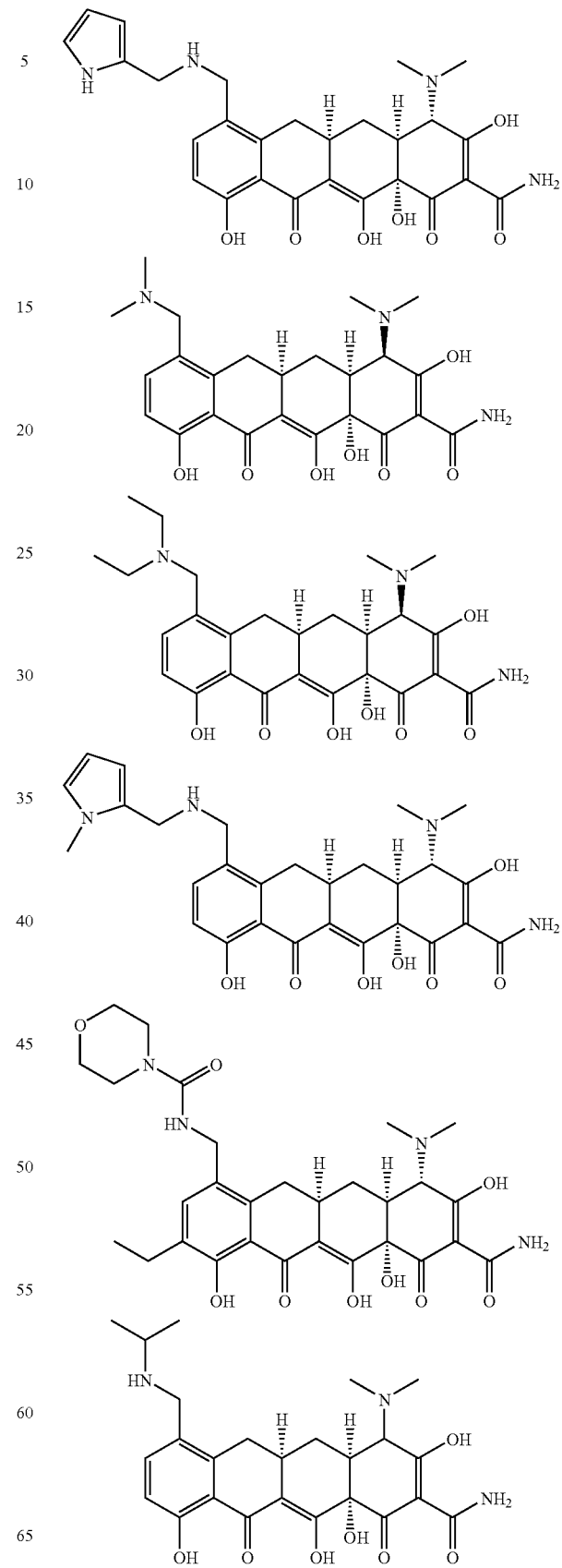

-continued
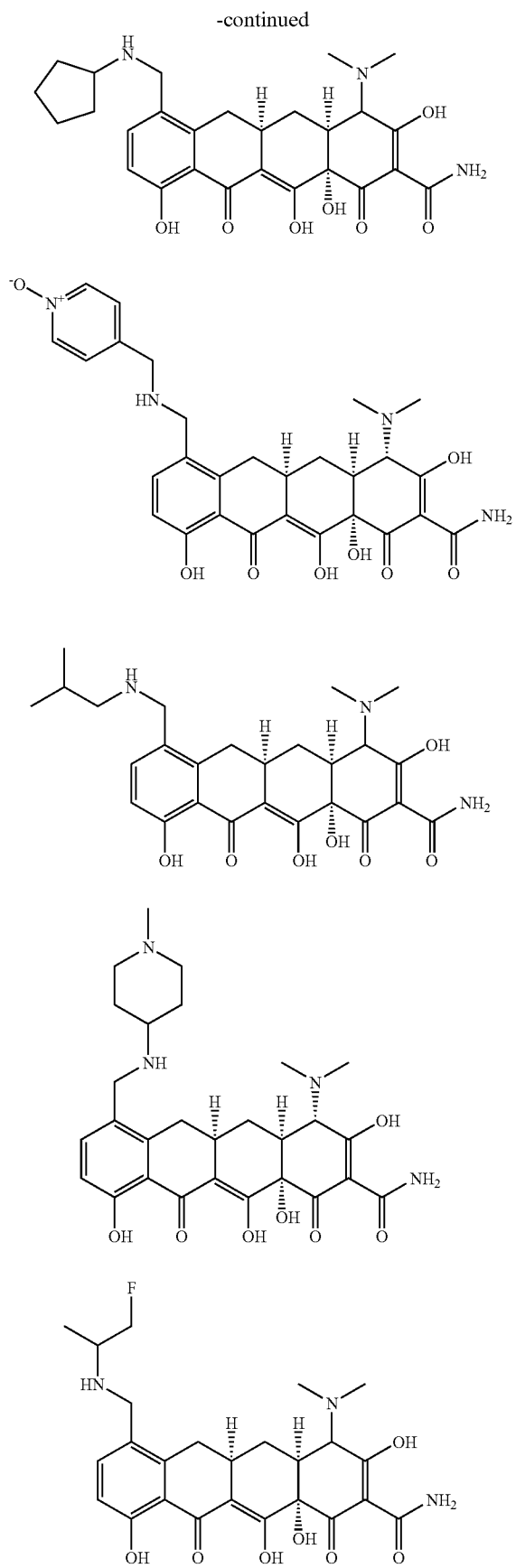
-continued
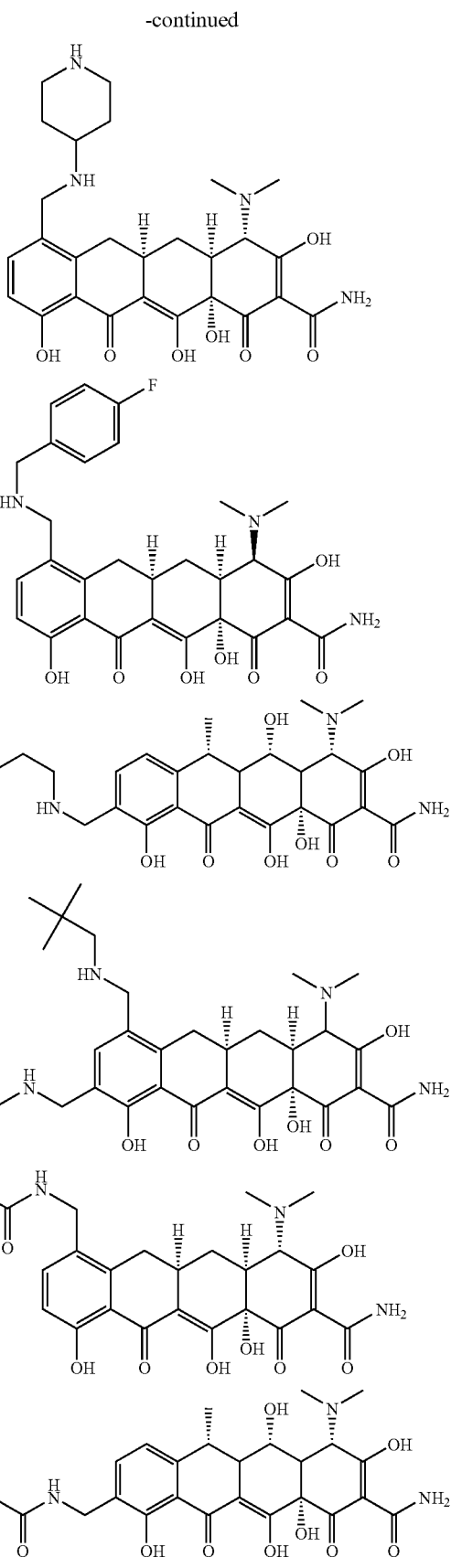

121    122
-continued
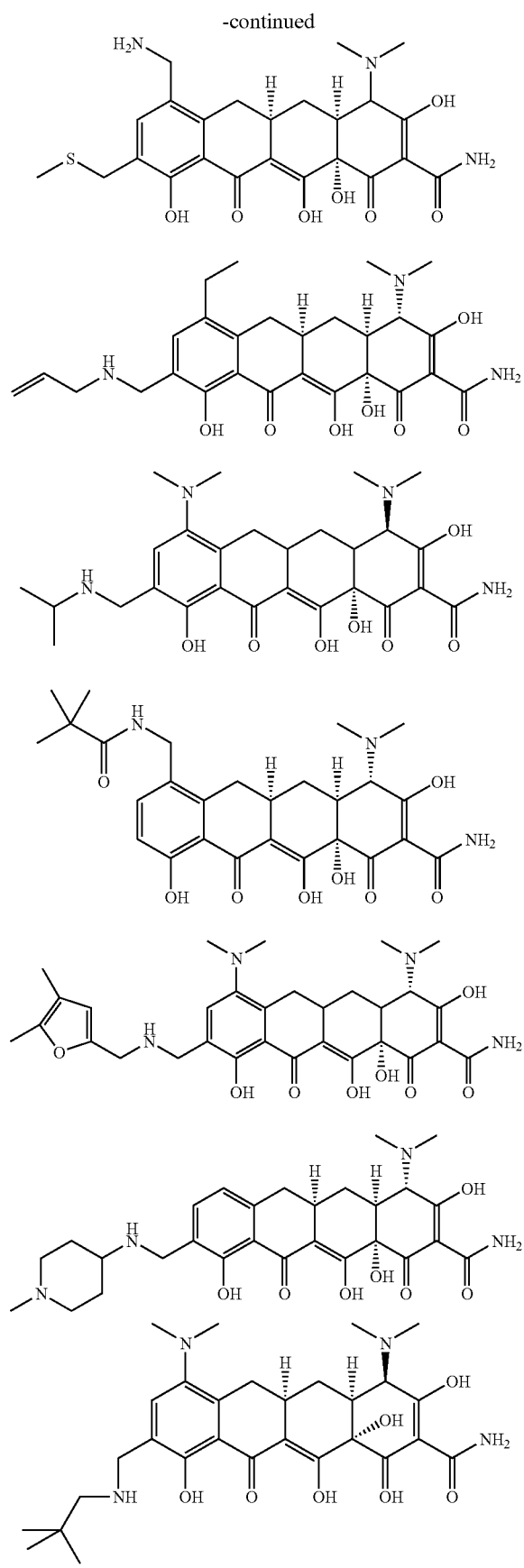
-continued
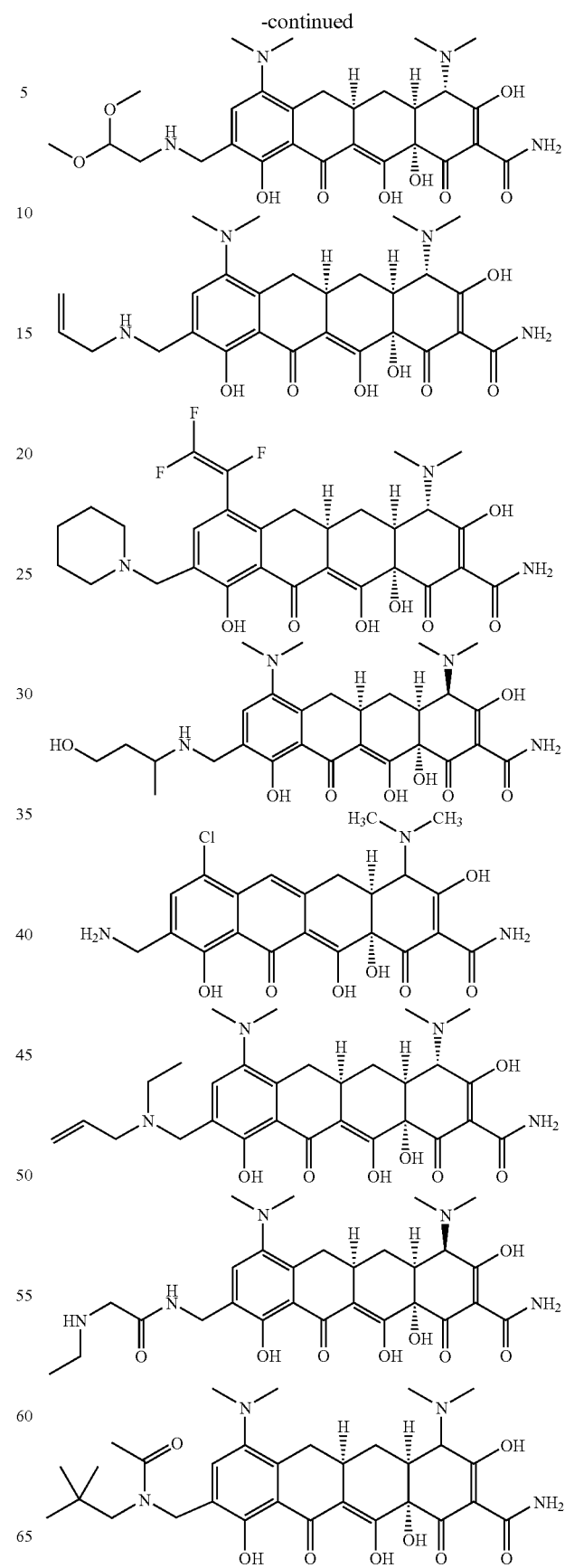

123
-continued
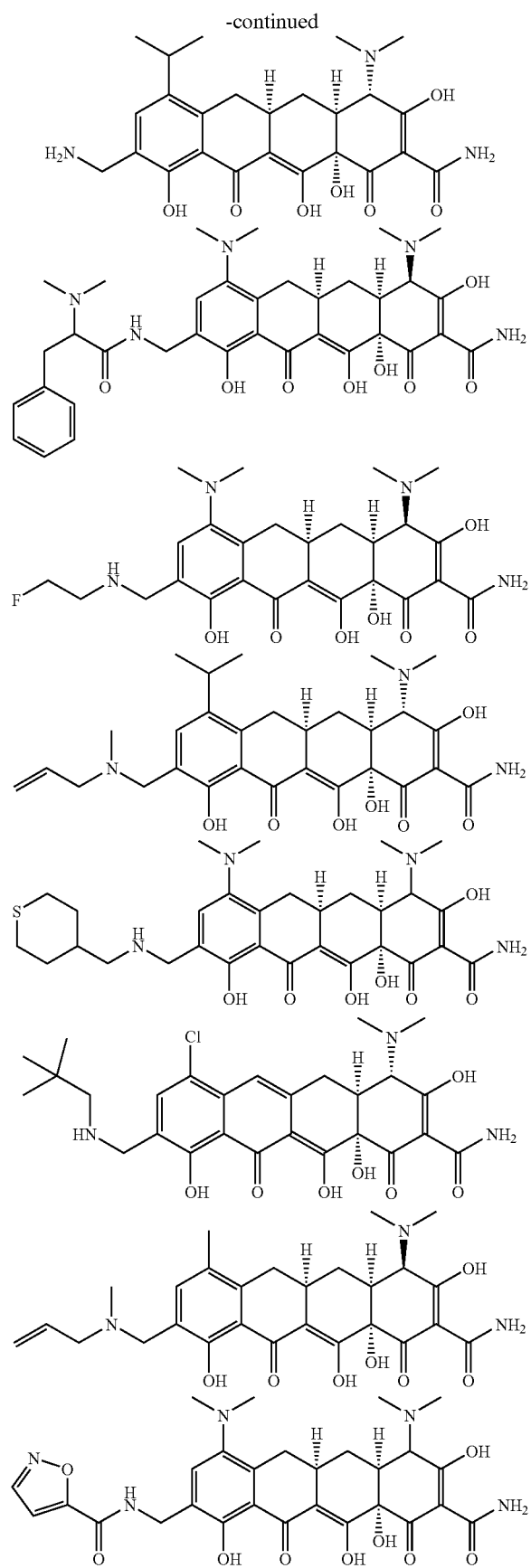
124
-continued
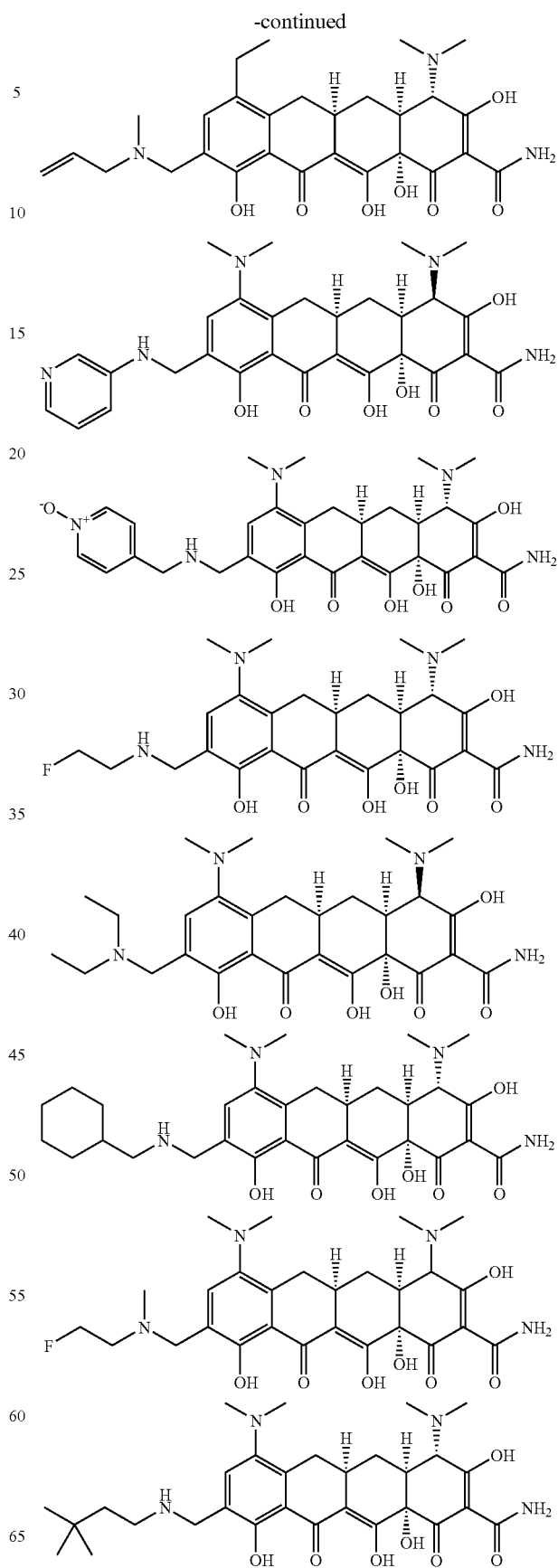

125
-continued
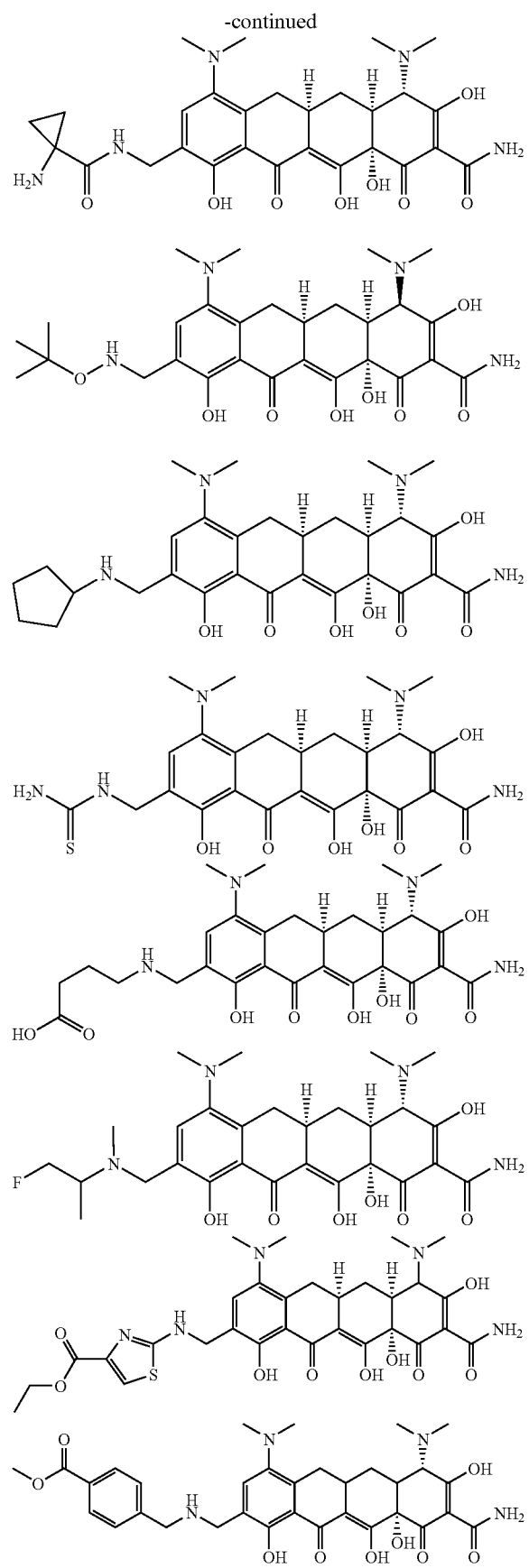
126
-continued
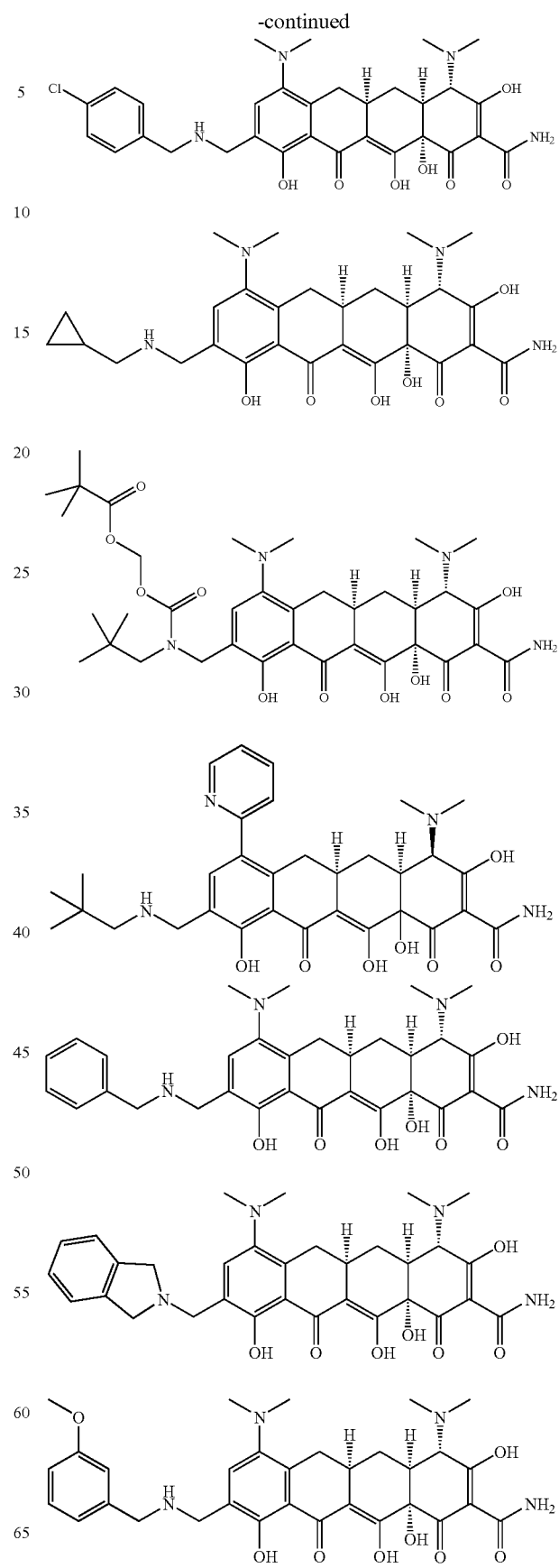

127
-continued
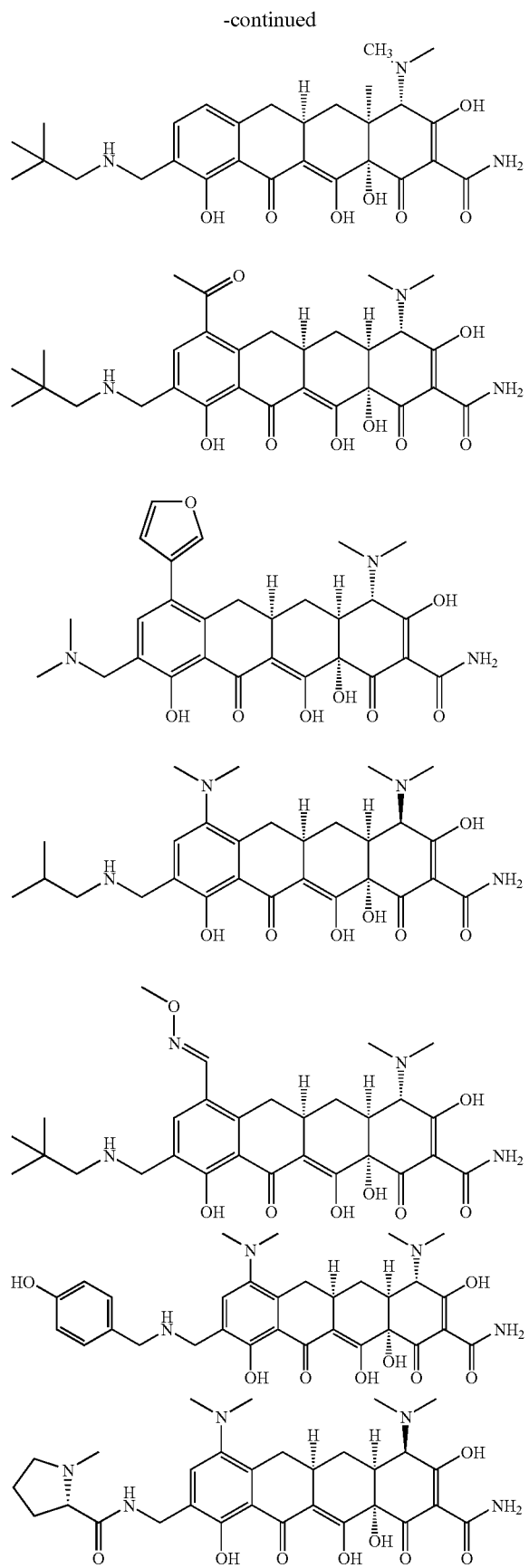
128
-continued
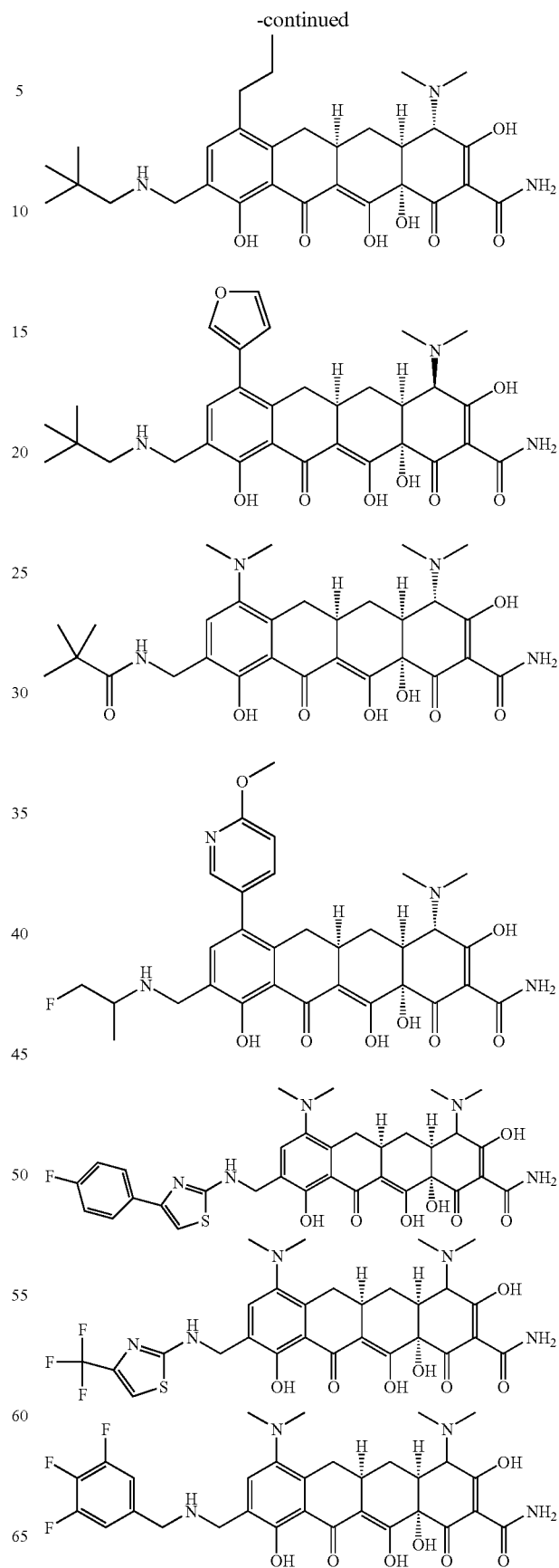

-continued

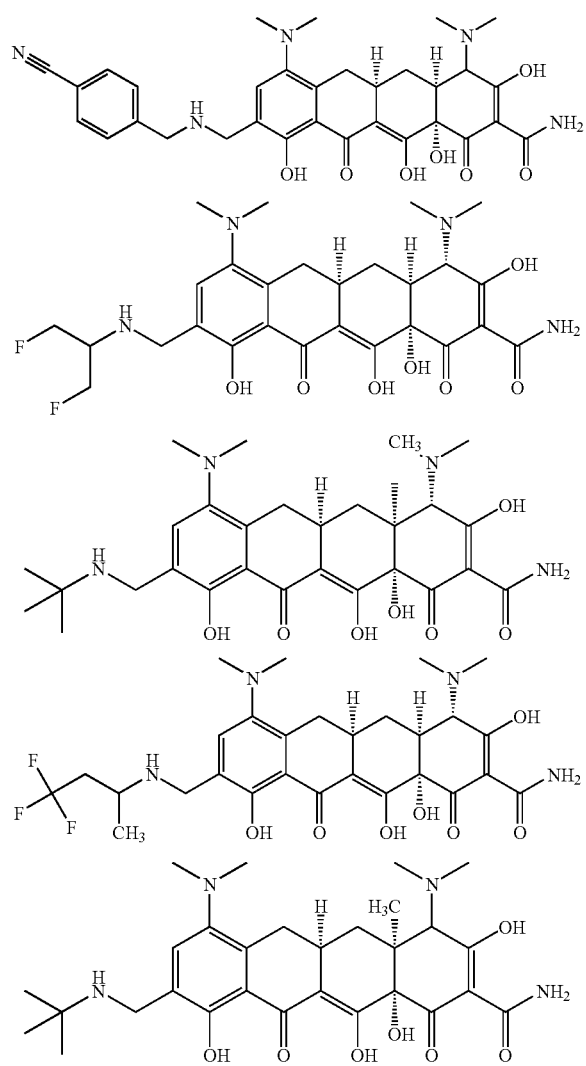

or a pharmaceutically acceptable salt thereof.

12. The compound of claim 1, wherein $R^7$ is dimethylamino.

13. The compound of claim 1 or 9, wherein $J^6$ is alkyl.

14. The compound of claim 13, wherein said compound is

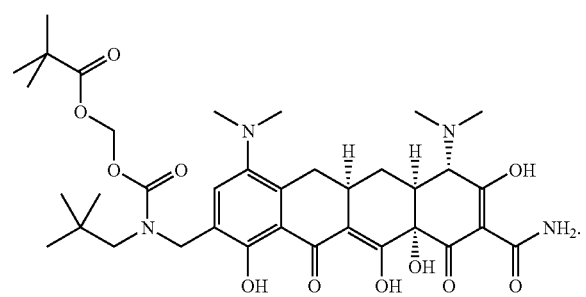

and pharmaceutically acceptable salts thereof.

15. The compound of claim 1, wherein said compound is

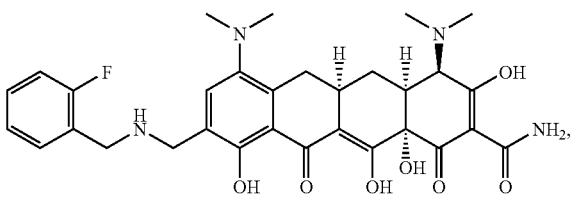

and pharmaceutically acceptable salts thereof.

16. The compound of claim 1, wherein said compound is

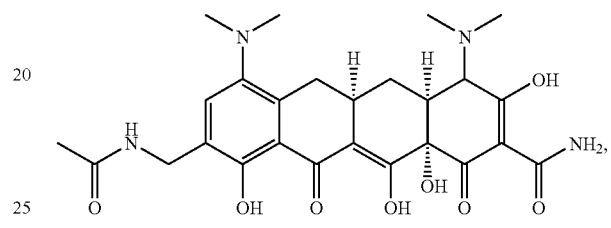

and pharmaceutically acceptable salts thereof.

17. The compound of claim 1, wherein said compound is

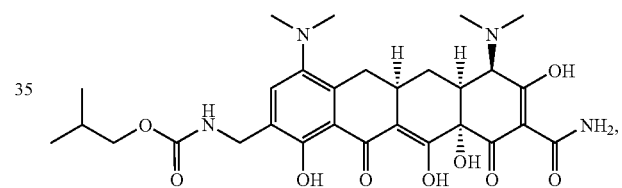

and pharmaceutically acceptable salts thereof.

18. The compound of claim 1, wherein said compound is

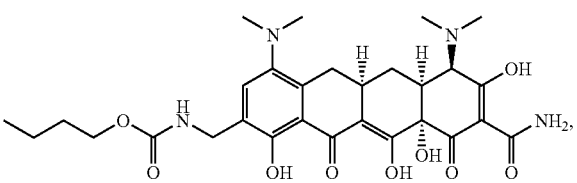

and pharmaceutically acceptable salts thereof.

19. The compound of claim 1, wherein said compound is

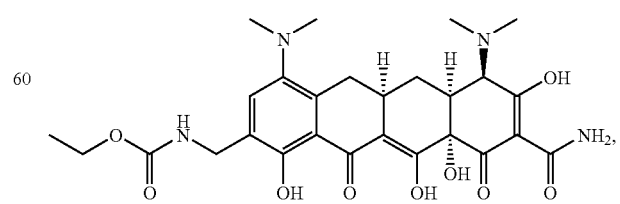

and pharmaceutically acceptable salts thereof.

20. The compound of claim 1, wherein said compound is

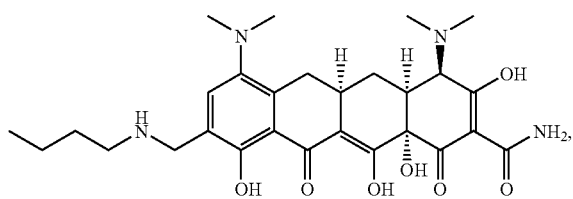

and pharmaceutically acceptable salts thereof.

21. The compound of claim 1, wherein said compound is

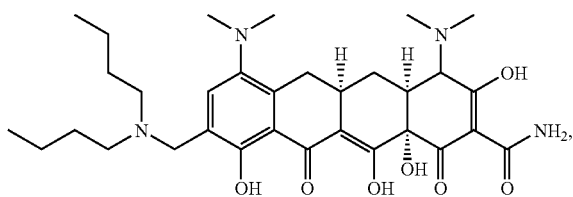

and pharmaceutically acceptable salts thereof.

22. The compound of claim 1, wherein said compound is

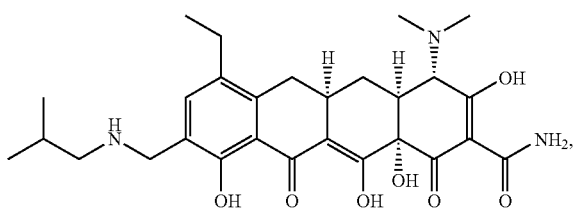

and pharmaceutically acceptable salts thereof.

23. The compound of claim 1, wherein said compound is

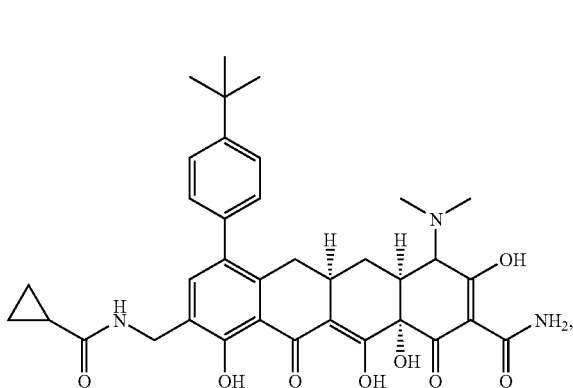

and pharmaceutically acceptable salts thereof.

24. The compound of claim 1, wherein said compound is

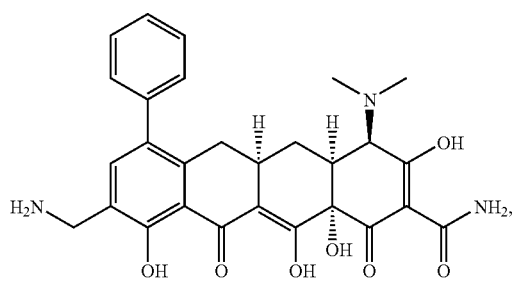

and pharmaceutically acceptable salts thereof.

25. The compound of claim 1, wherein said compound is

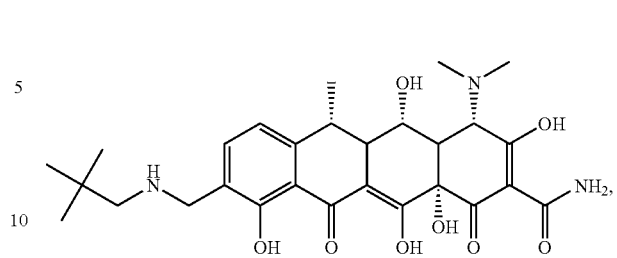

and pharmaceutically acceptable salts thereof.

26. The compound of claim 1, wherein said compound is

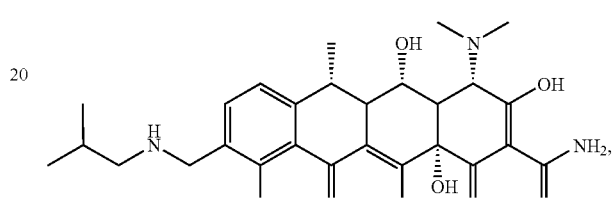

and pharmaceutically acceptable salts thereof.

27. The compound of claim 1, wherein said compound is

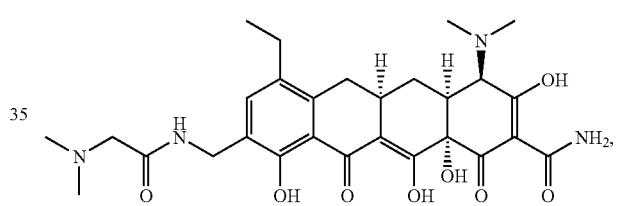

and pharmaceutically acceptable salts thereof.

28. The compound of claim 1, wherein said compound is

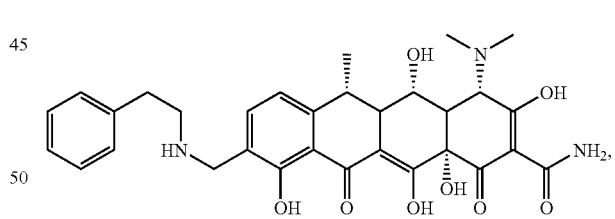

and pharmaceutically acceptable salts thereof.

29. The compound of claim 1, wherein said compound is

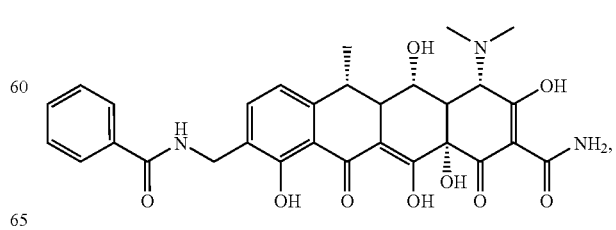

and pharmaceutically acceptable salts thereof.

30. The compound of claim 1, wherein said compound is

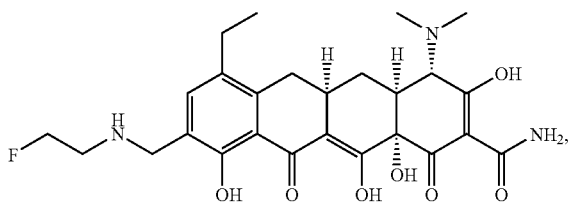

and pharmaceutically acceptable salts thereof.

31. The compound of claim 1, wherein said compound is

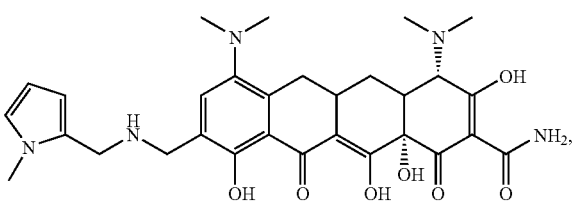

and pharmaceutically acceptable salts thereof.

32. The compound of claim 1, wherein said compound is

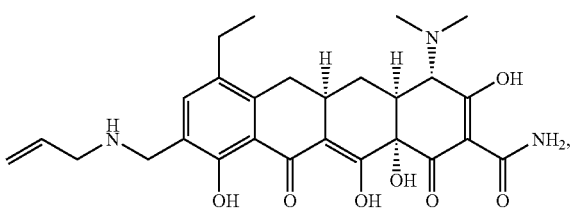

and pharmaceutically acceptable salts thereof.

33. The compound of claim 1, wherein said compound is

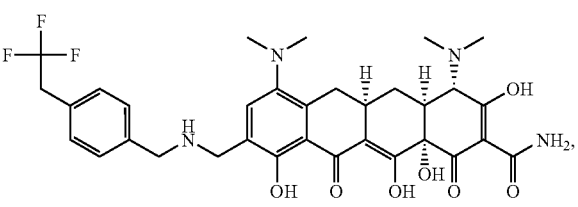

and pharmaceutically acceptable salts thereof.

34. The compound of claim 1, wherein said compound is

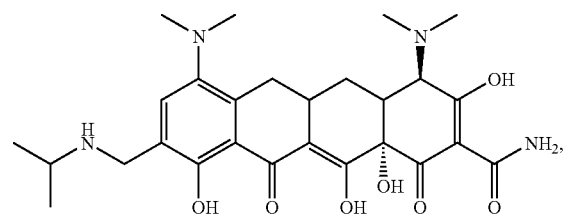

and pharmaceutically acceptable salts thereof.

35. The compound of claim 1, wherein said compound is

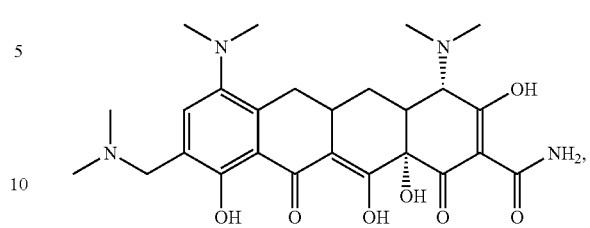

and pharmaceutically acceptable salts thereof.

36. The compound of claim 1, wherein said compound is

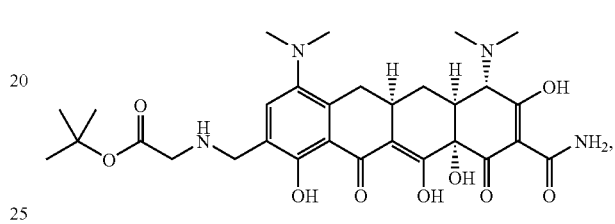

and pharmaceutically acceptable salts thereof.

37. The compound of claim 1, wherein said compound is

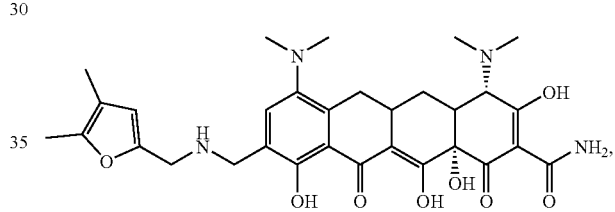

and pharmaceutically acceptable salts thereof.

38. The compound of claim 1, wherein said compound is

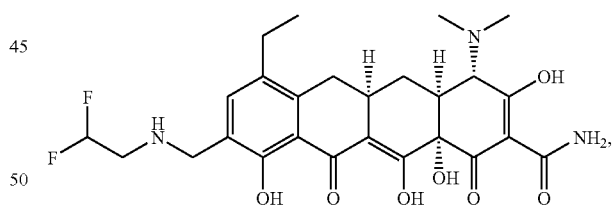

and pharmaceutically acceptable salts thereof.

39. The compound of claim 1, wherein said compound is

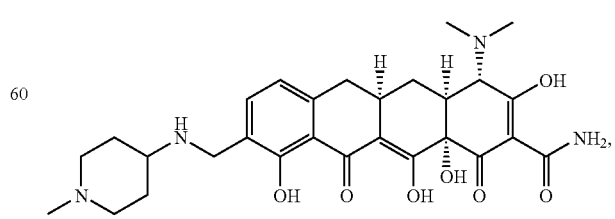

and pharmaceutically acceptable salts thereof.

40. The compound of claim 1, wherein said compound is

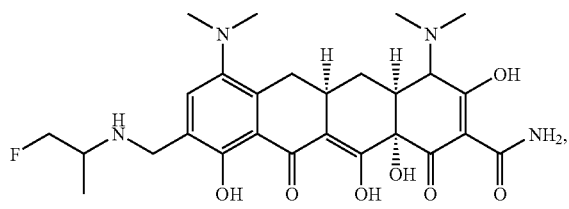

and pharmaceutically acceptable salts thereof.

41. The compound of claim 1, wherein said compound is

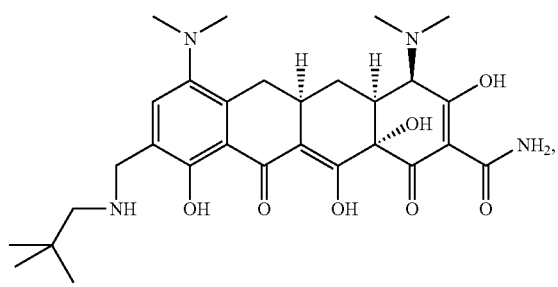

and pharmaceutically acceptable salts thereof.

42. The compound of claim 1, wherein said compound is

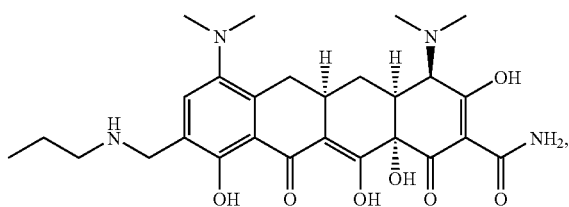

and pharmaceutically acceptable salts thereof.

43. The compound of claim 1, wherein said compound is

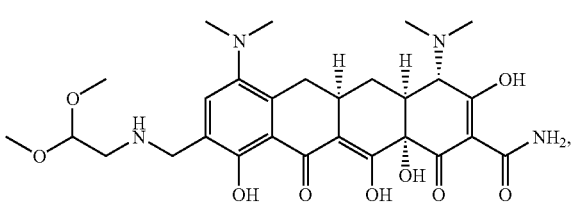

and pharmaceutically acceptable salts thereof.

44. The compound of claim 1, wherein said compound is

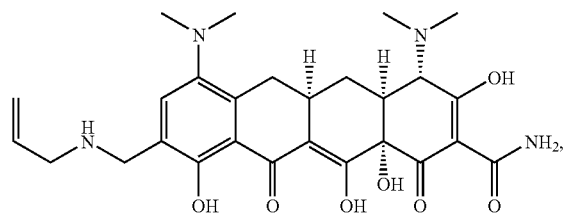

and pharmaceutically acceptable salts thereof.

45. The compound of claim 1, wherein said compound is

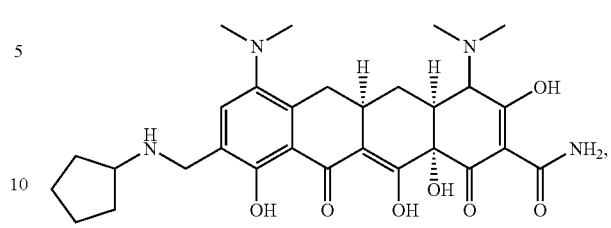

and pharmaceutically acceptable salts thereof.

46. The compound of claim 1, wherein said compound is

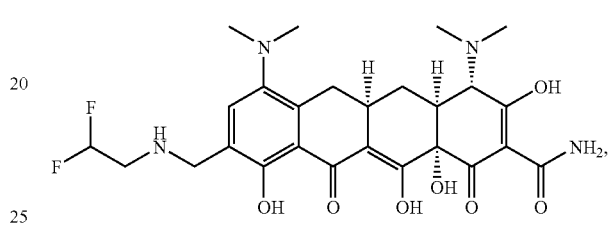

and pharmaceutically acceptable salts thereof.

47. The compound of claim 1, wherein said compound is

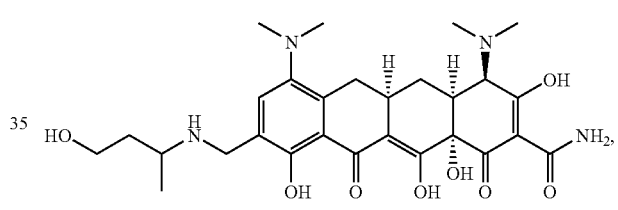

and pharmaceutically acceptable salts thereof.

48. The compound of claim 1, wherein said compound is

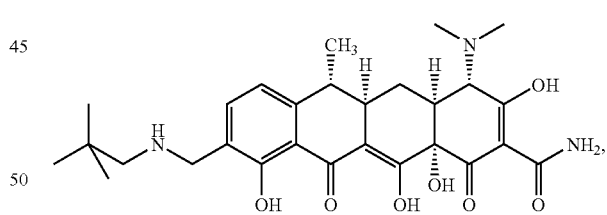

and pharmaceutically acceptable salts thereof.

49. The compound of claim 1, wherein said compound is

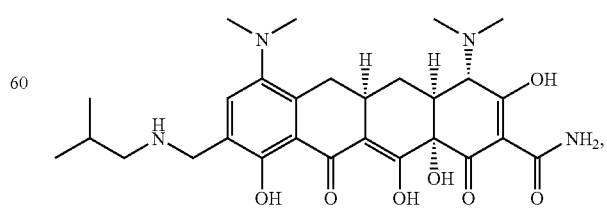

and pharmaceutically acceptable salts thereof.

50. The compound of claim 1, wherein said compound is

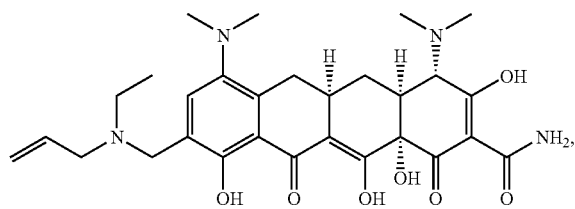

and pharmaceutically acceptable salts thereof.

51. The compound of claim 1, wherein said compound is

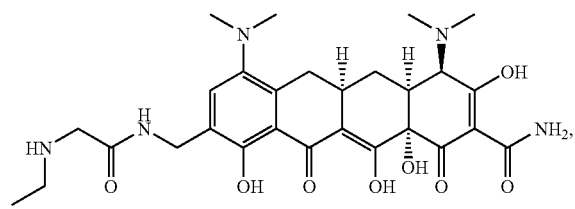

and pharmaceutically acceptable salts thereof.

52. The compound of claim 1, wherein said compound is

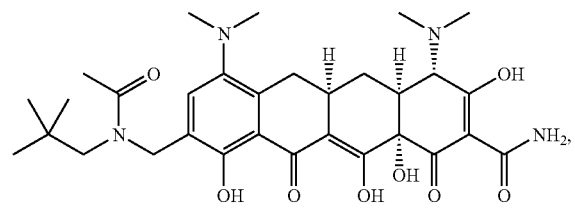

and pharmaceutically acceptable salts thereof.

53. The compound of claim 1, wherein said compound is

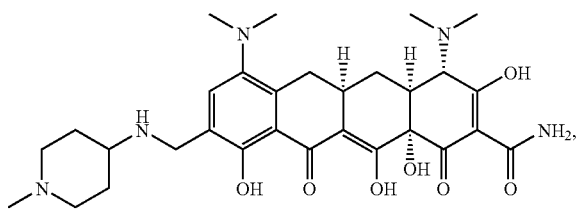

and pharmaceutically acceptable salts thereof.

54. The compound of claim 1, wherein said compound is

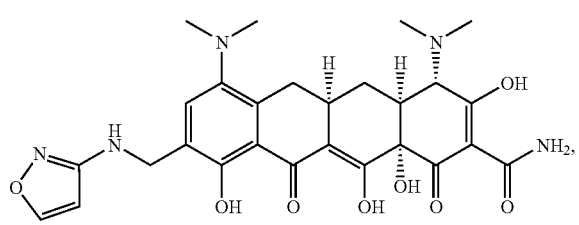

and pharmaceutically acceptable salts thereof.

55. The compound of claim 1, wherein said compound is

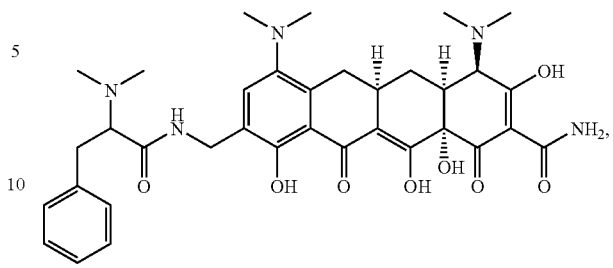

and pharmaceutically acceptable salts thereof.

56. The compound of claim 1, wherein said compound is

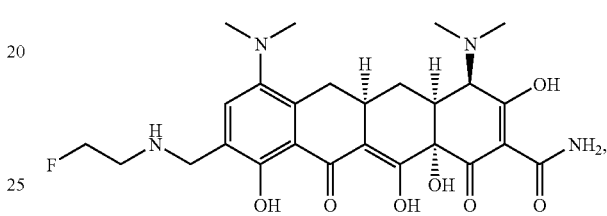

and pharmaceutically acceptable salts thereof.

57. The compound of claim 1, wherein said compound is

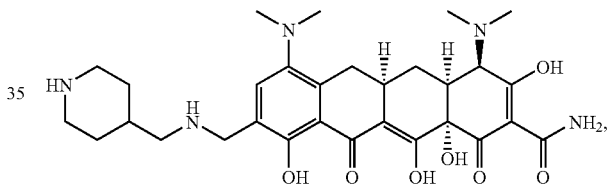

and pharmaceutically acceptable salts thereof.

58. The compound of claim 1, wherein said compound is

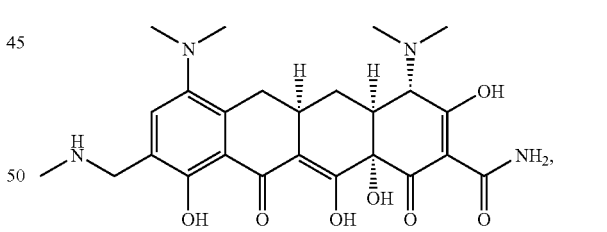

and pharmaceutically acceptable salts thereof.

59. The compound of claim 1, wherein said compound is

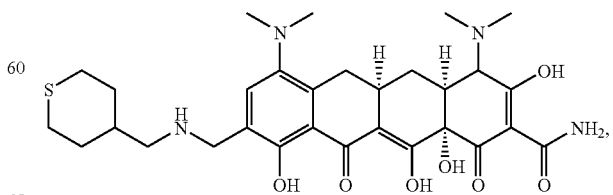

and pharmaceutically acceptable salts thereof.

60. The compound of claim 1, wherein said compound is

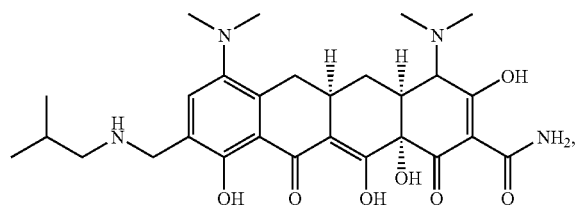

and pharmaceutically acceptable salts thereof.

61. The compound of claim 1, wherein said compound is

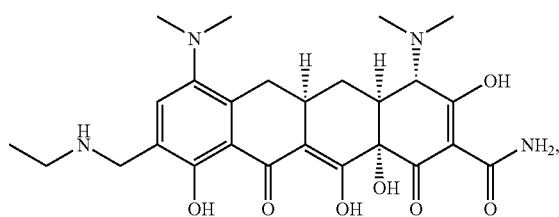

and pharmaceutically acceptable salts thereof.

62. The compound of claim 1, wherein said compound is

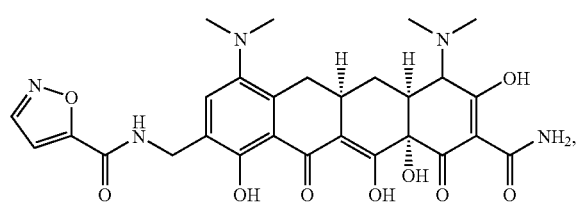

and pharmaceutically acceptable salts thereof.

63. The compound of claim 1, wherein said compound is

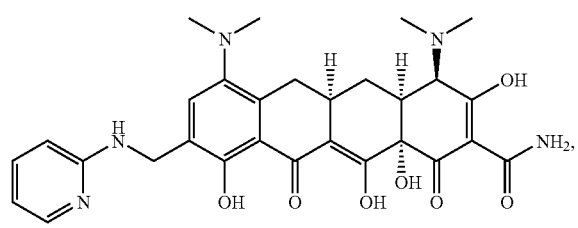

and pharmaceutically acceptable salts thereof.

64. The compound of claim 1, wherein said compound is

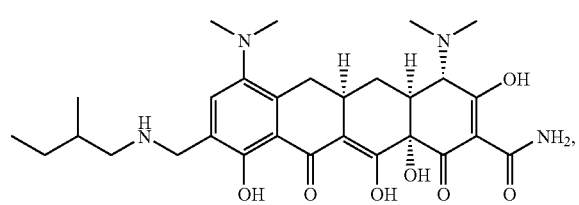

and pharmaceutically acceptable salts thereof.

65. The compound of claim 1, wherein said compound is

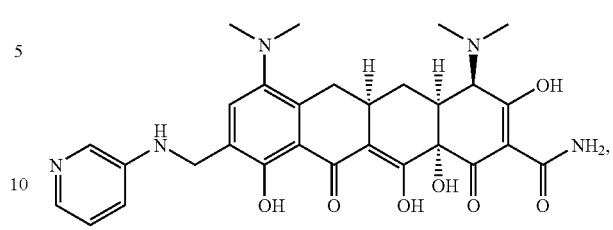

and pharmaceutically acceptable salts thereof.

66. The compound of claim 1, wherein said compound is

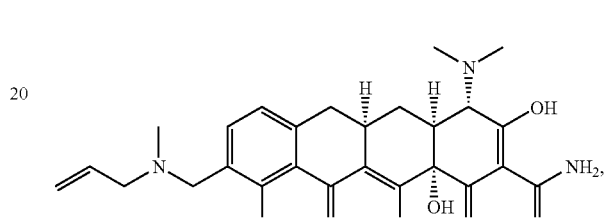

and pharmaceutically acceptable salts thereof.

67. The compound of claim 1, wherein said compound is

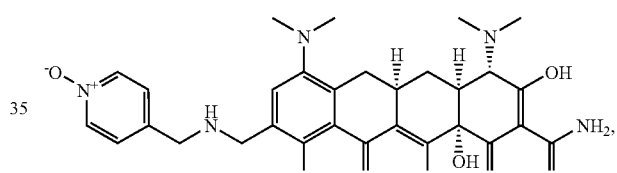

and pharmaceutically acceptable salts thereof.

68. The compound of claim 1, wherein said compound is

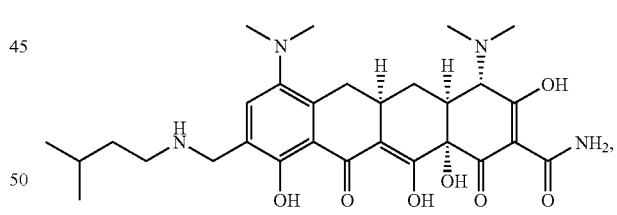

and pharmaceutically acceptable salts thereof.

69. The compound of claim 1, wherein said compound is

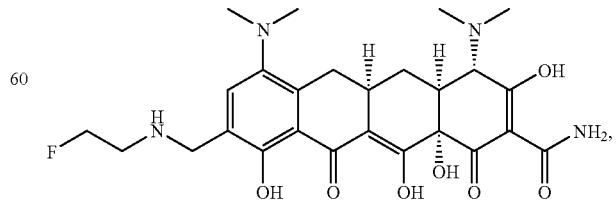

and pharmaceutically acceptable salts thereof.

70. The compound of claim 1, wherein said compound is

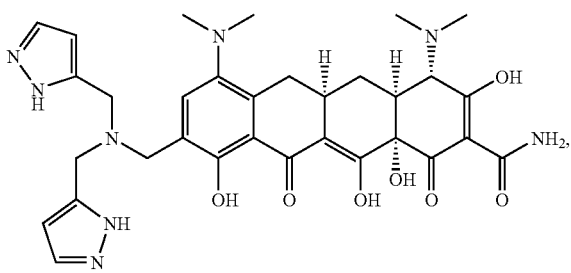

and pharmaceutically acceptable salts thereof.

71. The compound of claim 1, wherein said compound is

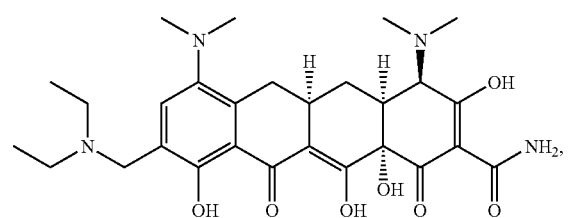

and pharmaceutically acceptable salts thereof.

72. The compound of claim 1, wherein said compound is

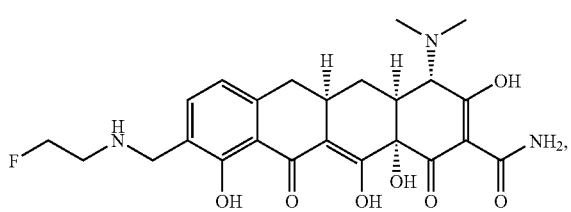

and pharmaceutically acceptable salts thereof.

73. The compound of claim 1, wherein said compound is

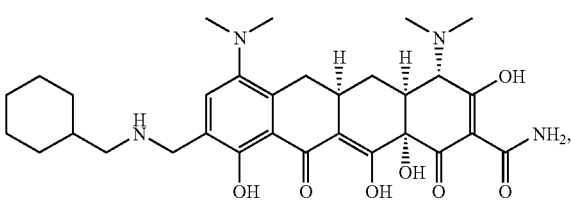

and pharmaceutically acceptable salts thereof.

74. The compound of claim 1, wherein said compound is

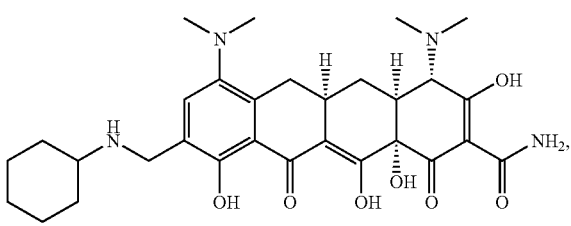

and pharmaceutically acceptable salts thereof.

75. The compound of claim 1, wherein said compound is

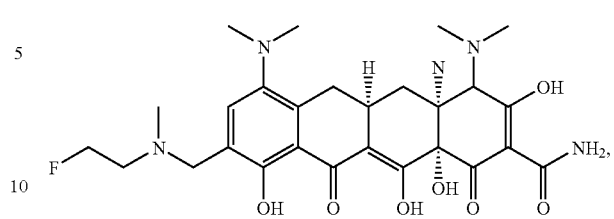

and pharmaceutically acceptable salts thereof.

76. The compound of claim 1, wherein said compound is

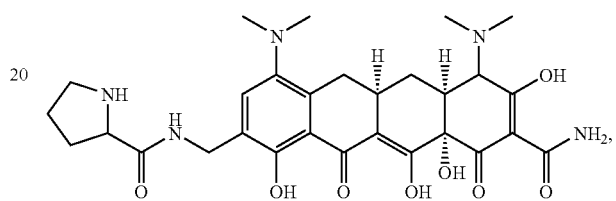

and pharmaceutically acceptable salts thereof.

77. The compound of claim 1, wherein said compound is

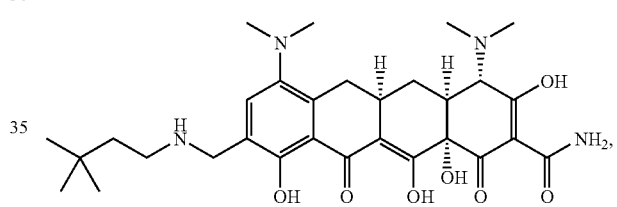

and pharmaceutically acceptable salts thereof.

78. The compound of claim 1, wherein said compound is

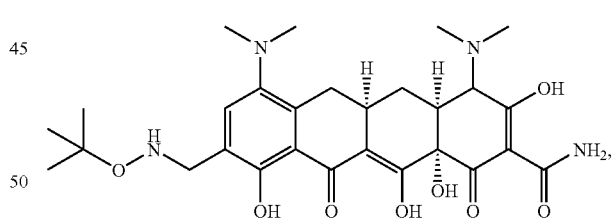

and pharmaceutically acceptable salts thereof.

79. The compound of claim 1, wherein said compound is

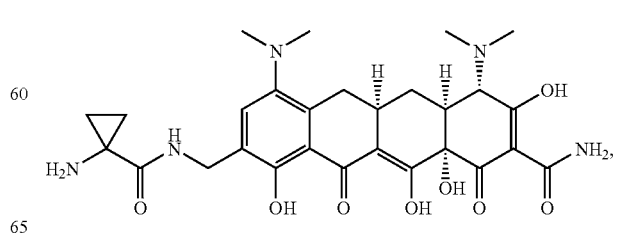

and pharmaceutically acceptable salts thereof.

80. The compound of claim 1, wherein said compound is

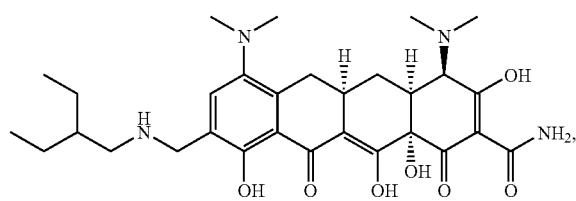

and pharmaceutically acceptable salts thereof.

81. The compound of claim 1, wherein said compound is

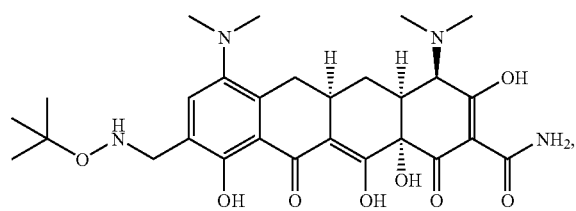

and pharmaceutically acceptable salts thereof.

82. The compound of claim 1, wherein said compound is

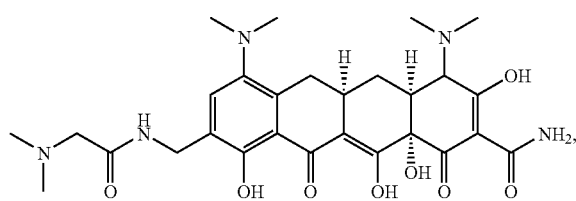

and pharmaceutically acceptable salts thereof.

83. The compound of claim 1, wherein said compound is

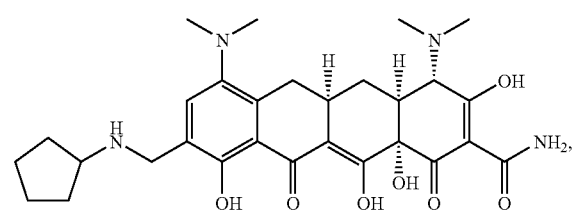

and pharmaceutically acceptable salts thereof.

84. The compound of claim 1, wherein said compound is

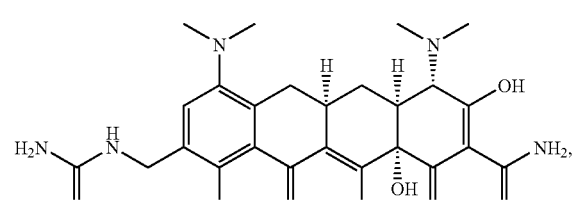

and pharmaceutically acceptable salts thereof.

85. The compound of claim 1, wherein said compound is

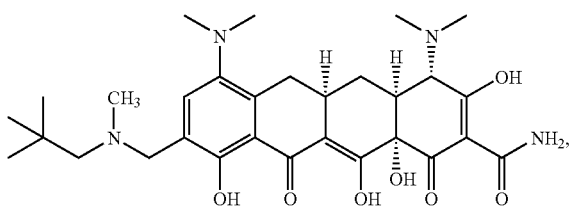

and pharmaceutically acceptable salts thereof.

86. The compound of claim 1, wherein said compound is

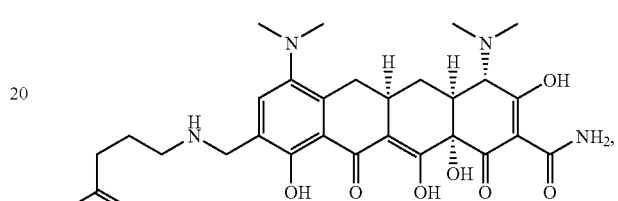

and pharmaceutically acceptable salts thereof.

87. The compound of claim 1, wherein said compound is

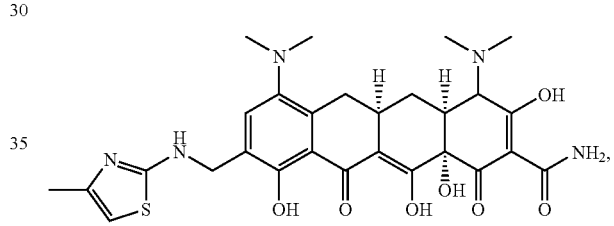

and pharmaceutically acceptable salts thereof.

88. The compound of claim 1, wherein said compound is

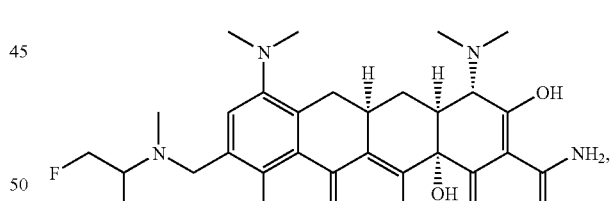

and pharmaceutically acceptable salts thereof.

89. The compound of claim 1, wherein said compound is

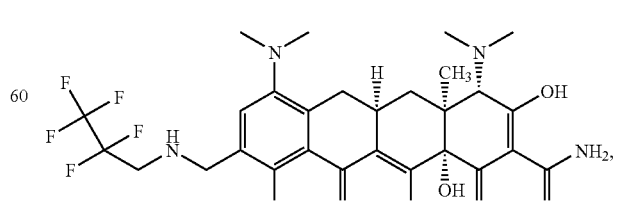

and pharmaceutically acceptable salts thereof.

90. The compound of claim 1, wherein said compound is

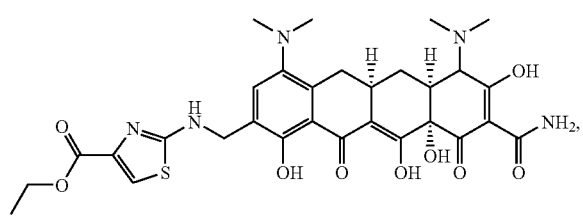

and pharmaceutically acceptable salts thereof.

91. The compound of claim 1, wherein said compound is

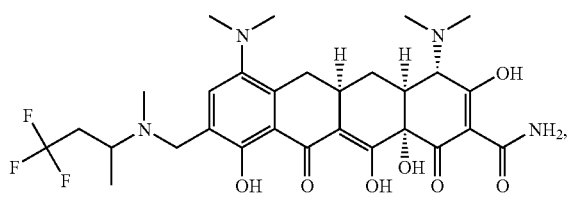

and pharmaceutically acceptable salts thereof.

92. The compound of claim 1, wherein said compound is

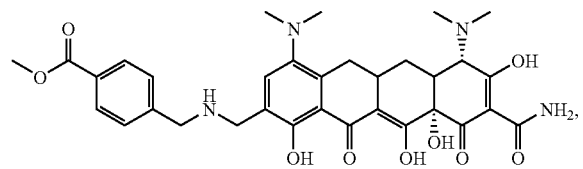

and pharmaceutically acceptable salts thereof.

93. The compound of claim 1, wherein said compound is

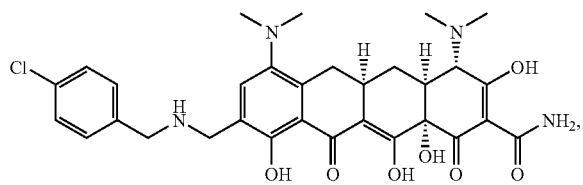

and pharmaceutically acceptable salts thereof.

94. The compound of claim 1, wherein said compound is

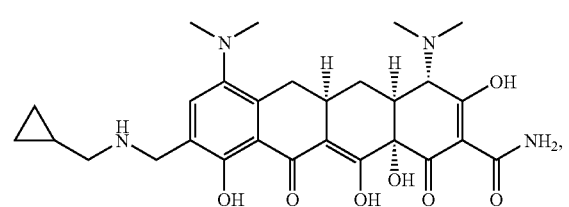

and pharmaceutically acceptable salts thereof.

95. The compound of claim 1, wherein said compound is

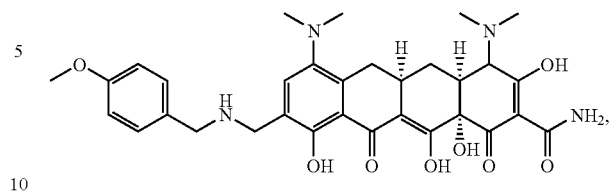

and pharmaceutically acceptable salts thereof.

96. The compound of claim 1, wherein said compound is

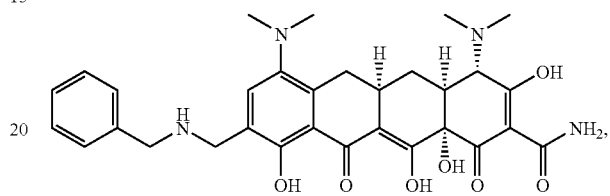

and pharmaceutically acceptable salts thereof.

97. The compound of claim 1, wherein said compound is

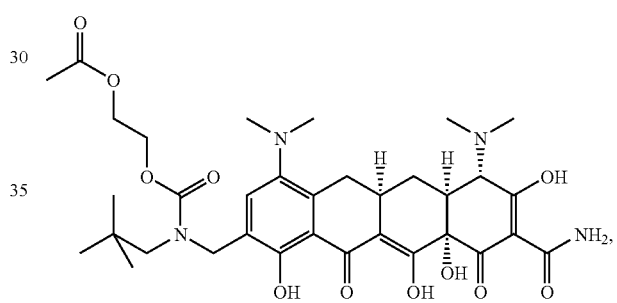

and pharmaceutically acceptable salts thereof.

98. The compound of claim 1, wherein said compound is

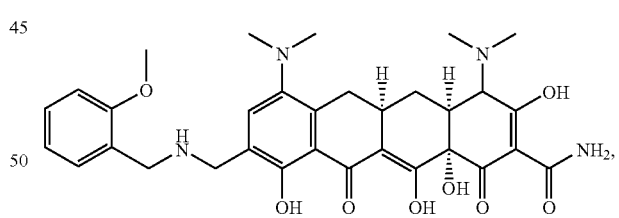

and pharmaceutically acceptable salts thereof.

99. The compound of claim 1, wherein said compound is

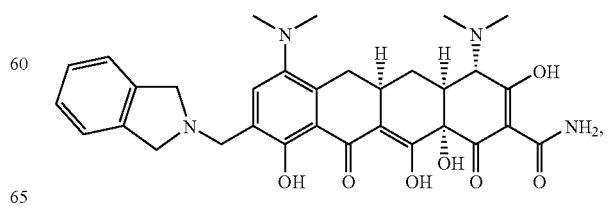

and pharmaceutically acceptable salts thereof.

100. The compound of claim 1, wherein said compound is

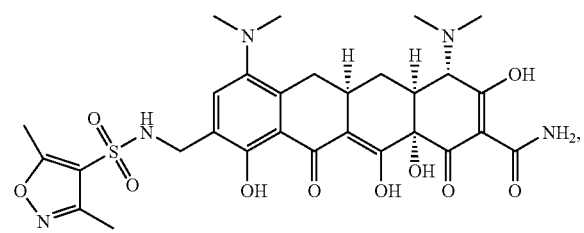

and pharmaceutically acceptable salts thereof.

101. The compound of claim 1, wherein said compound is

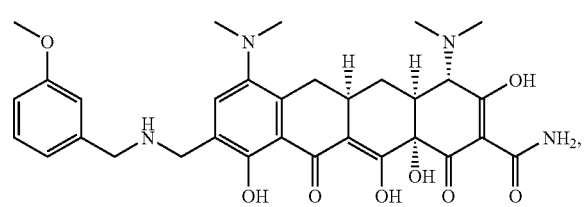

and pharmaceutically acceptable salts thereof.

102. The compound of claim 1, wherein said compound is

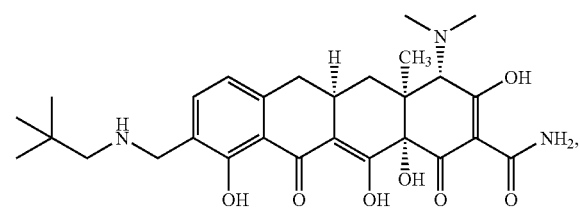

and pharmaceutically acceptable salts thereof.

103. The compound of claim 1, wherein said compound is

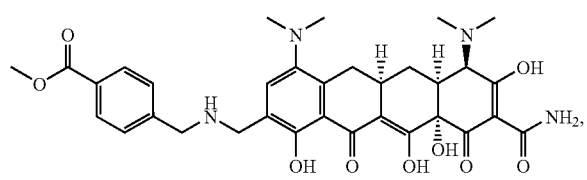

and pharmaceutically acceptable salts thereof.

104. The compound of claim 1, wherein said compound is

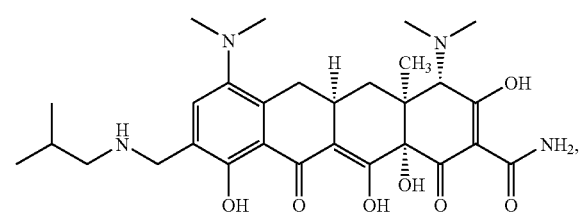

and pharmaceutically acceptable salts thereof.

105. The compound of claim 1, wherein said compound is

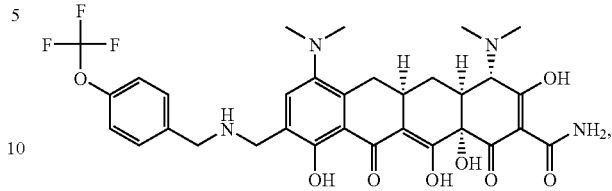

and pharmaceutically acceptable salts thereof.

106. The compound of claim 1, wherein said compound is

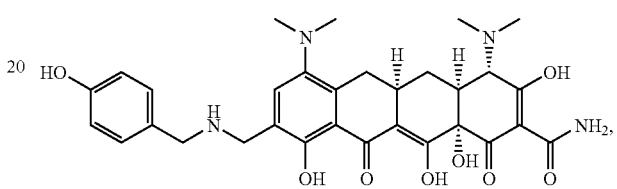

and pharmaceutically acceptable salts thereof.

107. The compound of claim 1, wherein said compound is

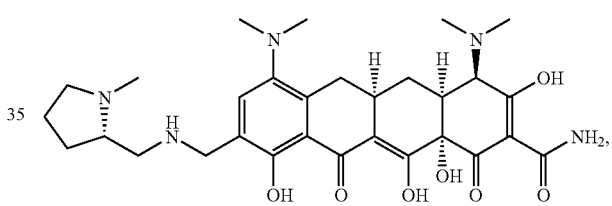

and pharmaceutically acceptable salts thereof.

108. The compound of claim 1, wherein said compound is

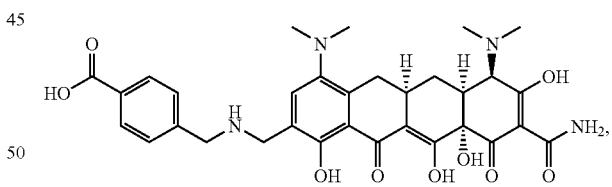

and pharmaceutically acceptable salts thereof.

109. The compound of claim 1, wherein said compound is

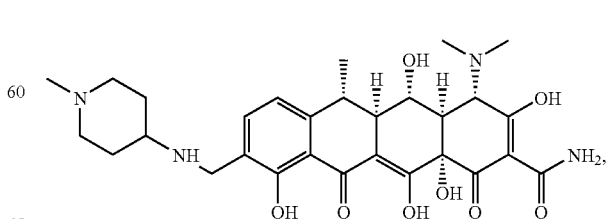

and pharmaceutically acceptable salts thereof.

110. The compound of claim 1, wherein said compound is

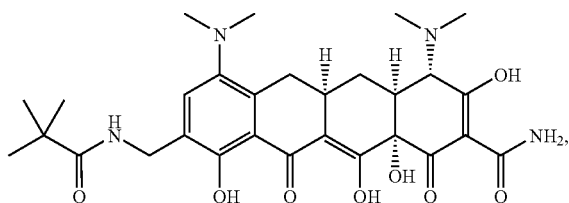

and pharmaceutically acceptable salts thereof.

111. The compound of claim 1, wherein said compound is

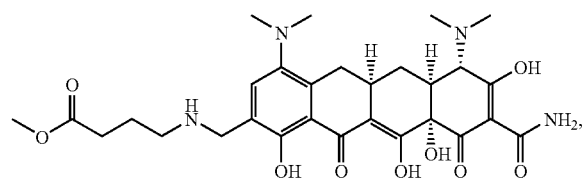

and pharmaceutically acceptable salts thereof.

112. The compound of claim 1, wherein said compound is

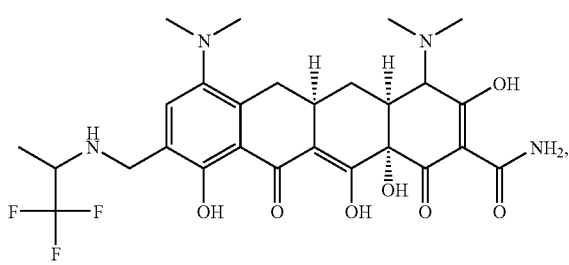

and pharmaceutically acceptable salts thereof.

113. The compound of claim 1, wherein said compound is

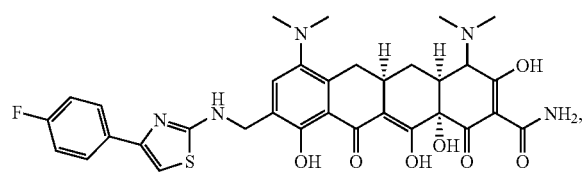

and pharmaceutically acceptable salts thereof.

114. The compound of claim 1, wherein said compound is

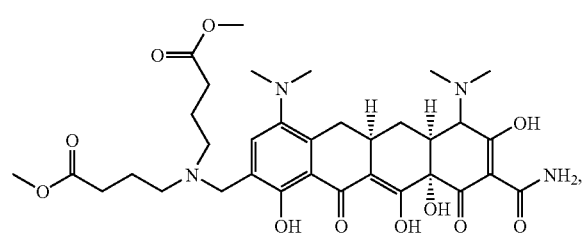

and pharmaceutically acceptable salts thereof.

115. The compound of claim 1, wherein said compound is

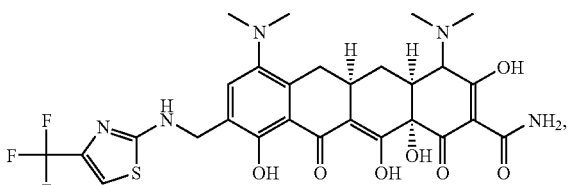

and pharmaceutically acceptable salts thereof.

116. The compound of claim 1, wherein said compound is

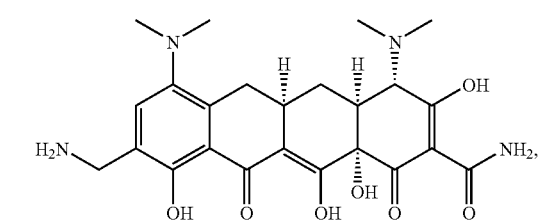

and pharmaceutically acceptable salts thereof.

117. The compound of claim 1, wherein said compound is

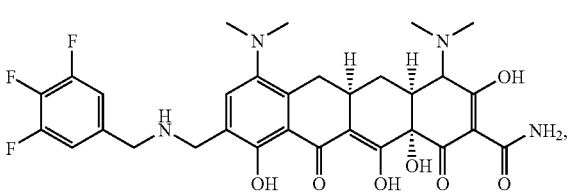

and pharmaceutically acceptable salts thereof.

118. The compound of claim 1, wherein said compound is

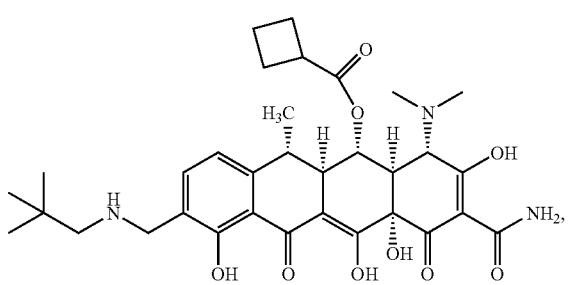

and pharmaceutically acceptable salts thereof.

119. The compound of claim 1, wherein said compound is

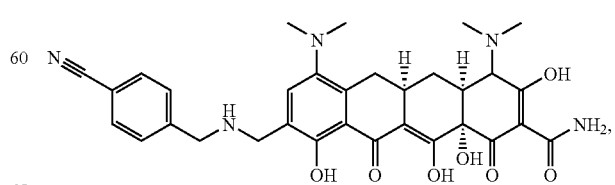

and pharmaceutically acceptable salts thereof.

120. The compound of claim 1, wherein said compound is

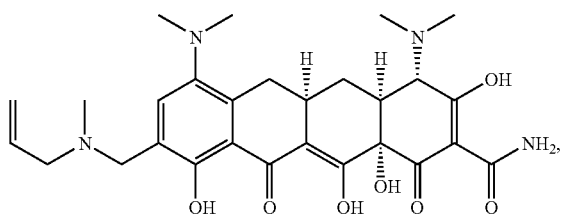

and pharmaceutically acceptable salts thereof.

121. The compound of claim 1, wherein said compound is

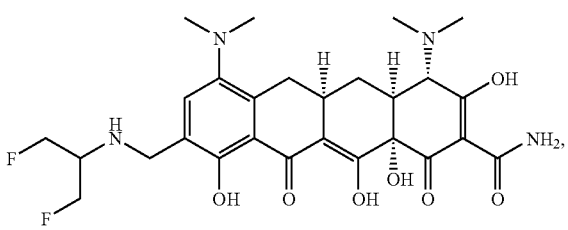

and pharmaceutically acceptable salts thereof.

122. The compound of claim 1, wherein said compound is

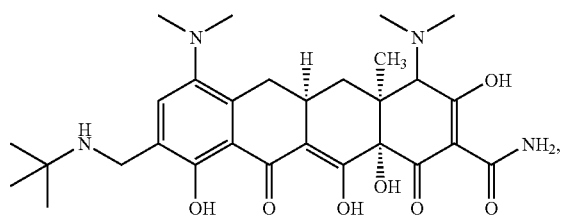

and pharmaceutically acceptable salts thereof.

123. The compound of claim 1, wherein said compound is

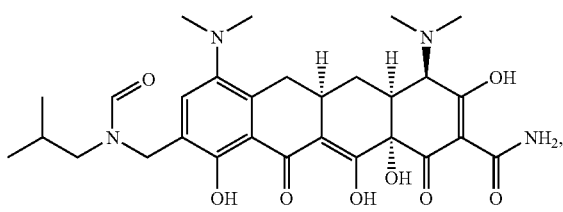

and pharmaceutically acceptable salts thereof.

124. The compound of claim 1, wherein said compound is

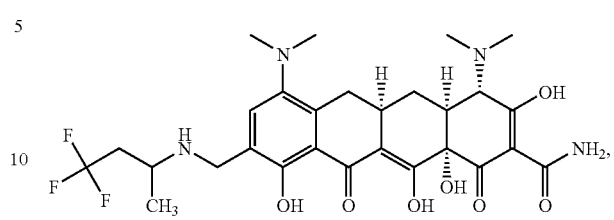

and pharmaceutically acceptable salts thereof.

125. The compound of claim 1, wherein said compound is

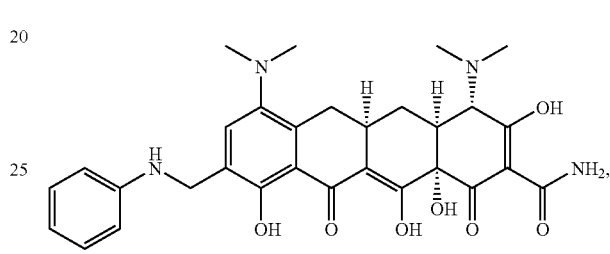

and pharmaceutically acceptable salts thereof.

126. The compound of claim 1, wherein said compound is

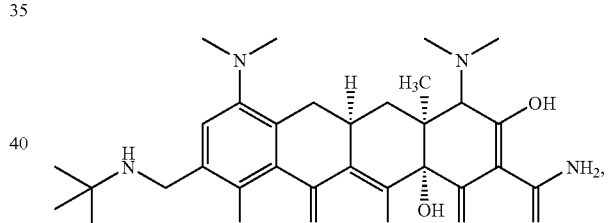

and pharmaceutically acceptable salts thereof.

127. A pharmaceutical composition comprising an effective amount of a tetracycline compound of any one of claims 1, 10 or 11, and a pharmaceutically acceptable carrier.

128. The pharmaceutical composition of claim 127, wherein said effective amount is effective to treat a tetracycline responsive state.

* * * * *

UNITED STATES PATENT AND TRADEMARK OFFICE
CERTIFICATE OF CORRECTION

PATENT NO. : 7,326,696 B2 Page 1 of 1
APPLICATION NO. : 10/737361
DATED : February 5, 2008
INVENTOR(S) : Mark L. Nelson et al.

It is certified that error appears in the above-identified patent and that said Letters Patent is hereby corrected as shown below:

In the Claims:

At Column 111, line 17, please delete:

"$R^{13}$ is hydrogen, hydroxyl, alkyl, alkenyl, alkynyl, alkoxy, alkylthio, alkylsulfinyl, alkylsulfonyl, alkylamino, or an arylalkyl;"

Signed and Sealed this

Fourteenth Day of October, 2008

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 7,326,696 B2 | Page 1 of 7 |
| APPLICATION NO. | : 10/737361 | |
| DATED | : February 5, 2008 | |
| INVENTOR(S) | : Mark L. Nelson et al. | |

It is certified that error appears in the above-identified patent and that said Letters Patent is hereby corrected as shown below:

At column 3, line 53, replace "X is $CHC(R_{13}Y'Y)$, $CR^{6'}R^6$, $C=CR^{6'}R^6$, S, $NP^6$, or O;" with --X is $CHC(R^{13}Y'Y)$, $CR^{6'}R^6$, $C=CR^{6'}R^6$, S, $NR^6$, or O;--.

At column 4, lines 18-22, replace "Y' and Y are each independently hydrogen, halogen, hydroxyl, cyano, sulihydryl, amino, alkyl, alkenyl, alkynyl, alkoxy, alkylthio, alkylsulfinyl, alkylsulfonyl, alkylamino, or an arylalkyl, and pharmaceutically acceptable salts thereof." with --Y' and Y are each independently hydrogen, halogen, hydroxyl, cyano, sulfhydryl, amino, alkyl, alkenyl, alkynyl, alkoxy, alkylthio, alkylsulfinyl, alkylsulfonyl, alkylamino, or an arylalkyl, and pharmaceutically acceptable salts thereof.--.

At column 11, lines 61-62, replace "R is substituted or unsubstituted alkyl, alkenyl, alkyyl, halogen, alkoxy; and" with --R is substituted or unsubstituted alkyl, alkenyl, alkynyl, halogen, alkoxy; and--.

At column 12, lines 53-57, replace "Y' and Y are each independently hydrogen, halogen, hydroxyl, cyano, sulihydryl, amino, alkyl, alkenyl, alkynyl, alkoxy, alkylthio, alkylsulfinyl, alkylsulfonyl, alkylamino, or an arylalkyl, and pharmaceutically acceptable salts thereof." with --Y' and Y are each independently hydrogen, halogen, hydroxyl, cyano, sulfhydryl, amino, alkyl, alkenyl, alkynyl, alkoxy, alkylthio, alkylsulfinyl, alkylsulfonyl, alkylamino, or an arylalkyl, and pharmaceutically acceptable salts thereof.--.

At column 12, lines 61-65, replace "In another embodiment, the aminoalkyl tetracycline compound is a demeclocycline compound (e.g., wherein $R^4$ is $NR^{4'}R^{4''}$, $R^{4'}$ and $R^{4''}$ are each methyl, $R^5$ is hydrogen, X is $CR^6R^{6'}$, $R^6$ is OH, $R^{6'}$ is hydrogen, and $R^7$ is chlorine)." with --In another embodiment, the aminoalkyl tetracycline compound is a demeclocycline compound (e.g., wherein $R^4$ is $NR^{4'}R^{4''}$, $R^{4'}$ and $R^{4''}$ are each methyl, $R^5$ is hydrogen, X is $CR^6R^{6'}$, $R^6$ is OH, $R^{6'}$ is hydrogen, and $R^7$ is chlorine).--.

Signed and Sealed this
Third Day of July, 2012

David J. Kappos
*Director of the United States Patent and Trademark Office*

CERTIFICATE OF CORRECTION (continued)
U.S. Pat. No. 7,326,696 B2

At column 14, lines 35-40, replace

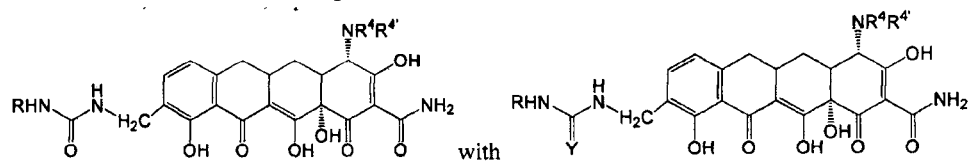 with

At column 14, lines 55-60, replace

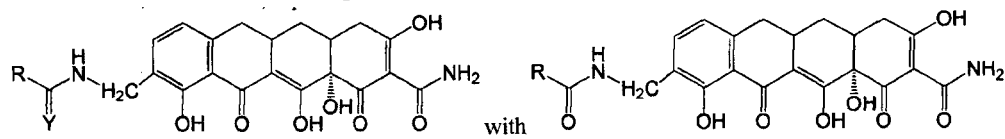 with

At column 19, replace

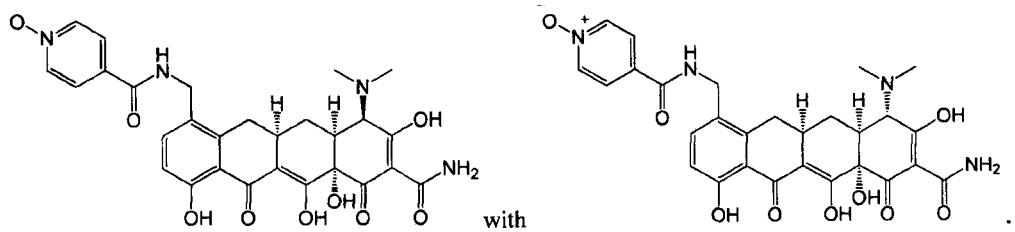 with

At column 21, replace

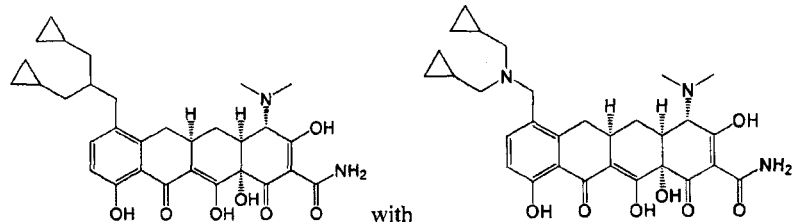 with

At column 31, replace

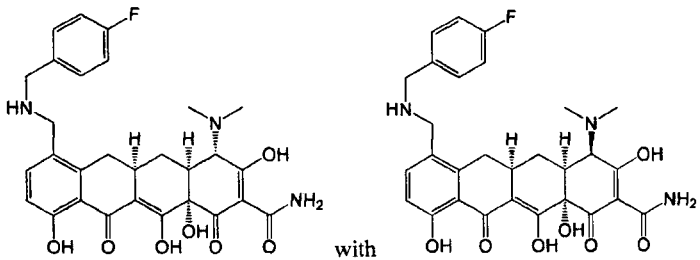 with

At column 31, replace

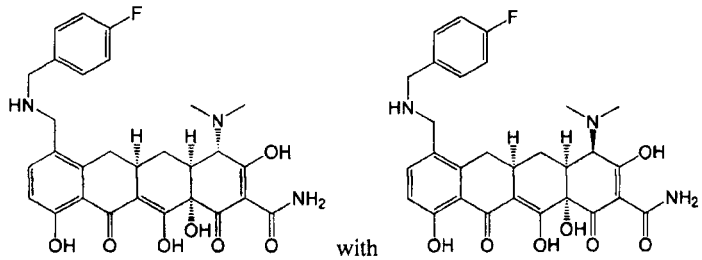 with

CERTIFICATE OF CORRECTION (continued)
U.S. Pat. No. 7,326,696 B2

At column 31, replace

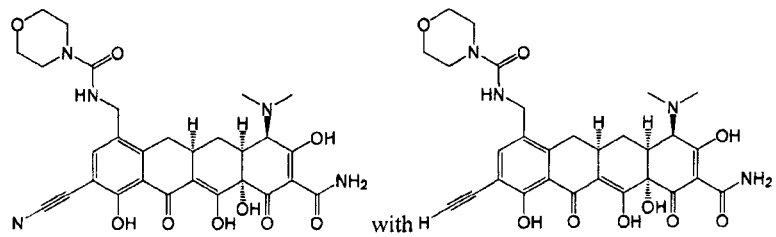 with .

At column 33, replace

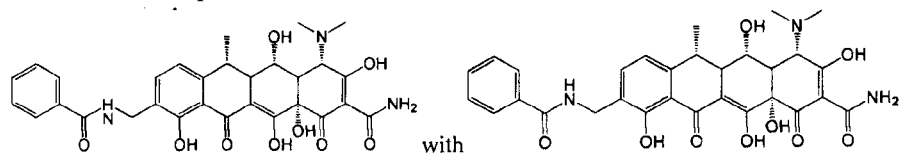 with .

At column 41, replace

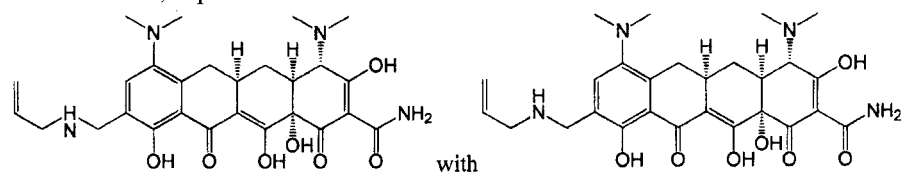 with .

At column 45, replace

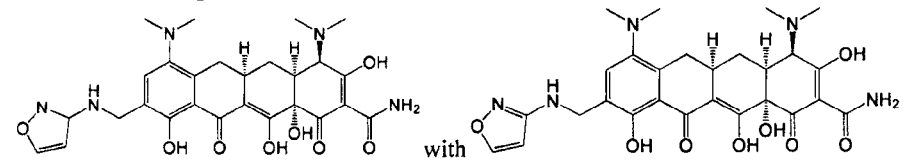 with .

At column 47, replace

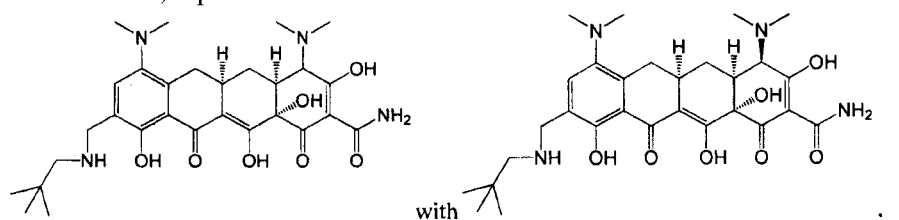 with .

At column 47, replace

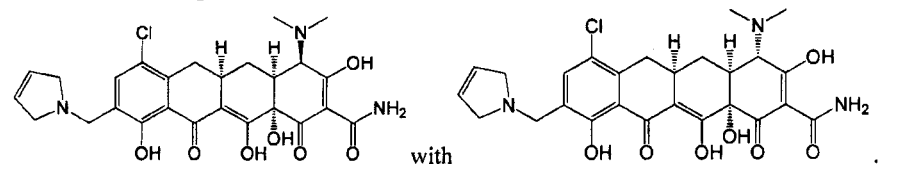 with .

CERTIFICATE OF CORRECTION (continued)
U.S. Pat. No. 7,326,696 B2

At column 53, replace

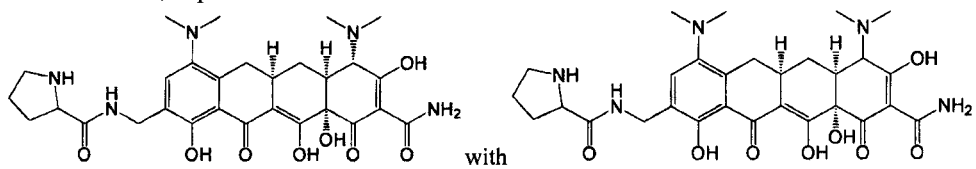

with

At column 53, replace

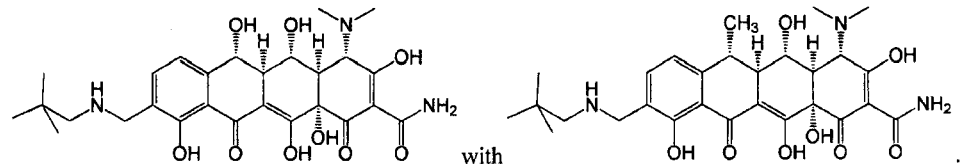

with

At column 53, replace

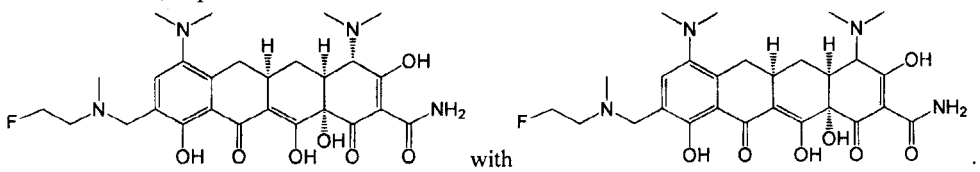

with

At column 57, replace

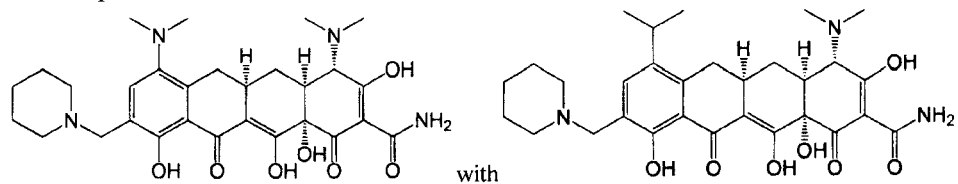

with

At column 59, replace

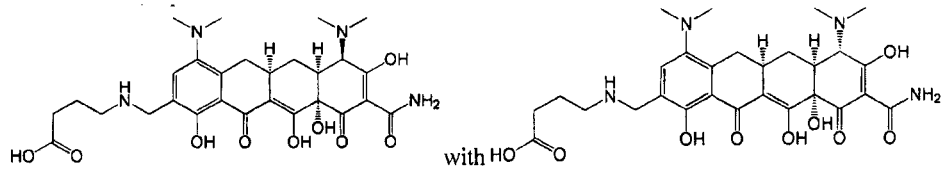

with

At column 61, replace

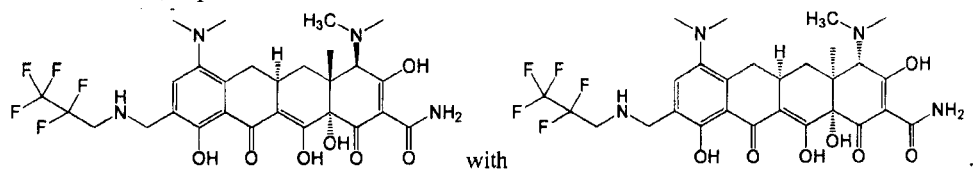

with

At column 61, replace

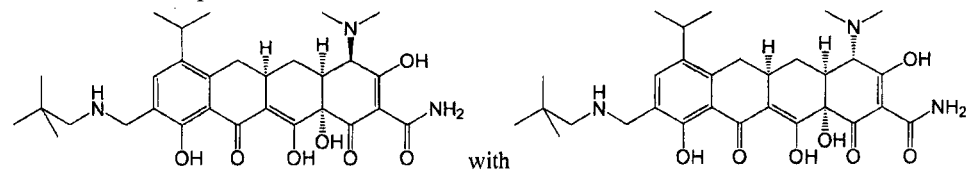

with

CERTIFICATE OF CORRECTION (continued)
U.S. Pat. No. 7,326,696 B2

At column 61, replace

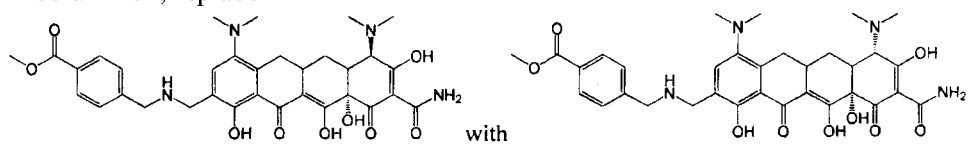 with

At column 63, replace

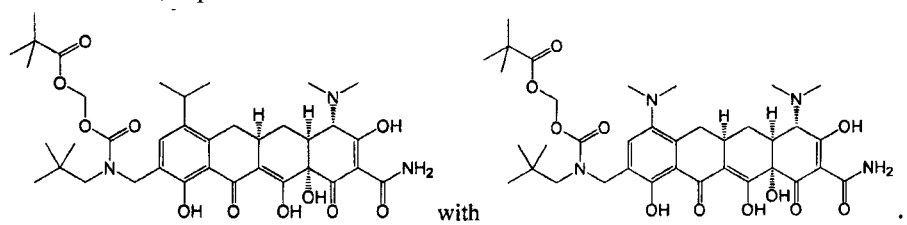 with

At column 67, replace

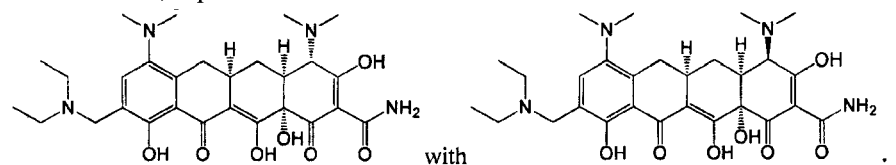 with

At column 75, replace

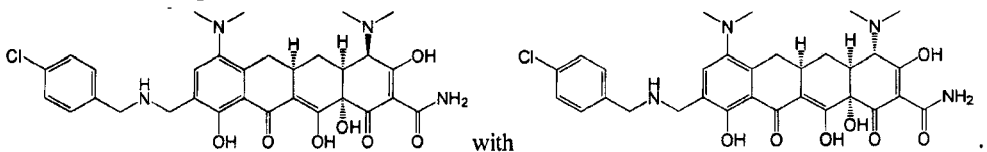 with

At column 77, replace

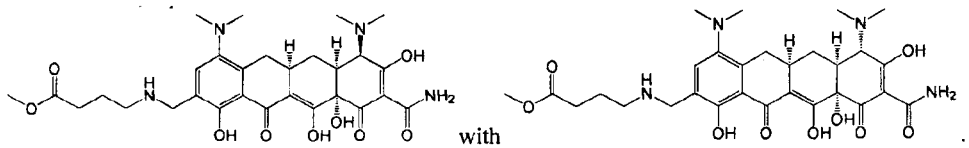 with

At column 77, replace

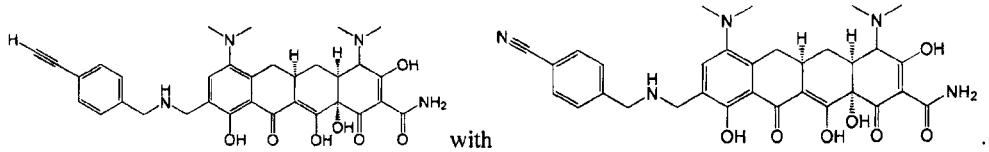 with

At column 77, replace

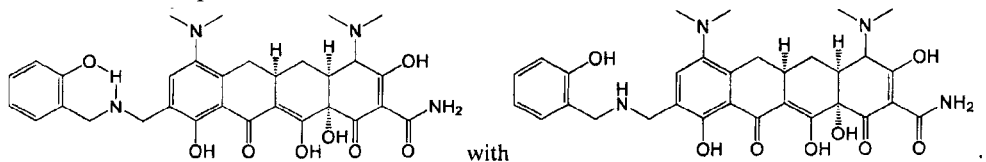 with

CERTIFICATE OF CORRECTION (continued)
U.S. Pat. No. 7,326,696 B2

At column 79, replace

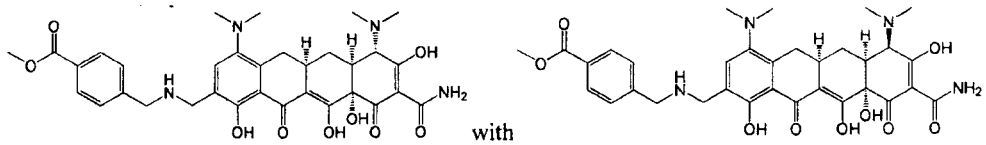

with

At column 79, replace

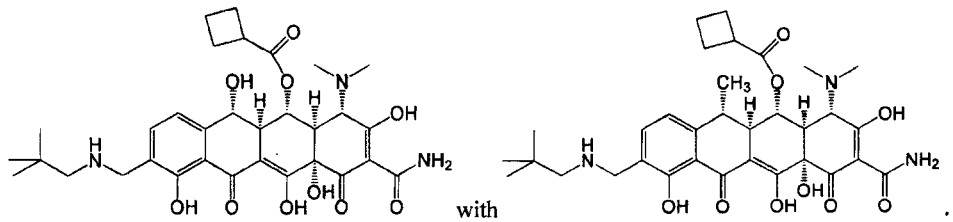

with

At column 83, replace

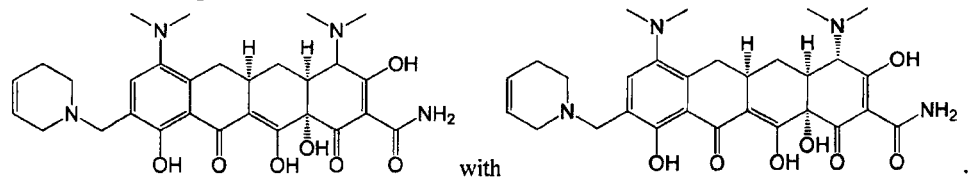

with

In the Claims:

At column 111, lines 22-25, replace "2. The tetracycline compound of claim 1, wherein $R^4$ is $NR^{4'}R^{4''}$, X is $CR^6R^{6'}$, $R^2$, $R^{2'}$, $R^6$, $R^{6',R8}$, $R^{10}$, $R^{11}$, and $R^{12}$ are each hydrogen; $R^{4'}$ and $R^{4''}$ are lower alkyl; and $R^5$ is hydroxyl or hydrogen." with --2. The tetracycline compound of claim 1, wherein $R^4$ is $NR^{4'}R^{4''}$, X is $CR^6R^{6'}$, $R^2$, $R^{2'}$, $R^6$, $R^{6'}$, $R^8$, $R^{10}$, $R^{11}$, and $R^{12}$ are each hydrogen; $R^{4'}$ and $R^{4''}$ are lower alkyl; and $R^5$ is hydroxyl or hydrogen.--.

At column 122, lines 35-45, replace

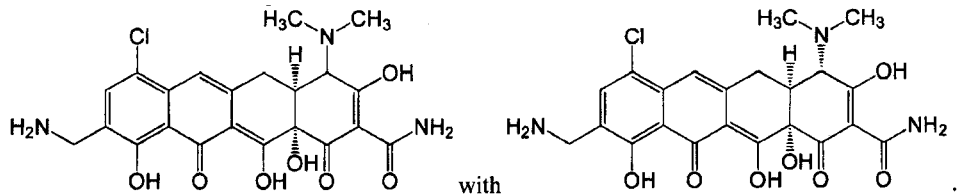

with

At column 133, lines 41-50, replace

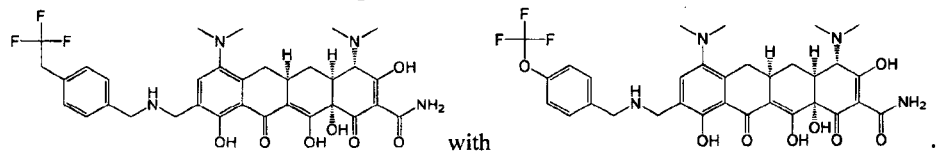

with

CERTIFICATE OF CORRECTION (continued)
U.S. Pat. No. 7,326,696 B2

At column 136, lines 41-50, replace

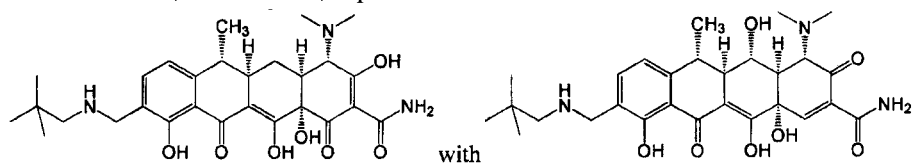 with

At column 136, lines 55-65, replace

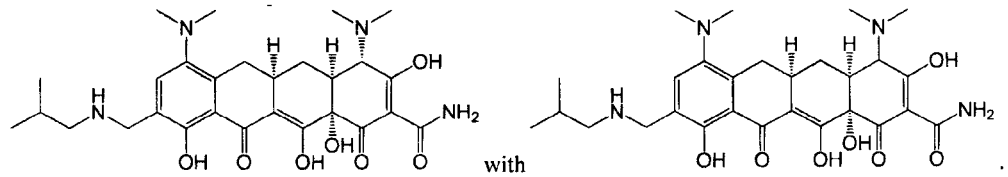 with

At column 137, lines 30-40, replace

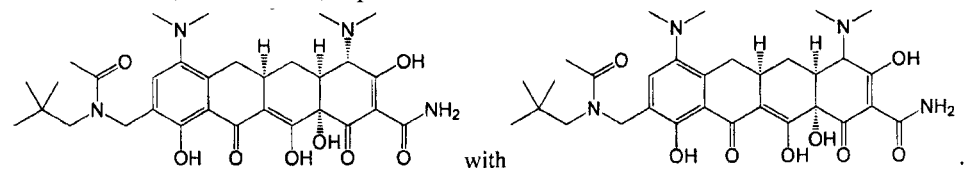 with

At column 137, lines 55-65, replace

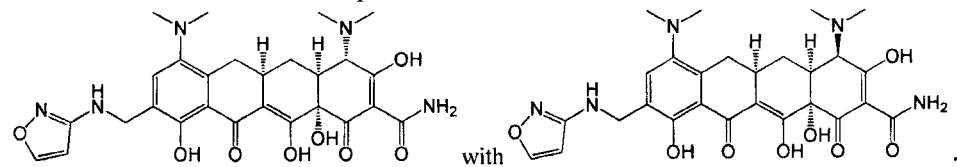 with

At column 147, lines 55-65, replace

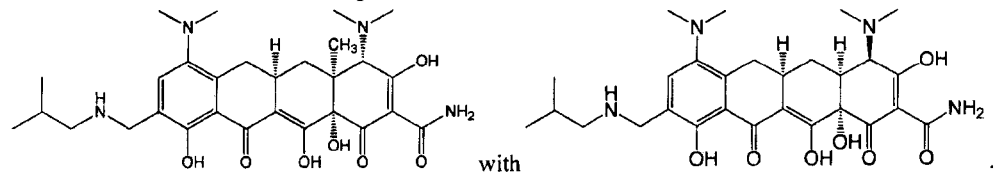 with

At column 149, lines 55-65, replace

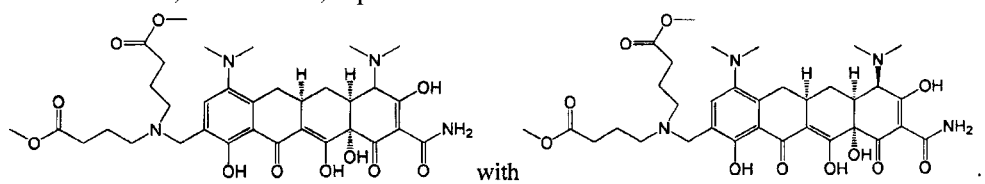 with